(12) United States Patent
Horowitz et al.

(10) Patent No.: US 9,169,318 B2
(45) Date of Patent: Oct. 27, 2015

(54) NEUTRALIZING MOLECULES TO VIRAL ANTIGENS

(75) Inventors: Lawrence Horowitz, Atherton, CA (US); Ramesh Bhatt, Belmont, CA (US); Arun Kashyap, Newark, CA (US)

(73) Assignee: Sea Lane Biotechnologies, Inc., Atherton, CA (US)

( * ) Notice: Subject to any disclaimer, the term of this patent is extended or adjusted under 35 U.S.C. 154(b) by 1043 days.

(21) Appl. No.: 13/185,386

(22) Filed: Jul. 18, 2011

(65) Prior Publication Data

US 2012/0093834 A1 Apr. 19, 2012

Related U.S. Application Data

(62) Division of application No. 12/413,308, filed on Mar. 27, 2009, now abandoned.

(60) Provisional application No. 61/040,459, filed on Mar. 28, 2008.

(51) Int. Cl.
| | |
|---|---|
| A61K 39/145 | (2006.01) |
| A61P 31/16 | (2006.01) |
| A61P 37/04 | (2006.01) |
| A61K 39/395 | (2006.01) |
| C07K 16/10 | (2006.01) |
| A61K 39/00 | (2006.01) |

(52) U.S. Cl.
CPC ............ *C07K 16/1018* (2013.01); *A61K 39/00* (2013.01); *A61K 2039/545* (2013.01); *C07K 2316/96* (2013.01); *C07K 2317/21* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/92* (2013.01); *C12N 2760/16111* (2013.01)

(58) Field of Classification Search
CPC ........... C07K 16/1018; C07K 2317/92; C07K 2317/622; C07K 2317/567; C07K 2317/565; C07K 2317/21; C07K 2316/96; C07K 2317/56; C07K 2317/55; C12N 2760/16111; A61K 2039/545
See application file for complete search history.

(56) References Cited

U.S. PATENT DOCUMENTS

| | | | | |
|---|---|---|---|---|
| 6,720,409 | B2 * | 4/2004 | Okuno et al. | ................ 536/23.1 |
| 2002/0054882 | A1 | 5/2002 | Okuno | |
| 2007/0004909 | A1 | 1/2007 | Johnson et al. | |
| 2007/0191314 | A1 | 8/2007 | Klucker et al. | |
| 2010/0297174 | A1 | 11/2010 | Garcia-Sastre et al. | |

FOREIGN PATENT DOCUMENTS

| | | |
|---|---|---|
| WO | WO 84/00687 A1 | 3/1984 |
| WO | WO 97/16208 | 5/1997 |
| WO | WO 01/35993 | 5/2001 |
| WO | WO 01/60402 | 8/2001 |
| WO | WO 2004/003019 | 1/2004 |
| WO | WO 2007/134327 | 11/2007 |
| WO | WO 2008/028946 | 3/2008 |
| WO | WO 2008/089073 | 7/2008 |
| WO | WO 2008/118970 | 10/2008 |
| WO | WO 2008/152236 | 12/2008 |
| WO | WO 2008/153236 A1 | 12/2008 |
| WO | WO 2009/079259 A2 | 6/2009 |

OTHER PUBLICATIONS

Bowie et al. Deciphering the message in protein sequences: tolerance to amino acid substitutions. Science 1990, vol. 247, No. 4948, pp. 1306-1310.*
Mateu et al. Non-additive effects of multiple amino acid substitutions on antigen-antibody recognition. European Journal of Immunology 1992, vol. 22, pp. 1

(56) References Cited

OTHER PUBLICATIONS

Gocnik, et al., "Antibodies specific to the HA2 glycopolypeptide of influenza. A virus haemagglutinin with fusion-inhibition activity contribute to the protection of mice against lethal infection", Journal of General Virology, vol. 88, Part 3., pp. 951-955, (2007).
Goudsmit, Japp, Presentation at 5th International Bird Flu Summit, Sep. 27, 2007, URL link http://investors.crucell.com/C/132631/present 2007 v2.html.
Govorkova, et al., "Immunization with reverse-genetics-produced H5N1 influenza vaccine protects ferrets against homologous and heterologous challenge", Efficacy of H5N1 vaccine in ferrets, pp. 159-167, (2006).
Hanson, et al., "Passive immunoprophylaxis and therapy with humanized monoclonal antibody specific for influenza A H5 hemagglutinin in mice", Respiratory Research, 7:126, pp. 1-10, (2006).
Holm et al "Functional mapping and single chain construction of the anti-cytokeratin 8 monoclonal antibody TS1", (2007) Mol. Immunol. 44: 1075-1084.
Holt, et al., "Domain antibodies: proteins for therapy", Trends in Biology, vol. 21, No. 11, pp. 484-490, (2003).
Jang et al, "The structural basis for DNA binding by an anti-DNA autoantibody", Molecular Immunol. vol. 35, Issue 18: 1207-1217, (1998).
Kashyap, et al., "Combinatorial antibody libraries from survivors of the Turkish H5N1 avian influenza outbreak reveal virus neutralization strategics", PNAS, vol. 105, No. 16, pp. 5986- 5991, (2008).
Kobayashi et al, "Tryptophan H33 plays an important role in pyrimidine (6-4) pyrimidone photoproduct binding by a high-affinity antibody", Protein Engineering 12: 879-884, (1999).
Kong, et al., "Successful treatment of avian influenza with convalescent plasma", Hong Kong Med., vol. 12, No. 6, p. 489, (2006).
Kumar et al, "Molecular Cloning and Expression of the Fabs of Human Autoantibodies in *Escherichia coli*. Determination of the heavy or light chain contribution to the anti-DNA/-Cardiolipin actibity of the Fab", J. Biol. Chem. 275: 35129-35136, (2000).
Lamminmaki, et al., "Expanding the conformational diversity by random insertions to CDRH2 results in improved anti-estradiol antibodies", J. Mol. Biol., 291: 589-602, (1999).
Law, et al., "Broadly neutralizing antibodies protect against hepatitis C virus quasispecies challenge", Nature Medicine, vol. 14, No. 1, pp. 25-27, (2008).
Lee, et al., High-affinity human antibodies from phage-displayed synthetic Fab libraries with a single framework scaffold, J. Mol. Biol., 340: 1073-1093, (2004).
Lerner, et al., "Manufacturing immunity to disease in a test tube: the magic bullet realized", Angew. Chem. Int. Rd., 45, pp. 8106-8125, (2006).
Lu, et al., "Passive immunotherapy for influenza A H5N1 virus infection with equine hyperimmune globulin F(ab')2 in mice", Respiratory Research, 7:43, pp. 1-7, (2006).
Luke, et al., "Meta-analysis: Convalescent blood products for Spanish influenza pneumonia: A future H5N1 treatment", Ann. Intern. Med. vol. 145, No. 8, pp. 599-609, (2006).
MacCallum et al. J. Mol. Biol. "Antibody-antigen interactions: Contact analysis and binding site topography", J. Mol. Biol., (1996) 262:732-745.

Okuno, et al., "A common neutralizing epitope conserved between hemagglutinins of influenza, a virus of H1 and H2 strains", Journal of Virology, vol. 67, No. 5, pp. 2552-2558, (1993).
Oner, et al., "Avian influenza A (H5N1) infection in eastern Turkey in 2006", The New England Journal of Medicine, vol. 355, No. 21, pp. 2179-2185, (2006).
Palese, et al., "Orthomyxoviridae: The viruses and their replication", Fields Virology, vol. 2, pp. 1647-1654, (2008).
Pan, et al., "Methionine oxidation in human IgG2 Fc decreases binding affinities to protein A and FcRn", Protein Science, vol. 18: 424-433, (2009).
Rudikoff et al "Single amino acid substitution altering antigen-binding specificity", PNAS, vol. 79, pp. 1979-1983, (1982).
Simmons, et al., "Prophylactic and therapeutic efficacy of human monoclonal antibodies against H5N1 influenza", PLOS Medicine, vol. 4, Issue 5, pp. 928-936, (2007).
Smirnov, et al., "An epitope shared by the hemagglutinins of II1, II2, II5 and II6 subtypes of influenza A virus", ACTA Virologica, vol. 43, No. 4, pp. 237-244, (1999).
Smirnov, et al., "Prevention and treatment of bronchopneumonia in mice caused by mouse-adapted variant of avian II5N2 influenza A virus using monoclonal antibody against conserved epitope in the HA stem region", Arch. Virol., 145: 1733-1741, (2000).
Smith-Gill et al, "Contributions of immunoglobulin heavy and light chains to antibody specificity for lysozyme and two haptens", J. Immunol. 139: 4135-4144, (1987).
Song et al, "Light chain of natural antibody plays a dominant role in protein antigen binding", Biochem. Biophys. Res. Comm. 268: 390-394, (2000).
Throsby, et al., "Heterosubtypic neutralizing monoclonal antibodies cross-protective against H5N1 recovered from human IgM memory B cells", PLOS One, vol. 3, Issue 12, pp. 1-15, (2008).
Vajdos et al. "Comprehensive functional maps of the antigen-binding site of an Anti-ErbB2 antibody obtained with shotgun scanning mutagenesis", (2002) J. Mol. Biol. 320, 415-428.
Ward et al, "Binding activities of a repertoire of single immunoglobulin variable domains secreted from *Escherichia coli*", Nature 341: 544-546, (1989).
Wu et al. "Humanization of a Murine monoclonal antibody by simultaneous optimization of framework and CDR residues", J. Mol. Biol. (1999) 294, 151-162.
Xu, et al., "Combinatorial surrobody libraries", Proceedings of the national academy of sciences, vol. 105, No. 31, pp. 10756-10761, (2008).
Zhou, et al., "Treatment with convalescent plasma for influenza A (H5N1) infection", The New England journal of medicine, 357:14, pp. 1450-1451, (2007).
Goudsmit, Japp, Presentation at Symposium for 10th Anniversary of Inflexal V, Apr. 26, 2007.
Lerner, et. al., "Rare antibodies from combinatorial libraries suggests an S.O.S. component of the human immunological repertoire", Mol. BioSyst., 2011, 7, 1004-1012.
PCT/US2010/034604 Search Report dated Mar. 24, 2011.
Horvath, et al. "A Hemagglutinin-Based Multipeptide Construct Elicits Enhanced Protective Immune Response in Mice Against Influenze A Virus Infection", Immunology Letters, Feb. 1998, vol. 60, No. 2/03, pp. 127-136.

* cited by examiner

Fig. 5

NEUTRALIZING MOLECULES TO VIRAL ANTIGENS

CROSS-REFERENCE TO RELATED APPLICATIONS

This application is a divisional of, and claims priority under 35 USC §120 to U.S. application Ser. No. 12/413,308 filed Mar. 27, 2009, now abandoned which claims priority under 35 USC §119(e) and the benefit of U.S. Provisional Application Ser. No. 61/040,459 filed Mar. 28, 2008, the entire disclosures of which are incorporated herein by reference in their entirety.

FIELD OF THE INVENTION

The present invention concerns methods and means for identifying, producing, and engineering neutralizing molecules against viral antigens, including influenza A viruses, and to the neutralizing molecules produced. The invention further concerns various uses of the molecules produced, including the design and production of vaccines utilizing the binding sites of the neutralizing molecules of the present invention on the target viral antigen, such as influenza A virus.

Viruses are infectious pathogens that can cause serious diseases including major threats for global public health, such as the influenza, AIDS, and hepatitis. A number of cancers have also been linked to viruses in conjunction with environmental factors. A typical virus is a sub-micrometer particle that has DNA or RNA packaged in a shell known as the capsid. Viral antigens protrude from the capsid and often fulfill important function in docking to the host cell, fusion, and injection of viral DNA/RNA. Antibody-based immune responses form a first layer of protection of the host from viral infection, however, in many cases a vigorous cellular immune response mediated by T-cells and NK-cells is required for effective viral clearance. When cellular immunity is unable to clear the virus, the infection can become chronic, and serum antibodies to the viral pathogen are used as first indicator for the diagnosis of the disease. Antibodies and antibody-like molecules would be valuable tools for passive immunization against, or for the treatment of such viral diseases.

One viral disease, the flu, is a contagious respiratory illness caused by influenza viruses. It causes mild to severe illness, and at times can lead to death. Annually, in the United States, influenza is contracted by 5-20% of the population, hospitalizing about 200,000, and causing the deaths of about 36,000.

Influenza viruses spread in respiratory droplets caused by coughing and sneezing, which are usually transmitted from person to person. Immunity to influenza surface antigens, particularly hemagglutinin, reduces the likelihood of infection and severity of disease if infection occurs. Although influenza vaccines are available, because a vaccine against one influenza virus type or subtype confers limited or no protection against another type or subtype of influenza, it is necessary to incorporate one or more new strains in each year's influenza vaccine.

Influenza viruses are segmented negative-strand RNA viruses and belong to the Orthomyxoviridae family. Influenza A virus consists of 9 structural proteins and codes additionally for one nonstructural NS1 protein with regulatory functions. The non-structural NS1 protein is synthesized in large quantities during the reproduction cycle and is localized in the cytosol and nucleus of the infected cells. The segmented nature of the viral genome allows the mechanism of genetic reassortment (exchange of genome segments) to take place during mixed infection of a cell with different viral strains.

The influenza A virus may be further classified into various subtypes depending on the different hemagglutinin (HA) and neuraminidase (NA) viral proteins displayed on their surface. Influenza A virus subtypes are identified by two viral surface glycoproteins, hemagglutinin (HA or H) and neuraminidase (NA or N). Each influenza virus subtype is identified by its combination of H and N proteins. There are 16 known HA subtypes and 9 known NA subtypes. Influenza type A viruses can infect people, birds, pigs, horses, and other animals, but wild birds are the natural hosts for these viruses. Only some influenza A subtypes (i.e., H1N1, H1N2, and H3N2) are currently in circulation among people, but all combinations of the 16 H and 9 NA subtypes have been identified in avian species, especially in wild waterfowl and shorebirds. In addition, there is increasing evidence that H5 and H7 influenza viruses can also cause human illness.

The HA of influenza A virus comprises two structurally distinct regions, namely, a globular head region and a stem region. The globular head region contains a receptor binding site which is responsible for virus attachment to a target cell and participates in the hemagglutination activity of HA. The stem region contains a fusion peptide which is necessary for membrane fusion between the viral envelope and an endosomal membrane of the cell and thus relates to fusion activity (Wiley et al., *Ann. Rev. Biochem.*, 56:365-394 (1987)).

A pandemic is a global disease outbreak. An influenza pandemic occurs when a new influenza A virus: (1) emerges for which there is little or no immunity in the human population, (2) begins to cause serious illness, and then (3) spreads easily person-to-person worldwide. During the 20$^{th}$ century there have been three such influenza pandemics. First, in 1918, the "Spanish Flu" influenza pandemic caused at least 500,000 deaths in the United States and up to 40 million deaths worldwide. This pandemic was caused by influenza A H1N1 subtype. Second, in 1957, the "Asian Flu" influenza pandemic, caused by the influenza A H2N2 subtype, resulted in at least 70,000 deaths in the United States and 1-2 million deaths worldwide. Most recently in 1968 the "Hong Kong Flu" influenza pandemic, caused by the influenza A H3N2 subtype, resulted in about 34,000 U.S. deaths and 700,000 deaths worldwide.

In 1997, the first influenza A H5N1 cases were reported in Hong Kong. This was the first time that this type of avian virus directly infected humans, but a pandemic did not result because human to human transmission was not observed.

Lu et al., *Resp. Res.* 7:43 (2006) (doi: 10.1186/1465-992-7-43) report the preparation of anti-H5N1 IgGs from horses vaccinated with inactivated H5N1 virus, and of H5N1-specifc F(ab')$_2$ fragments, which were described to protect BALB/c mice infected with H5N1 virus.

Hanson et al., *Resp. Res.* 7:126 (doi: 10.1186/1465-9921-7-126) describe the use of a chimeric monoclonal antibody specific for influenza A H5 virus hemagglutinin for passive immunization of mice.

Neutralizing antibodies to influenza viruses are disclosed in U.S. Application Publication No. 20080014205, published on Jan. 17, 2008.

In view of the severity of the respiratory illness caused by certain influenza A viruses, and the threat of a potential pandemic, there is a great need for effective preventative and treatment methods. The present invention addresses this need by providing influenza A neutralizing molecules against various H subtypes of the virus, including, without limitation, the H1, and H3 subtypes, and the H5 subtype of the influenza A virus. The invention further provides molecules capable of neutralizing more than one, and preferably all, isolates (strains) of a given subtype of the influenza A virus, including, without limitation, isolates obtained from various human and non-human species and isolates from victims and/or survivors of various influenza epidemics and/or pandemics.

Such neutralizing molecules can be used for the prevention and/or treatment influenza virus infection, including passive immunization of infected or at risk populations in cases of epidemics or pandemics.

SUMMARY OF THE INVENTION

In one aspect, the present invention concerns a molecule that can neutralize at least one subtype of an influenza virus and/or at least one isolate of an influenza virus. In one embodiment, the molecule is an antibody or an antibody-like molecule, wherein the molecule (i) neutralizes more than one subtype and/or more than one isolate of an influenza A virus, (ii) binds to a hemagglutinin (HA) antigen of the virus, and (iii) does not inhibit hemagglutination. In another embodiment, the molecule is a polypeptide comprising a VpreB sequence and/or a λ5 sequence. In one other embodiment, the molecule is a polypeptide comprising a VpreB sequence fused to a λ5 sequence. In another embodiment, the molecule is a κ-like surrogate light chain (SLC) construct comprising a Vκ-like and/or a JCκ sequence. In one embodiment, the molecule is an antibody. In another embodiment, the molecule is cross-reactive with at least two HA antigens selected from the group consisting of H1, H2, H3, H5, H6, H7, H8 and H9. In yet another embodiment, the molecule is cross-reactive with at least two HA antigens selected from the group consisting of H1, H2, H3, H5, and H9.

In all embodiments, the molecule is an antibody or an antibody-like molecule.

In all embodiments, the molecule is an antibody fragment.

In one aspect, the present invention concerns a neutralizing molecule neutralizing an influenza A virus subtype. In one embodiment, the molecule is an antibody or an antibody-like molecule, wherein the molecule (i) neutralizes more than one subtype and/or more than one isolate of an influenza A virus, (ii) binds to a hemagglutinin (HA) antigen of the virus, and (iii) does not inhibit hemagglutination. In other embodiments, the molecule does not prevent the influenza A virus' globular head region from binding the surface of a cell. In another embodiment, the cell is a cell to be infected. In another embodiment, the molecule does not prevent the influenza A virus from attaching to a cell In one embodiment, the molecule binds to an epitope of an H5 subtype of the HA antigen; an H1 subtype of the HA antigen; or an H3 subtype of the HA antigen. In one other embodiment, the H5, H3, or H1 epitope is displayed on the surface of an influenza A virus. In another embodiment, the H5 subtype is an H5N1 subtype. In one other embodiment, the H1 subtype is an H1N1 subtype. In another embodiment, the molecule neutralizes more than one isolate of the H5 and/or H3 and/or H1 influenza A virus subtypes. In another embodiment, the molecule neutralizes more than one isolate of the H5N1 and/or H3N1 and/or H1N1 influenza A virus subtypes. In one embodiment, the molecule neutralizes all isolates of the H5 and/or H3 and/or H1 influenza A virus subtypes.

In all embodiments, the influenza A virus subtypes that are neutralized may be further characterized by a neuraminidase (N) glycoprotein, including without limitation N1 and N2.

In one other embodiment, the molecule neutralizes at least an H5 and/or H3 and/or an H1 influenza A virus subtypes.

In another embodiment, the molecule neutralizes all H5 and/or H3 and/or H1 influenza A virus subtypes.

In another embodiment, the molecule neutralizes more than one H5 and/or H3 and/or H1 isolate of an influenza A virus subtype.

In yet another embodiment, the molecule neutralizes all H5 and/or H3 and/or H1 isolates of an influenza A virus subtype.

In another embodiment, the molecule neutralizes all H5 and/or H3 and/or H1 isolates of an influenza A virus subtype where the isolates are capable of infecting humans.

In all embodiments, the H5 subtype may comprise an H5 antigen and/or the H1 subtype may comprise an H1 antigen.

In one other embodiment, the present invention provides a molecule which binds essentially the same epitope as the epitope for a molecule having a heavy chain polypeptide containing an amino acid sequence shown as SEQ ID NO:4, SEQ ID NO:45, SEQ ID NO:9, or SEQ ID NO:61; or a consensus or variant sequence based upon said amino acid sequences, or a fragment thereof. In another embodiment, the molecule binds essentially the same epitope as the epitope for a molecule comprising a light chain polypeptide containing an amino acid sequence shown as SEQ ID NO:71, SEQ ID NO:140, SEQ ID NO:81, SEQ ID NO:158, SEQ ID NO:159, or SEQ ID NO:160; or a consensus or variant sequence based upon said amino acid sequences. In some embodiments, the present invention provides a molecule comprising a heavy chain polypeptide containing SEQ ID NO:4, SEQ ID NO:45, SEQ ID NO:9, or SEQ ID NO:61, or a consensus or variant sequence based upon said amino acid sequences, or a fragment thereof. In other embodiments, the molecule further contains a light chain polypeptide containing SEQ ID NO:71, SEQ ID NO:140, SEQ ID NO:81, SEQ ID NO:158, SEQ ID NO:159, or SEQ ID NO:160, or a consensus or variant sequence based upon said amino acid sequences, or a fragment thereof.

In one embodiment, the molecule binds essentially the same epitope as a molecule that includes a heavy chain polypeptide containing an amino acid sequence having the formula: $X_1$-$X_2$-Q-L-V-Q-S-G-$X_3$-E-V-$X_4$-K-P-G-$X_5$-S-V-$X_6$-$X_7$-S-C-K-$X_8$-S-G-G-$X_9$-F-S-S-Y-A-$X_{10}$-$X_{11}$-W-V-R-Q-A-P-G-Q-G-L-E-W-M-G-$X_{12}$-G-I-I-$X_{13}$-$X_{14}$-F-G-T-T-$X_{15}$-N-Y-A-Q-K-F-Q-G-R-$X_{16}$-T-$X_{17}$-T-A-D-$X_{18}$-$X_{19}$-T-S-T-A-Y-M-E-L-S-S-L-R-S-$X_{20}$-D-T-A-V-Y-Y-C-A-R-G-S-Y-Y-Y-E-$X_{21}$-$X_{22}$-L-D-Y-W-G-$X_{23}$-G-T-$X_{24}$ (SEQ ID NO:161), or a consensus or variant sequence based upon said amino acid sequences; wherein $X_1$ is Q or E; $X_2$ is V or M; $X_3$ is A or T; $X_4$ is K or Q; $X_5$ is S or A; $X_6$ is K or R; $X_7$ is V or L; $X_8$ is A, T or V; $X_9$ is T, S or A; $X_{10}$ is I or V; $X_{11}$ is S or T; $X_{12}$ is G or A; $X_{13}$ is P or G; $X_{14}$ is I or M; $X_{15}$ is A or T; $X_{16}$ is V or L; $X_{17}$ is I, L, or M; $X_{18}$ is K or E; $X_{19}$ is S, L or M; $X_{20}$ is E or D; $X_{21}$ is S, T or N; $X_{22}$ is S or T; $X_{23}$ is Q, K, G or R; and $X_{24}$ is L, T or M. In one embodiment, the amino acid sequence shown as SEQ ID NO:161 further comprises -V-T-V-S-S (SEQ ID NO: 170) or -V-R-V-S-S (SEQ ID NO: 171) at the C-terminal end following $X_{24}$.

In yet another embodiment, the molecule binds essentially the same the epitope as the epitope for a molecule containing a light chain polypeptide containing an amino acid sequence shown as SEQ ID NO:71, SEQ ID NO:140, SEQ ID NO:81, SEQ ID NO:158, SEQ ID NO:159, or SEQ ID NO:160, or a consensus or variant sequence based upon said amino acid sequences.

In some embodiments, the present invention provides a molecule comprising a heavy chain polypeptide containing a heavy chain polypeptide containing an amino acid sequence having the formula: $X_1$-$X_2$-Q-L-V-Q-S-G-$X_3$-E-V-$X_4$-K-P-G-$X_5$-S-V-$X_6$-$X_7$-S-C-K-$X_8$-S-G-G-$X_9$-F-S-S-Y-A-$X_{10}$-$X_{11}$-W-V-R-Q-A-P-G-Q-G-L-E-W-M-G-$X_{12}$-G-I-I-$X_{13}$-$X_{14}$-F-G-T-T-$X_{15}$-N-Y-A-Q-K-F-Q-G-R-$X_{16}$-T-$X_{17}$-T-A-D-

$X_{18}$-$X_{19}$-T-S-T-A-Y-M-E-L-S-S-L-R-S-$X_{20}$-D-T-A-V-Y-Y-C-A-R-G-S-Y-Y-Y-E-$X_{21}$-$X_{22}$-L-D-Y-W-G-$X_{23}$-G-T-$X_{24}$ (SEQ ID NO:161), or a consensus or variant sequence based upon said amino acid sequences; wherein $X_1$ is Q or E; $X_2$ is V or M; $X_3$ is A or T; $X_4$ is K or Q; $X_5$ is S or A; $X_6$ is K or R; $X_7$ is V or L; $X_8$ is A, T or V; $X_9$ is T, S or A; $X_{10}$ is I or V; $X_{11}$ is S or T; $X_{12}$ is G or A; $X_{13}$ is P or G; $X_{14}$ is I or M; $X_{15}$ is A or T; $X_{16}$ is V or L; $X_{17}$ is I, L, or M; $X_{18}$ is K or E; $X_{19}$ is S, L or M; $X_{20}$ is E or D; $X_{21}$ is S, T or N; $X_{22}$ is S or T; $X_{23}$ is Q, K, G or R; and $X_{24}$ is L, T or M. In one embodiment, the amino acid sequence shown as SEQ ID NO:161 further comprises -V-T-V-S-S (SEQ ID NO: 170) or -V-R-V-S-S (SEQ ID NO: 171) at the C-terminal end following $X_{24}$.

In other embodiments, the molecule further contains a light chain polypeptide containing an amino acid sequence shown as SEQ ID NO:71, SEQ ID NO:140, SEQ ID NO:81, SEQ ID NO:158, SEQ ID NO:159, or SEQ ID NO:160.

In all embodiments, the molecule is an antibody or an antibody-like molecule.

In one embodiment, the antibody or an antibody-like molecule (i) neutralizes more than one subtype and/or more than one isolate of an influenza A virus, (ii) binds to a hemagglutinin (HA) antigen of the virus, and (iii) does not inhibit hemagglutination.

In another embodiment, at least one of the virus subtypes and/or isolates neutralized by the molecules herein has the ability to infect humans.

In other embodiments, at least one of said isolates has been obtained from a human subject. In another embodiment, the human subject is or was diseased with an influenza virus at the time of obtaining the isolate. In other embodiments, the human subject recovered from infection with the influenza virus A. In another embodiment, the influenza virus A is an H5 subtype and/or an H1 subtype of influenza virus A.

In one embodiment, at least one of said isolates has been obtained from a non-human animal. In another embodiment, at least one of the isolates is from a bird, including, without limitation, wild-fowls and chicken.

In one embodiment, the molecules neutralize an H5 subtype and an H1 subtype.

In another embodiment, the neutralizing molecules of the present invention bind the H5 and/or H1 protein. In one embodiment, the H5 protein is an H5 HA protein. Preferably, the molecules bind more than one variant of the H5 protein, or, even more preferably, substantially all variants of the H5 protein.

In another embodiment, the molecule also binds to at least one additional HA antigen. In one other embodiment, the additional HA antigen is an H1 HA antigen. In one other embodiment, the molecule binds to substantially all variants of the H1 HA protein. In one embodiment, the at least one additional HA antigen is selected from the group consisting of H2, H3, H5, H6, H7, H8 and H9. In another embodiment, the at least one additional HA antigen also binds to HA antigen H5; HA antigens H3 and H9; or HA antigens H3, H5, and H9.

In other embodiments, the molecules described herein bind to the H5 protein and to at least one additional H protein, such as an H1 protein.

In a different aspect, the invention concerns compositions comprising the neutralizing molecules described herein. In one embodiment, the compositions comprise an antibody or antibody-like molecule described herein.

In a further aspect, the invention concerns a method for identifying a molecule capable of neutralizing more than one isolate of a single influenza A virus subtype or multiple influenza A virus subtypes. This method comprises identifying molecules, e.g., antibodies, antibody fragments, or antibody-like molecules in an antibody library, that react with both a first and a second isolate of the influenza A virus subtype or with a first and a second subtype of the influenza A virus, and subjecting the molecules identified to successive, alternating rounds of selection, based on their ability to bind the first and second isolates, or the first and second subtypes, respectively. In one embodiment, the method further comprises isolating the identified antibody.

In another embodiment, molecules that react with both a first and a second influenza A virus subtype isolate have been identified by at least two rounds of separate enrichment of molecules reacting with the first isolate and the second isolate, respectively, and recombining the molecules identified.

In another aspect, the present invention provides a method of identifying an antibody capable of neutralizing an isolate of an H5 influenza A virus and/or an isolate of an H1 influenza A virus; or a subtype of an H5 influenza A virus and/or a subtype of an H1 influenza A virus. In one embodiment, the method comprises identifying, in an antibody library, antibodies that react with both an H5 isolate and/or an H1 isolate; or an H5 subtype and/or an H1 subtype, and subjecting the antibodies identified to successive alternating rounds of selection, based on their ability to bind said H5 and/or H1 isolates or HA proteins; or said H5 and/or H1 subtypes or HA proteins, respectively. In another embodiment, the method comprises at least two rounds of selection. In one embodiment, the method further comprises isolating the identified antibody. In another embodiment, the H5 isolate is an H5 subtype of said influenza A virus or HA and/or said H1 isolate is an H1 subtype of said influenza A virus or HA. In yet another embodiment, the antibodies that react with both a first and a second influenza A virus subtype isolate or HA have been identified by at least two rounds of separate enrichment of antibodies reacting with the first isolate or HA and the second isolate or HA, respectively, and recombining the antibodies identified. In one other embodiment, the antibody that can react with both said H5 and said H1 influenza A subtype isolates or HAs is subjected to mutagenesis prior to being subjected to said successive alternating rounds of selection, based on their ability to bind said H5 and second H1 subtype isolates or HAs, respectively. In one other embodiment, the influenza A virus subtype is an H5 subtype or HA and said influenza A virus subtype is an H1 subtype or HA. In another embodiment, the H5 subtype is, or the HA is from, a 2006 Turkish isolate of the H5 virus; the H5 subtype is, or the HA is from, a 2003/2004 Vietnam isolate of the H5 virus; the H5 subtype is, or the HA is from, a 1997 Hong Kong isolate of the H5 virus; the H1 subtype is, or the HA is from, a New Calcdonia/20/99 isolate of the H1 virus; the H5 and/or said H1 subtypes or HAs originate from different species; or any combination thereof. In one other embodiment, at least one of said species is human; or at least one of said species is a bird. In another embodiment, the antibodies capable of binding said H5 and/or said H1 isolates are additionally selected based on their ability to bind more than one influenza A subtype.

In another embodiment, the molecule library is a phage display library. In one embodiment, the selection is performed by biopanning.

In another embodiment, the molecule that can react with both the first and the second influenza A subtype isolate is subjected to mutagenesis prior to being subjected to successive alternating rounds of selection, based on its ability to bind the first and second isolate, respectively. If desired, the molecules capable of binding the first and the second isolate are additionally selected based on their ability to bind more than one influenza A subtype.

The application of such enrichment techniques can be similarly applied to molecules in general, regardless of the target to which they bind. Such general enrichment/selection methods are specifically included as part of the invention.

In another embodiment, the invention concerns a collection of sequences shared by the neutralizing molecules of the present invention and identified by the methods described herein. In one other embodiment, the collection of sequences comprises one or more of the unique heavy and/or light chain sequences shown in Table 2 or a consensus or variant sequence based on said sequences. In another embodiment, the present invention provides a neutralizing antibody or a fragment thereof, identified by the methods described herein.

In a still further aspect, the invention concerns a method for treating an influenza A infection in a subject comprising of administering to the subject an effective amount of a neutralizing molecule or molecule composition herein.

In another aspect, the invention concerns a method for preventing influenza A infection comprising of administering to a subject at risk of developing influenza A infection an effective amount of a neutralizing molecule or molecule composition described herein. In one embodiment, the neutralizing molecule is a neutralizing antibody, antibody fragment, or antibody-like molecule.

In all embodiments, the subject is a human patient. In all embodiments, the subject is a subject at risk of developing an influenza A infection.

In a different aspect, the invention concerns a method for producing a diverse multifunctional molecule collection, comprising: (a) aligning CDR sequences of at least two functionally different molecules, e.g., antibodies, antibody fragments, or antibody-like molecules, (b) identifying amino acid residues conserved between the CDR sequences aligned, and (c) performing mutagenesis of multiple non-conserved amino acid residues in at least one of the CDR sequences aligned, using degenerate oligonucleotide probes encoding at least the amino acid residues present in the functionally different molecules at the non-conserved positions mutagenized to produce multiple variants of the aligned CDR sequences, and, if desired, repeating steps (b) and (c) with one or more of the variants until the molecule collection reaches a desired degree of diversity and/or size.

In a particular embodiment, the CDR sequences aligned have the same lengths.

In another embodiment, the conserved amino acid residues are retained in at least two of the CDR sequences aligned.

In a further aspect, the invention concerns a molecule collection comprising a plurality of neutralizing molecules, e.g., antibodies, antibody fragments, or antibody-like molecules, which differ from each other in at least one property.

The invention further concerns a method for uniquely identifying nucleic acids in a collection comprising labeling the nucleic acids with a unique barcode linked to or incorporated in the sequences of the nucleic acid present in such collection.

The invention further concerns a vaccine effective against influenza A virus containing a peptide or polypeptide that functionally mimics a neutralization epitope bound by a molecule of the present invention. In one embodiment, the vaccine is a synthetic vaccine. In another embodiment, the vaccine contains an attenuated influenza A virus, or a part thereof. In one other embodiment, the vaccine contains a killed influenza A virus, or part thereof. In another embodiment, the molecule that binds a neutralization epitope is one of the following:

(a) a molecule which (i) neutralizes more than one subtype and/or more than one isolate of an influenza A virus, (ii) binds to a hemagglutinin (HA) antigen of the virus, and (iii) does not prevent hemagglutination;

(b) a molecule which binds essentially the same epitope as the epitope for a molecule comprising a heavy chain polypeptide comprising an amino acid sequence selected from the group consisting of SEQ ID NO:4, SEQ ID NO:45, SEQ ID NO:9, and SEQ ID NO:61; or a consensus or variant sequence based upon said amino acid sequences, or a fragment thereof (c) a molecule which binds essentially the same epitope as the epitope for a molecule comprising a heavy chain polypeptide comprising an amino acid sequence having the formula: $X_1$-$X_2$-Q-L-V-Q-S-G-$X_3$-E-V-$X_4$-K-P-G-$X_5$-S-V-$X_6$-$X_7$-S-C-K-$X_8$-S-G-G-$X_9$-F-S-S-Y-A-$X_{10}$-$X_{11}$-W-V-R-Q-A-P-G-Q-G-L-E-W-M-G-$X_{12}$-G-I-I-$X_{13}$-$X_{14}$-F-G-T-T-$X_{15}$-N-Y-A-Q-K-F-Q-G-R-$X_{16}$-T-$X_{17}$-T-A-D-$X_{18}$-$X_{19}$-T-S-T-A-Y-M-E-L-S-S-L-R-S-$X_{20}$-D-T-A-V-Y-Y-C-A-R-G-S-Y-Y-Y-E-$X_{21}$-$X_{22}$-L-D-Y-W-G-$X_{23}$-G-T-$X_{24}$ (SEQ ID NO:161); or a consensus or variant sequence based upon said amino acid sequences, or a fragment thereof; wherein $X_1$ is Q or E; $X_2$ is V or M; $X_3$ is A or T; $X_4$ is K or Q; $X_5$ is S or A; $X_6$ is K or R; $X_7$ is V or L; $X_8$ is A, T or V; $X_9$ is T, S or A; $X_{10}$ is I or V; $X_{11}$ is S or T; $X_{12}$ is G or A; $X_{13}$ is P or G; $X_{14}$ is I or M; $X_{15}$ is A or T; $X_{16}$ is V or L; $X_{17}$ is I, L, or M; $X_{18}$ is K or E; $X_{19}$ is S, L or M; $X_{20}$ is E or D; $X_{21}$ is S, T or N; $X_{22}$ is S or T; $X_{23}$ is Q, K, G or R; and $X_{24}$ is L, T or M;

(d) a molecule comprising a heavy chain polypeptide comprising an amino acid sequence selected from the group consisting of SEQ ID NO:4, SEQ ID NO:45, SEQ ID NO:9, and SEQ ID NO:61; or a consensus or variant sequence based upon said amino acid sequences, or a fragment thereof; or (e) a molecule comprising a heavy chain polypeptide comprising an amino acid sequence having the formula: $X_1$-$X_2$-Q-L-V-Q-S-G-$X_3$-E-V-$X_4$-K-P-G-$X_5$-S-V-$X_6$-$X_7$-S-C-K-$X_8$-S-G-G-$X_9$-F-S-S-Y-A-$X_{10}$-$X_{11}$-W-V-R-Q-A-P-G-Q-G-L-E-W-M-G-$X_{12}$-G-I-I-$X_{13}$-$X_{14}$-F-G-T-T-$X_{15}$-N-Y-A-Q-K-F-Q-G-R-$X_{16}$-T-$X_{17}$-T-A-D-$X_{18}$-$X_{19}$-T-S-T-A-Y-M-E-L-S-S-L-R-S-$X_{20}$-D-T-A-V-Y-Y-C-A-R-G-S-Y-Y-Y-E-$X_{21}$-$X_{22}$-L-D-Y-W-G-$X_{23}$-G-T-$X_{24}$ (SEQ ID NO:161); or a consensus or variant sequence based upon said amino acid sequences, or a fragment thereof; wherein $X_1$ is Q or E; $X_2$ is V or M; $X_3$ is A or T; $X_4$ is K or Q; $X_5$ is S or A; $X_6$ is K or R; $X_7$ is V or L; $X_8$ is A, T or V; $X_9$ is T, S or A; $X_{10}$ is I or V; $X_{11}$ is S or T; $X_{12}$ is G or A; $X_{13}$ is P or G; $X_{14}$ is I or M; $X_{15}$ is A or T; $X_{16}$ is V or L; $X_{17}$ is I, L, or M; $X_{18}$ is K or E; $X_{19}$ is S, L or M; $X_{20}$ is E or D; $X_{21}$ is S, T or N; $X_{22}$ is S or T; $X_{23}$ is Q, K, G or R; and $X_{24}$ is L, T or M.

In one embodiment, the amino acid sequence shown as SEQ ID NO:161 further comprises -V-T-V-S-S (SEQ ID NO: 170) or -V-R-V-S-S (SEQ ID NO: 171) at the C-terminal end following $X_{24}$.

In another embodiment, the vaccine is based on a molecule that binds an HA antigen. In some other embodiments, the HA antigen is an H5 subtype or an H1 subtype. In one other embodiment, the antigen is displayed on the surface of an influenza A virus. In yet another embodiment, the peptide or polypeptide contains antigenic determinants that raise neutralizing molecules, e.g., antibodies.

In all embodiments, the present invention provides compositions that comprise a molecule described herein. In all embodiments, the molecule is an antibody, antibody fragment, or antibody-like molecule.

In one aspect, the present invention provides neutralizing antibodies identified by the methods described herein. In one embodiment, the neutralizing antibody is an antibody or an antibody fragment. In another embodiment, the neutralizing antibody or antibody fragment is capable of conferring passive immunity to an avian or mammalian subject against an influenza A virus infection. In another embodiment, the mammalian subject is a human. In one other embodiment, the influenza A virus infection is caused by an H5 subtype and/or an H1 subtype.

In another aspect, the present invention provides molecules capable of binding to and neutralizing a viral antigen. In one embodiment, the molecule comprises an antibody heavy chain variable domain comprising at least one substitution in the surface exposed cluster determined by amino acid positions 52A, 53, 73, and 74, following Kabat amino acid numbering, wherein said molecule is capable of binding to and neutralizing a viral antigen. In another embodiment, the molecule comprises a substitution at least one of amino acid positions 52A, 53, 73, and 74. In another embodiment, the molecule comprises a substitution at all of amino acid positions 52A, 53, 73, and 74. In another embodiment, the molecule further comprises a substitution at amino acid position 57. In another embodiment, the molecule further comprises P52G, I53M, K73E, and S74L/M substitutions. In another embodiment, the molecule additionally comprises an A57T substitution. In another embodiment, the molecule also comprises a substitution at least one of amino acid positions 24, 34, 35 and 50. In another embodiment, the molecule comprises substitutions at all of amino acid positions 24, 34, 35 and 50. In another embodiment, the molecule comprises A24T, I34V, S35T and G50A V24T, W34V, G35T and S50A substitutions.

In one aspect, the molecules of the present invention comprise a heavy chain variable domain sequence from a germline heavy chain. In one embodiment, the germ-line heavy chain is a $V_H$1e or a $V_H$1-69 germ-line heavy chain. In another embodiment, the rest of the heavy chain variable domain sequence retains the sequence of the germ-line heavy chain. In another embodiment, the germ-line heavy chain variable domain comprises at least one additional conservative substitution.

In one embodiment, the molecules further comprise a light chain sequence. In another embodiment, the light chain sequence is an antibody λ or κ light chain sequence. In one embodiment, the light chain sequence is a surrogate light chain sequence. In one other embodiment, the surrogate light chain sequence comprises a VpreB sequence and/or a λ5 sequence. In yet another embodiment, the surrogate light chain sequence comprises a VpreB sequence fused to a λ5 sequence. In another embodiment, the surrogate light chain sequence is a κ-like surrogate light chain (SLC) construct comprising a Vκ-like and/or a Jκ sequence.

In one embodiment, the viral antigen neutralized by the molecule is selected from the group consisting of viral antigens from influenza viruses, HIV-1, HIV-2, HTLV-I and -II viruses, SARS coronavirus, herpes simplex virus, Epstein Barr virus, cytomegalovirus, hepatitis virus (HCV, HAV, HBV, HDV, HEV), toxoplasma gondii virus, treponema pallidium virus, human T-lymphotrophic virus, encephalitis virus, West Nile virus, Dengue virus, Varicella Zoster Virus, rubeola, mumps, and rubella.

In another embodiment, the viral antigen is from an influenza virus or an HIV-1 or HIV-2 virus.

In one other aspect, the present invention provides vaccines effective against influenza A virus. In one embodiment, the vaccine comprises a peptide or polypeptide functionally mimicking a neutralization epitope of a molecule described herein. In another embodiment, the vaccine effective against a viral antigen comprises a peptide or polypeptide functionally mimicking a neutralization epitope of a molecule described herein. In one embodiment, the viral antigen is from an influenza virus or an HIV-1 or HIV-2 virus.

In another embodiment, the vaccine is a vaccine effective against an influenza A virus, comprising a peptide or polypeptide functionally mimicking a neutralization epitope of a molecule described herein. In one embodiment, the molecule is an antibody. In another embodiment, the antibody binds an HA antigen. In one other embodiment, the HA antigen is an H5 subtype. In one other embodiment, the HA antigen is an H1 subtype. In one other embodiment, the antigen is displayed on the surface of an influenza A virus. In one other embodiment, the peptide or polypeptide comprises antigenic determinants that raise neutralizing antibodies.

In one embodiment, the vaccine is a synthetic vaccine. In another embodiment, the vaccine comprises an attenuated influenza A virus, or a part thereof. In one other embodiment, the vaccine comprises a killed influenza A virus, or part thereof.

In other embodiments, the vaccine is suitable for oral administration, parenteral administration, transdermal delivery, or transmucosal delivery. In one embodiment, the transmucosal delivery is intra-nasal administration. In one other embodiment, the vaccine is for childhood immunization.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIG. 5 illustrates a representative mutagenesis method for generating a diverse multifunctional antibody collection by the "destinational mutagenesis" method. FIG. 5 discloses SEQ ID NOS 292, 291, 295, 293-294 and 296, respectively, in order of appearance.

DETAILED DESCRIPTION

A. Definitions

Figure 1:
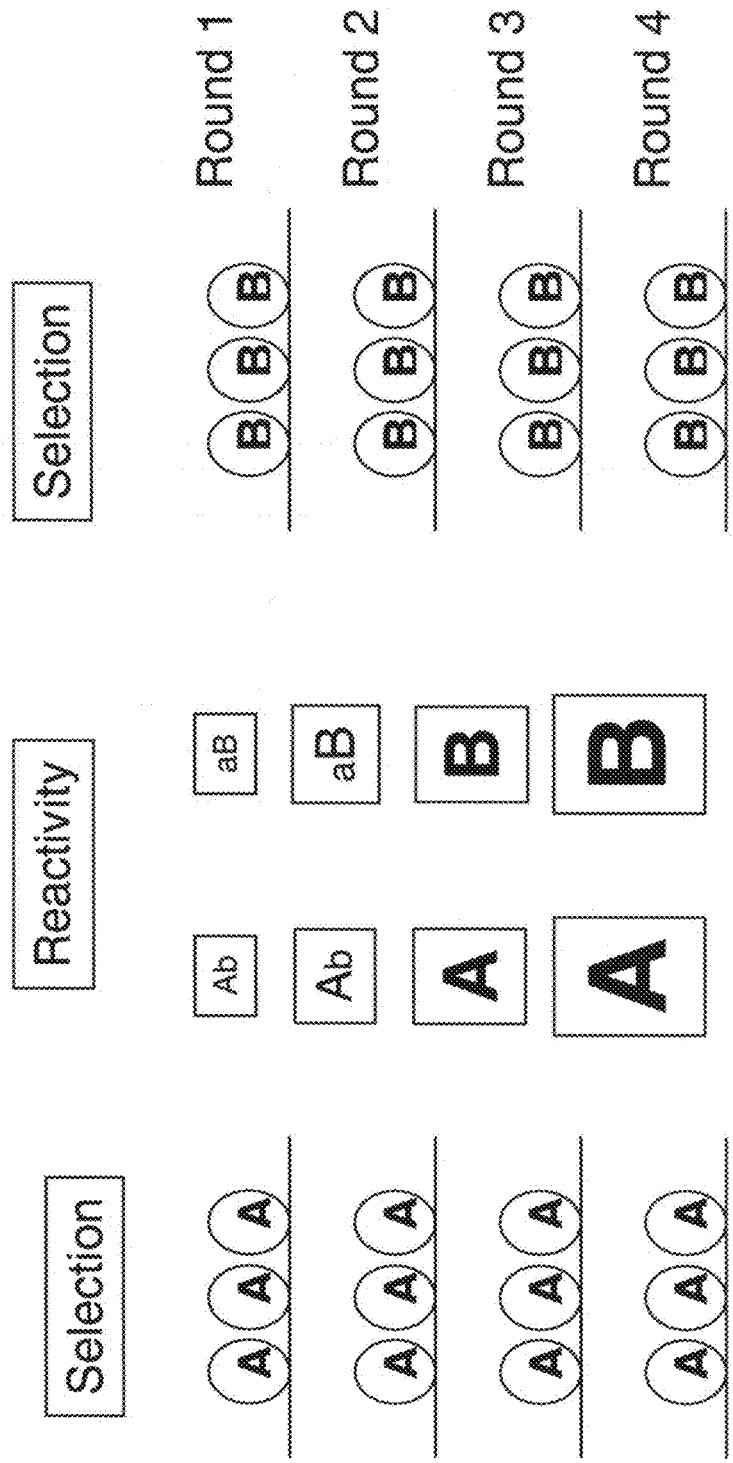
FIG. 1 illustrates a typical panning enrichment scheme for increasing the reactive strength towards two different targets, A and B. Each round of enrichment increases the reactive strength of the pool towards the individual target(s).
Figure 2:
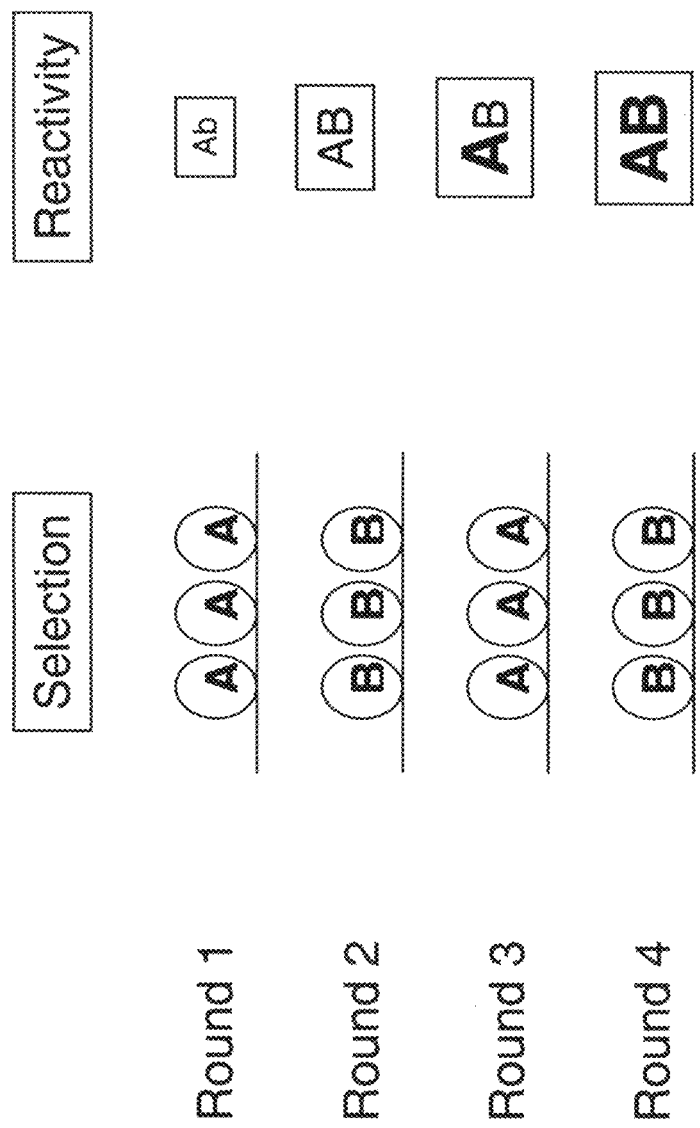
FIG. 2 illustrates a strategy for the selection of clones cross-reactive with targets A and B, in which each successive round reinforces the reactive strength of the resulting pool towards both targets.
Figure 3:
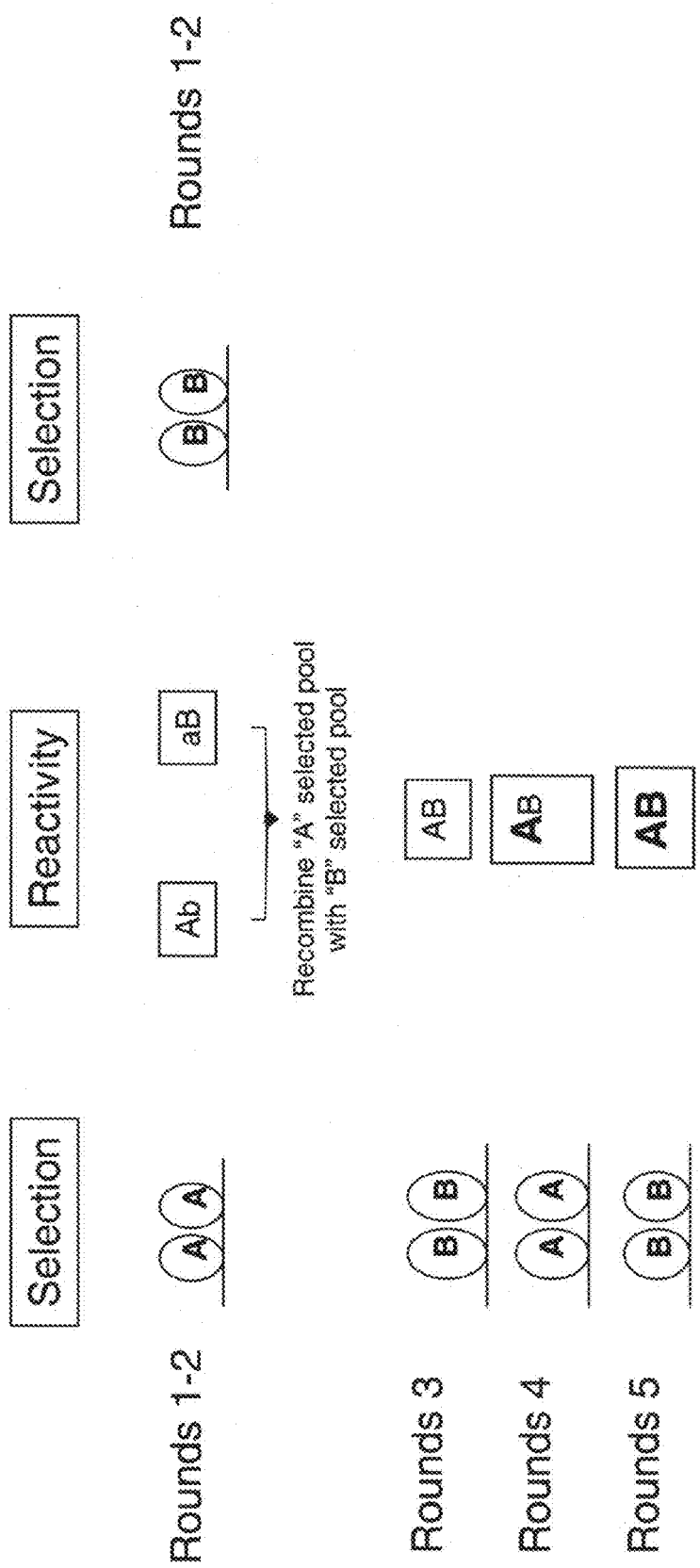
FIG. 3 illustrates a strategy for increasing the reactive strengths towards two different targets (targets A and B), by recombining parallel discovery pools to generate/increase cross-reactivity. Each round of selection of the recombined antibody library increases the reactive strength of the resulting pool towards both targets.
Figure 4:
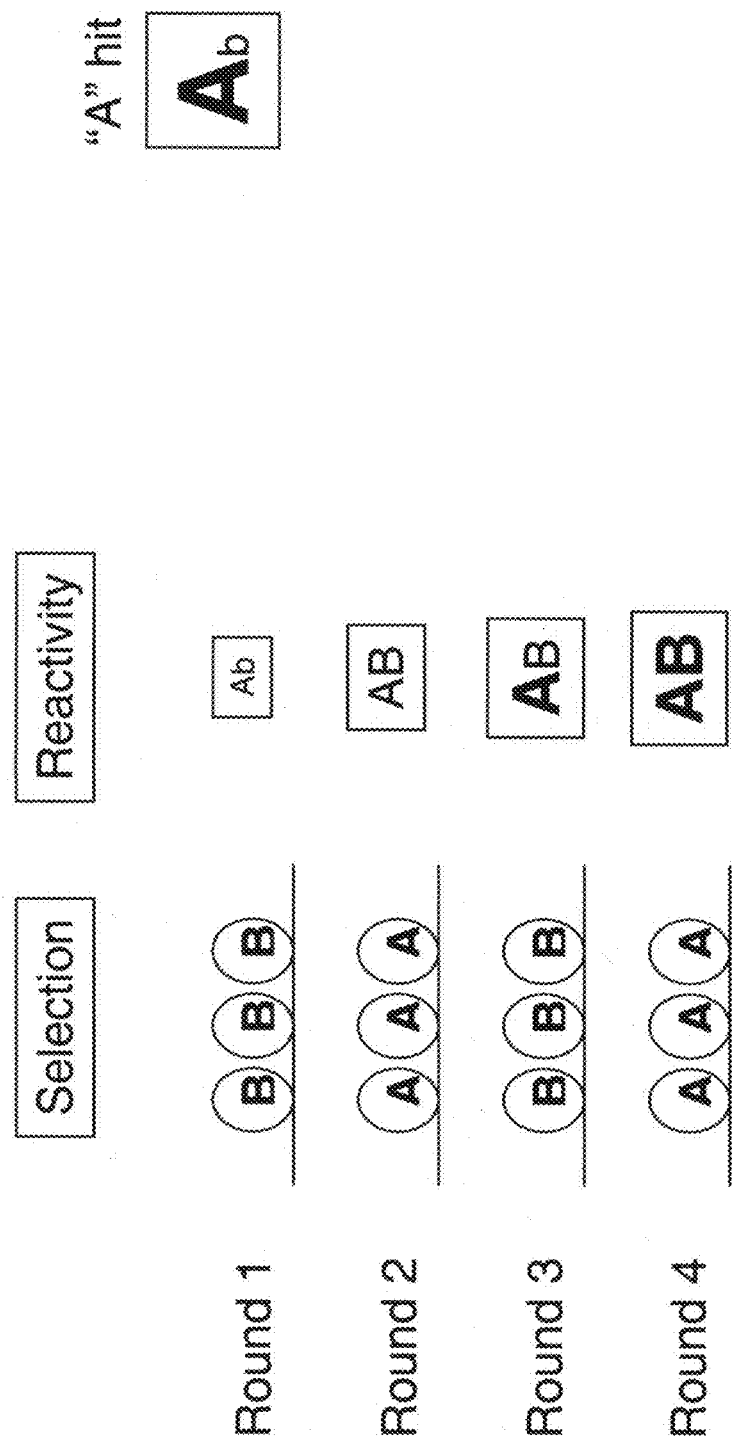
FIG. 4 illustrates a strategy for increasing cross-reactivity to a target B while maintaining reactivity to a target A. First, a clone reactive with target A is selected, then a mutagenic library of the clones reactive with target A is prepared, and selection is performed as shown, yielding one or more antibody clones that show strong reactivity with both target A and target B.
Figure 6:
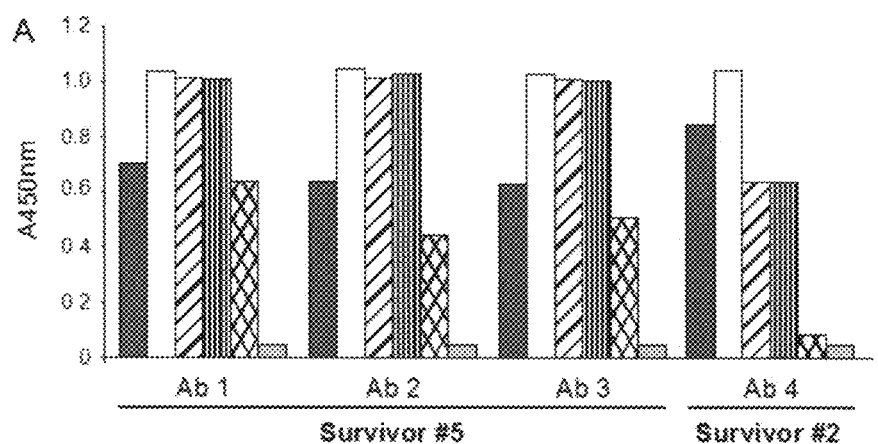
FIG. 6 shows the analysis of antibody binding to hemagglutinins from different influenza A subtypes.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The terms "influenza A subtype" or "influenza A virus subtype" are used interchangeably, and refer to influenza A virus variants that are characterized by a hemagglutinin (H) viral surface protein, and thus are labeled by an H number, such as, for example, H1, H3, and H5. In addition, the subtypes may be further characterized by a neuraminidase (N) viral surface protein, indicated by an N number, such as, for example, N1 and N2. As such, a subtype may be referred to by both H and N numbers, such as, for example, H1N1, H5N1, and H5N2. The terms specifically include all strains (including extinct strains) within each subtype, which usually result from mutations and show different pathogenic profiles. Such strains will also be referred to as various "isolates" of a viral subtype, including all past, present and future isolates. Accordingly, in this context, the terms "strain" and "isolate" are used interchangeably. Subtypes contain antigens based upon an influenza A virus. The antigens may be based upon a hemagglutinin viral surface protein and can be designated as "HA antigen". In some instances, such antigens are based on the protein of a particular subtype, such as, for example, an H1 subtype and an H5 subtype, which may be designated an H1 antigen and an H5 antigen, respectively.

The term "influenza" is used to refer to a contagious disease caused by an influenza virus.

In the context of the present invention, the term "antibody" (Ab) is used in the broadest sense and includes polypeptides which exhibit binding specificity to a specific antigen.

"Native antibodies" are usually heterotetrameric glycoproteins of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acad. Sci. U.S.A.* 82:4592 (1985).

The term "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J Mol Biol.* 1996. "Framework" or "FR" residues are those variable domain residues other than the hypervariable region residues as herein defined.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains.

The term "antibody fragment" is a portion of a full length antibody, generally the antigen binding or variable domain thereof. Examples of antibody fragments include, but are not limited to, Fab, Fab', F(ab')$_2$, and Fv fragments, linear antibodies, single-chain antibody molecules, diabodies, and multispecific antibodies formed from antibody fragments. Further examples of antibody fragments include, but are not limited to, scFv, (scFv)$_2$, dAbs (single-domain antibodies), and complementarity determining region (CDR) fragments, and minibodies, which are minimized variable domains whose two loops are amenable to combinatorial mutagenesis.

The term "monoclonal antibody" is used to refer to an antibody molecule synthesized by a single clone of B cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, *Nature* 256:495 (1975); *Eur. J. Immunol.* 6:511 (1976), by recombinant DNA techniques, or may also be isolated from phage antibody libraries.

The term "polyclonal antibody" is used to refer to a population of antibody molecules synthesized by a population of B cells.

"Single-chain Fv" or "sFv" antibody fragments comprise the $V_H$ and $V_L$ domains of antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Plückthun in *The Pharmacology of Monoclonal Antibodies*, vol. 113, Rosenburg and Moore eds. Springer-Verlag, New York, pp. 269-315 (1994). Single-chain antibodies are disclosed, for example in WO 88/06630 and WO 92/01047.

The term "diabody" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444-6448 (1993).

The term "minibody" is used to refer to an scFv-CH3 fusion protein that self-assembles into a bivalent dimer of 80 kDa (scFv-CH3)$_2$.

The term "aptamer" is used herein to refer to synthetic nucleic acid ligands that bind to protein targets with high specificity and affinity. Aptamers are known as potent inhibitors of protein function.

A dAb fragment (Ward et al., *Nature* 341:544 546 (1989)) consists of a $V_H$ domain or a VL domain.

As used herein the term "antibody binding regions" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof) such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "bispecific antibody" refers to an antibody that shows specificities to two different types of antigens. The term as used herein specifically includes, without limitation, antibodies which show binding specificity for a target antigen and to another target that facilitates delivery to a particular tissue. Similarly, multi-specific antibodies have two or more binding specificities.

The expression "linear antibody" is used to refer to comprising a pair of tandem Fd segments ($V_H$-$C_H$1-$V_H$-$C_H$1) which form a pair of antigen binding regions. Linear antibodies can be bispecific or monospecific and are described, for example, by Zapata et al., *Protein Eng.* 8(10):1057-1062 (1995).

For the purposes of the present invention, the term "antibody-like molecule" includes any molecule, other than an antibody fragment as hereinabove defined, that is capable of binding to and neutralizing a viral antigen. The term specifically includes, without limitation, pre-B cell receptor (pre-BCR) like structures, referred to as "surrobodies," including surrogate light chain (SLC) elements, as described, for example, in PCT Publication No. WO 2008/118970, published Oct. 2, 2008, and in Xu et al., *Proc. Natl. Acad. Sci. USA*, 105(31):10756-61 (2008). The SLC is a nondiversified heterodimer composed of the noncovalently associated Vpre-B and λ5 proteins. The VpreB chain is homologous to a Vλ Ig domain, and the λ5 chain is homologous to the Cλ domain of canonical antibodies, respectively. The heterodimeric SLC is covalently associated with the heavy chain in the pre-BCR complex by disulfide bonds between the Cλ domain and the first constant domain of the pre-BCR HC. A unique feature of the SLC is that the VpreB1 and the λ5 domains each have noncanonical peptide extensions. VpreB1 has an additional 21 residues on its C terminus, and λ5 has a 50-aa-long tail on its N terminus (see, e.g. Vettermann et al., *Semin. Immunol.* 18:44-55 (2006)). The surrobody structures specifically include, without limitation, the native trimeric pre-BCR-like functional unit of the pre-BCR, fusion of VpreB1 to λ5, and trimers that eliminated either the λ5 N-terminal 50 aa or the VpreB1 C-terminal 21 aa or both peptide extensions. In addition, chimeric constructs using the constant components of classical antibody light chains are specifically included within the definition of surrobodies.

Other representatives of "antibody-like molecules," as defined herein, are similar structures comprising antibody surrogate κ light chain sequences, where κ light chain sequences are optionally partnered with another polypeptide, such as, for example, antibody heavy and/or light chain domain sequences. A κ-like B cell receptor (κ-like BCR) has been identified, utilizing a κ-like surrogate light chain (κ-like SLC) (Frances et al., *EMBO J* 13:5937-43 (1994); Thompson et al., *Immunogenetics* 48:305-11 (1998); Rangel et al., *J Biol Chem* 280:17807-14 (2005)). Rangel et al., *J Biol Chem* 280(18):17807-17814 (2005) report the identification and molecular characterization of a Vκ-like protein that is the product of an unrearranged Vκ gene, which turned out to the be identical to the cDNA sequence previously reported by Thompson et al., *Immunogenetics* 48:305-311 (1998). Whereas, Frances et al., *EMBO J* 13:5937-43 (1994) reported the identification and characterization of a rearranged germline JCk that has the capacity to associate with μ heavy chains at the surface of B cell precursors, thereby providing an alternative to the λ5 pathway for B cell development. It has been proposed that κ-like and λ-like pre-BCRs work in concert to promote light chain rearrangement and ensure the maturation of B cell progenitors. For a review, see McKeller and Martinez-Valdez *Seminars in Immunology* 18:4043 (2006).

The term "λ5" is used herein in the broadest sense and refers to any native sequence or variant λ5 polypeptide, specifically including, without limitation, native sequence human and other mammalian λ5 polypeptides, and variants formed by posttranslational modifications, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less then 95%, or less than 90%, or less then 85%, ore less than 80%, or less than 75%, or less then 70%, or less than 65%, or less than 60% identical in its amino acid sequence to a native antibody λ or κ light chain sequence. Variant VpreB polypeptides specifically include, without limitation, VpreB polypeptides in which the non-Ig-like unique tail at the C-terminus of the VpreB sequence is partially or completely removed. The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less then 95%, or less than 90%, or less then 85%, ore less than 80%, or less than 75%, or less then 70%, or less than 65%, or less than 60% identical in its amino acid sequence to a native antibody λ or κ light chain sequence. Variant polypeptides specifically include, without limitation. λ5 polypeptides in which the unique tail at the N-terminus of the λ5 sequence is partially or completely removed.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term surrogate light chain sequence, as defined herein, means any polypeptide sequence that comprises a "VpreB sequence" and/or a "λ5 sequence," as hereinabove defined.

The terms "κ-like surrogate light chain variable domain," "Vκ-like SLC," and "Vκ-like" are used interchangeably, and refer to any native sequence polypeptide that is the product of an unrearranged Vκ gene, and variants thereof. In one embodiment, variants of native sequence Vκ-like polypeptides comprise a C-terminal extension (tail) relative to antibody κ light chain sequences. In a particular embodiment, variants of native sequence Vκ-like polypeptides retain at least part, and preferably all, of the unique C-terminal extension (tail) that distinguishes the Vκ-like polypeptides from the corresponding antibody κ light chains. In another embodiment, the C-terminal tail of the variant Vκ-like polypeptide is a sequence not naturally associated with the rest of the sequence. In the latter embodiment, the difference between the C-terminal tail naturally present in the native Vκ-like sequence and the variant sequence may result from one or more amino acid alterations (substitutions, insertions, deletions, and/or additions), or the C-terminal tail may be identical with a tail present in nature in a different Vκ-like protein. The Vκ-like polypeptides may contain amino acid alterations in regions corresponding to one or more of antibody κ light chain CDR1, CDR2 and CDR3 sequences. In all instances, the variants can, and preferably do, include a C-terminal extension of at least four, or at least five, or at least six, or at least seven, or at least eight, or at least nine, or at least ten amino acids, preferably 4-100, or 4-90, or 4-80, or 4-70, or 4-60, or 4-50, or 4-45, or 4-40, or 4-35, or 4-30, or 4-25, or 4-20, or 4-15, or 4-10 amino acid residues relative to a native antibody κ light chain variable region sequence. As defined herein, Vκ-like polypeptide variant will be different from a native antibody κ or λ light chain sequence or a fragment thereof, and will preferably retain at least about 65%, or at least about 70%, or at least about 75%, or at least about 80%, or at least about 85%, or at least about 90%, or at least about 95%, or at least about 98% sequence identity with a native sequence Vκ polypeptide. In another preferred embodiment, the Vκ-like polypeptide variant will be less then 95%, or less than 90%, or less then 85%, ore less than 80%, or less than 75%, or less then 70%, or less than 65%, or less than 60%, or less then 55%, or less than 50%, or less than 45%, or less than 40% identical in its amino acid sequence to a native antibody λ or κ light chain sequence. In other embodiments, the sequence identity is between about 40% and about 95%, or between about 45% and about 90%, or between about 50% and about 85%, or between about 55% and about 80%, or between about 60% and about 75%, or between about 60% and about 80%, or between about 65% and about 85%, or between about 65% and about 90%, or between about 65% and about 95%. In all embodiments, preferably the Vκ-like polypeptides are capable of binding to a target.

The terms "JCκ" and "JCκ-like" are used interchangeably, and refer to native sequence polypeptides that include a portion identical to a native sequence κ J-constant (C) region segment and a unique N-terminal extension (tail), and variants thereof. In one embodiment, variants of native sequence JCκ-like polypeptides comprise an N-terminal extension (tail) that distinguishes them from an antibody JC segment. In a particular embodiment, variants of native sequence JCκ-like polypeptides retain at least part, and preferably all, of the unique N-terminal extension (tail) that distinguishes the JCκ-like polypeptides from the corresponding antibody κ light chain JC segments. In another embodiment, the N-terminal tail of the variant JCκ-like polypeptide is a sequence not naturally associated with the rest of the sequence. In the latter embodiment, the difference between the N-terminal tail naturally present in the native JCκ-like sequence and the variant sequence may result from one or more amino acid alterations (substitutions, insertions, deletions, and/or additions), or the N-terminal tail may be identical with a tail present in nature in a different JCκ-like protein. Variants of native sequence JCκ-like polypeptides may contain one or more amino acid alterations in the part of the sequence that is identical to a native antibody κ variable domain JC sequence. In all instances, the variants can, and preferably do, include an N-terminal extension (unique N-terminus) of at least four, or at least five, or at least six, or at least seven, or at least eight, or at least nine, or at least ten amino acids, preferably 4-100, or 4-90, or 4-80, or 4-70, or 4-60, 4-50, or 4-45, or 4-40, or 4-35, or 4-30, or 4-25, or 4-20, or 4-15, or 4-10 amino acid residues relative to a native antibody κ light chain JC sequence. The JCκ-like polypeptide variant, as defined herein, will be different from a native antibody λ or κ light chain JC sequence, or a fragment thereof, and will preferably retain at least about 65%, or at least about 70%, or at least about 75%, or at least about 80%, or at least about 85%, or at least about 90%, or at least about 95%, or at least about 98% sequence identity with a native sequence JC polypeptide. In another preferred embodiment, the JCκ-like polypeptide variant will be less then 95%, or less than 90%, or less then 85%, ore less than 80%, or less than 75%, or less then 70%, or less than 65%, or less than 60% identical in its amino acid sequence to a native antibody λ or κ light chain JC sequence. In other embodiments, the sequence identity is between about 40% and about 95%, or between about 45% and about 90%, or between about 50% and about 85%, or between about 55% and about 80%, or between about 60% and about 75%, or between about 60% and about 80%, or between about 65% and about 85%, or between about 65% and about 90%, or between about 65% and about 95%.

Percent amino acid sequence identity may be determined using the sequence comparison program NCBI-BLAST2 (Altschul et al., Nucleic Acids Res. 25:3389-3402 (1997)). The NCBI-BLAST2 sequence comparison program may be downloaded from www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822(b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogues thereof (e.g., DNA or RNA generated using nucleotide analogues or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at a specified position," refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

The term "neutralizing molecule" is used herein in the broadest sense and refers to any molecule that inhibits a virus from replicatively infecting a target cell, irrespective of the mechanism by which neutralization is achieved, The neutralizing molecule preferably an antibody or an antibody-like molecule, as hereinabove defined, Neutralization can be achieved, for example, by inhibiting the attachment or adhesion of the virus to the cell surface, e.g., by engineering an molecule, such as an antibody or antibody-like molecule, that binds directly to, or close by, the site responsible for the attachment or adhesion of the virus. Neutralization can also be achieved by a molecule, such as an antibody or antibody-like molecule, directed to the virion surface, which results in the aggregation of virions. Neutralization can further occur by inhibition of the fusion of viral and cellular membranes following attachment of the virus to the target cell, by inhibition of endocytosis, inhibition of progeny virus from the infected cell, and the like. The neutralizing molecules, such as antibodies or antibody-like molecules, of the present invention are not limited by the mechanism by which neutralization is achieved.

The term "antibody repertoire" is used herein in the broadest sense and refers to a collection of antibodies or antibody fragments which can be used to screen for a particular property, such as binding ability, binding specificity, ability of gastrointestinal transport, stability, affinity, and the like. The term specifically includes antibody libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

Similarly, a "repertoire of antibody-like molecules" (as hereinabove defined) refers to a collection of such molecules which can be used to screen for a particular property, such as binding ability, binding specificity, ability of gastrointestinal transport, stability, affinity, and the like. The term specifically includes surrobody libraries and libraries of κ-like light chain constructs (as hereinabove defined), including all forms of combinatorial libraries, such as, for example, phage display libraries. Combinatorial surrobody libraries are disclosed, for example, in Xu et al., (2008), supra.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

An "antibody phage display library" refers to a phage display library that displays antibodies or antibody fragments. The antibody library includes the population of phage or a collection of vectors encoding such a population of phage, or cell(s) harboring such a collection of phage or vectors. The library can be monovalent, displaying on average one single-chain antibody or antibody fragment per phage particle, or multi-valent, displaying, on average, two or more antibodies or antibody fragments per viral particle. The term "antibody fragment" includes, without limitation, single-chain Fv (scFv) fragments and Fab fragments. Preferred antibody libraries comprise on average more than $10^6$, or more than $10^7$, or more than $10^8$, or more than $10^9$ different members.

The term "filamentous phage" refers to a viral particle capable of displaying a heterogenous polypeptide on its surface, and includes, without limitation, f1, fd, Pf1, and M13. The filamentous phage may contain a selectable marker such as tetracycline (e.g., "fd-tet"). Various filamentous phage display systems are well known to those of skill in the art (see, e.g., Zacher et al., Gene 9:127-140 (1980), Smith et al., Science 228:1315-1317 (1985); and Parmley and Smith, Gene 73:305-318 (1988)).

The term "panning" is used to refer to the multiple rounds of screening process in identification and isolation of phages carrying compounds, such as antibodies, with high affinity and specificity to a target.

The term "non-human animal" as used herein includes, but is not limited to, mammals such as, for example, non-human primates, rodents (e.g., mice and rats), and non-rodent animals, such as, for example, rabbits, pigs, sheep, goats, cows, pigs, horses and donkeys. It also includes birds (e.g., chickens, turkeys, ducks, geese and the like). The term "non-primate animal" as used herein refers to mammals other than primates, including but not limited to the mammals specifically listed above.

The phrase "functionally different antibodies," and grammatical variants thereof, are used to refer to antibodies that differ from each other in at least one property, including, without limitation, binding specificity, binding affinity, and any immunological or biological function, such as, for example, ability to neutralize a target, extent or quality of biological activity, etc.

The phrase "conserved amino acid residues" is used to refer to amino acid residues that are identical between two or more amino acid sequences aligned with each other.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

B. General Techniques

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; *Antibody Phage Display: Methods and Proto-*

*cols*, P. M. O'Brian and R. Aitken, eds., Humana Press, In: Methods in Molecular Biology, Vol. 178; *Phage Display: A Laboratory Manual*, C. F. Barbas III et al. eds., Cold Spring Harbor, N.Y., USA, Cold Spring Harbor Laboratory Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci. USA* 82:488-492 (1985)).

In one aspect, the viral antigen neutralizing molecules of the present invention are antibodies, which are typically selected using antibody libraries. In the following description, the invention is illustrated with reference to certain types of antibody libraries, but the invention is not limited to the use of any particular type of antibody library. Recombinant monoclonal antibody libraries can be based on immune fragments or naïve fragments. Antibodies from immune antibody libraries are typically constructed with $V_H$ and $V_L$ gene pools that are cloned from source B cells into an appropriate vector for expression to produce a random combinatorial library, which can subsequently be selected for and/or screened. Other types of libraries may be comprised of antibody fragments from a source of genes that is not explicitly biased for clones that bind to an antigen. Thus, naïve antibody libraries derive from natural, unimmunized, rearranged V genes. Synthetic antibody libraries are constructed entirely by in vitro methods, introducing areas of complete or tailored degeneracy into the CDRs of one or more V genes. Semi-synthetic libraries combine natural and synthetic diversity, and are often created to increase natural diversity while maintaining a desired level of functional diversity. Thus, such libraries can, for example, be created by shuffling natural CDR regions (Soderlind et al., *Nat. Biotechnol.* 18:852-856 (2000)), or by combining naturally rearranged CDR sequences from human B cells with synthetic CDR1 and CDR2 diversity (Hoet et al., *Nat. Biotechnol.* 23:455-38 (2005)). The present invention encompasses the use of naïve, synthetic and semi-synthetic antibody libraries, or any combination thereof.

Similarly, the methods of the present invention are not limited by any particular technology used for the display of antibodies. Although the invention is illustrated with reference to phage display, antibodies of the present invention can also be identified by other display and enrichment technologies. Antibody fragments have been displayed on the surface of filamentous phage that encode the antibody genes (Hoogenboom and Winter *J. Mol. Biol.*, 222:381 388 (1992); McCafferty et al., *Nature* 348(6301):552 554 (1990); Griffiths et al. *EMBO J.*, 13(14):3245-3260 (1994)). For a review of techniques for selecting and screening antibody libraries see, e.g., Hoogenboom, *Nature Biotechnol.* 23(9):1105-1116 (2005). In addition, there are systems known in the art for display of heterologous proteins and fragments thereof on the surface of *Escherichia coli* (Agterberg et al., *Gene* 88:37-45 (1990); Charbit et al., *Gene* 70:181-189 (1988); Francisco et al., *Proc. Natl. Acad. Sci. USA* 89:2713-2717 (1992)), and yeast, such as *Saccharomyces cerevisiae* (Boder and Wittrup, *Nat. Biotechnol.* 15:553-557 (1997); Kieke et al., *Protein Eng.* 10:1303-1310 (1997)). Other known display techniques include ribosome or mRNA display (Mattheakis et al., *Proc. Natl. Acad. Sci. USA* 91:9022-9026 (1994); Hanes and Pluckthun, *Proc. Natl. Acad. Sci. USA* 94:4937-4942 (1997)), DNA display (Yonezawa et al., *Nucl. Acid Res.* 31(19):e118 (2003)); microbial cell display, such as bacterial display (Georgiou et al., *Nature Biotech.* 15:29-34 (1997)), display on mammalian cells, spore display (Isticato et al., *J. Bacteriol.* 183:6294-6301 (2001); Cheng et al., *Appl. Environ. Microbiol.* 71:3337-3341 (2005) and co-pending provisional application Ser. No. 60/865,574, filed Nov. 13, 2006), viral display, such as retroviral display (Urban et al., *Nucleic Acids Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)).

C. Detailed Description of Preferred Embodiments

In one aspect, the present invention concerns the selection, production and use of monoclonal antibodies and antibody-like molecules neutralizing more than one subtype and/or more than one isolate of an influenza A virus, binding to a hemagglutinin (HA) antigen of the virus, but not inhibiting hemagglutination.

The virions of influenza A virus contain 8 segments of linear negative-sense single stranded RNA. The total genome length is 13600 nucleotides, and the eight segments are 2350 nucleotides; 2350 nucleotides; of 2250 nucleotides; 1780 nucleotides; 1575 nucleotides; 1420 nucleotides; 1050 nucleotides; and 900 nucleotides, respectively, in length. Host specificity and attenuation of influenza A virus have been attributed to viral hemagglutinin (H, HA), nucleoprotein (NP), matrix (M), and non-structural (NS) genes individually or in combinations of viral genes (see, e.g., Rogers et al., *Virology* 127:361-373 (1983); Scholtissek et al., *Virology* 147:287-294 (1985); Snyder et al., *J. Clin. Microbiol.* 24:467-469 (1986); Tian et al., *J. Virol.* 53:771-775 (1985); Treanor et al., *Virology* 171:1-9 (1989).

Nucleotide and amino acid sequences of influenza A viruses and their surface proteins, including hemagglutinins and neuraminidase proteins, are available from GenBank and other sequence databases, such as, for example, the Influenza Sequence Database maintained by the Theoretical Biology and Biophysics Group of Los Alamos National Laboratory. The amino acid sequences of 15 known H subtypes of the influenza A virus hemagglutinin (H1-H15) are shown in U.S. Application Publication No. 20080014205, published on Jan. 17, 2008, incorporated herein by reference in its entirety. An additional influenza A virus hemagglutinin subtype (H16) was isolated recently from black-headed gulls in Sweden, and reported by Fouchier et al., *J. Virol.* 79(5):2814-22 (2005). A large variety of strains of each H subtype are also known. For example, the sequence of the HA protein designated H5 A/Hong Kong/156/97 was determined from an influenza A H5N1 virus isolated from a human in Hong Kong in May 1997, and is shown in comparison with sequences of several additional strains obtained from other related H5N1 isolates in Suarez et al., *J. Virol.* 72:6678-6688 (1998).

The structure of the catalytic and antigenic sites of influenza virus neuraminidase have been published by Colman et al., *Nature* 303:41-4 (1983), and neuraminidase sequences are available from GenBank and other sequence databases.

It has been known that virus-specific antibodies resulting from the immune response of infected individuals typically neutralize the virus via interaction with the viral hemagglutinin (Ada et al., *Curr. Top. Microbiol. Immunol.* 128:1-54 (1986); Couch et al., *Annu. Rev. Micobiol.* 37:529-549 (1983)). The three-dimensional structures of influenza virus hemagglutinins and crystal structures of complexes between influenza virus hemagglutinins and neutralizing antibodies have also been determined and published, see, e.g., Wilson et al., *Nature* 289:366-73 (1981); Ruigrok et al., *J. Gen. Virol.* 69 (Pt 11):2785-95 (1988); Wrigley et al., *Virology* 131(2):308-14 (1983); Daniels et al., *EMBO J.* 6:1459-1465 (1987); and Bizebard et al., *Nature* 376:92-94 (2002).

According to the present invention, antibodies with the desired properties are identified from one or more antibody libraries, which can come from a variety of sources and can be of different types.

Comprehensive Human Influenza Antibody Libraries

Comprehensive human influenza antibody libraries can be created from antibodies obtained from convalescent patients of various prior influenza, seasonal outbreaks epidemics, and pandemics, including the 1968 Hong Kong flu (H3N2), the 1957 Asian flu (H2N2), the 1918 Spanish flu (H1N1), and the 2004/2005 Avian flu (H5N1). For example, see U.S. Application Publication No. 20080014205, published on Jan. 17, 2008, incorporated herein by reference in its entirety. In order to prepare such libraries, blood or bone marrow samples are collected from individuals known or suspected to have been infected with an influenza virus. Peripheral blood samples, especially from geographically distant sources, may need to be stabilized prior to transportation and use. Kits for this purpose are well known and commercially available, such as, for example, BD Vacutainer® CPT™ cell preparation tubes can be used for centrifugal purification of lymphocytes, and guanidium, Trizol, or RNAlater used to stabilize the samples. Upon receipt of the stabilized lymphocytes or whole bone marrow, RT-PCR is performed to rescue heavy and light chain repertoires, using immunoglobulin oligo primers known in the art. The PCR repertoire products are combined with linker oligos to generate scFv libraries to clone directly in frame with m13 pIII protein, following procedures known in the art.

In a typical protocol, antibodies in the human sera can be detected by well known serological assays, including, for example, by the well-known hemagglutinin inhibition (HAI) assay (Kendal, A. P., M. S. Pereira, and J. J. Skehel. 1982. *Concepts and procedures for laboratory-based influenza surveillance*. U.S. Department of Health and Human Services, Public Health Service, Centers for Disease Control, Atlanta, Ga.), or the microneutralization assay (Harmon et al., *J. Clin. Microbial.* 26:333-337 (1988)). This detection step might not be necessary if the serum sample has already been confirmed to contain influenza neutralizing antibodies. Lymphocytes from whole blood or those present in bone marrow are next processed by methods known in the art. Whole RNA is extracted by Tri BD reagent (Sigma) from fresh or RNAlater stabilized tissue. Subsequently, the isolated donor total RNA is further purified to mRNA using Oligotex purification (Qiagen). Next first strand cDNA synthesis, is generated by using random nonamer oligonucleotides and or oligo $(dT)_{18}$ primers (SEQ ID NO: 172) according to the protocol of AccuScript reverse transcriptase (Stratagene). Briefly, 100 ng mRNA, 0.5 mM dNTPs and 300 ng random nonamers and or 500 ng oligo $(dT)_{18}$ primers (SEQ ID NO: 172) in Accuscript RT buffer (Stratagene) are incubated at 65° C. for 5 min, followed by rapid cooling to 4° C. Then, 100 mM DTT, Accuscript RT, and RNAse Block are added to each reaction and incubated at 42° C. for 1h, and the reverse transcriptase is inactivated by heating at 70° C. for 15 minutes. The cDNA obtained can be used as a template for RT-PCR amplification of the antibody heavy and light chain V genes, which can then be cloned into a vector, or, if phage display library is intended, into a phagemid vector. This procedure generates a repertoire of antibody heavy and light chain variable region clones ($V_H$ and $V_L$ libraries), which can be kept separate or combined for screening purposes.

Immunoglobulin repertoires from peripheral lymphocytes of survivors of earlier epidemics and pandemics, such as the 1918 Spanish Flu, can be retrieved, stabilized, and rescued in a manner similar to that described above. For additional H1 and H3 libraries repertoires can be recovered from properly timed vaccinated locally-sourced donors. As an additional option commercially available bone marrow total RNA or mRNA can be purchased from commercial sources to produce libraries suitable for H1 and H3, and depending upon the background of donor also suitable for H2 antibody screening.

Synthetic Human-Like Repertoire

In the methods of the present invention, the synthetic human antibody repertoire can be represented by a synthetic antibody library, which can be made by methods known in the art or obtained from commercial sources. Thus, for example, a fully synthetic human repertoire is described in U.S. patent application Ser. No. 11/864,525 filed on Sep. 28, 2007, the entire disclosure of which is hereby expressly incorporated by reference. In brief, this patent application describes libraries of immunoglobulins in which predetermined amino acids have been combinatorially introduced into one or more complementarity-determining regions of the immunoglobulin of interest. Additionally, for example, a universal immunoglobulin library, including subsets of such library, are described in U.S. Patent Application Publication No. 20030228302 published on Dec. 11, 2003, the entire disclosure of which is hereby expressly incorporated by reference.

Specific sublibraries of antibody heavy and light chains with various mutations can be combined to provide the framework constructs for the antibodies of the present invention, which is followed by introducing diversity in the CDRs of both heavy and light chains. This diversity can be achieved by methods known in the art, such as, for example, by Kunkel mutagenesis, and can be repeated several times in order to further increase diversity. Thus, for example, diversity into the heavy and light chain CDR1 and CD2 regions, separately or simultaneously, can be introduced by multiple rounds of Kunkel mutagenesis. If necessary, the various Kunkel clones can be segregated by CDR lengths and/or clones lacking diversity in a targeted CDR (e.g., CDR1 or CDR3) can be removed, e.g., by digestion with template-specific restriction enzymes. Upon completion of these steps, the size of the library should exceed about $10^9$ members, but libraries with lesser members are also useful.

In a specific embodiment, both immunized antibody libraries and synthetic antibody libraries are used for identifying the neutralizing antibodies of the present invention. The two types of libraries are fundamentally different. The synthetic antibody libraries are synthesized collections of human antibodies with the predicted ability to bind antigens, while an immunized repertoire will contain sequences to specifically recognize avian H5 hemagglutinin, and/or H1, H2, or H3 hemagglutinin, as the case may be. Thus, the immunized repertoires are theoretically optimized to recognize critical components of targeted influenza subtype(s). As a result these differences the two methods produce a different set of antibodies and thus provide a more efficient approach for identifying the desired neutralizing antibodies.

Hyperimmunized Non-Human Primate Antibody Libraries

In this method, an antibody library is rescued from hyperimmunized non-human primates, such as, for example, macaque or baboons. Specifically, non-human primates are immunized with various subtypes of the influenza A virus or with various hemagglutinin (H) proteins. Animals developing titers of antibody recognizing the influenza A virus subtype or hemagglutinin they were immunized with are sacrificed and their spleens harvested. Blood or bone marrow of the immunized animals is collected, and antibodies produced are collected and amplified as described above for the comprehensive influenza antibody libraries.

Strategies for Isolating Neutralizing Antibodies of the Invention

Regardless of the type of antibody library or libraries used, antibodies with dual specificities, such as, for example, showing reactivity with two different influenza A subtypes and/or with two strains (isolates) of the same subtype, and/or with human and non-human isolates, can be discovered and optimized through controlled cross-reactive selection and/or directed combinatorial and/or mutagenic engineering.

In a typical enrichment scheme, illustrated in FIG. 1, a library including antibodies showing cross-reactivity to two targets, designated as targets A and B, are subjected to multiple rounds of enrichment (see U.S. Application Publication No. 20080014205, published on Jan. 17, 2008, incorporated herein by reference in its entirety). If enrichment is based on reactivity with target A, each round of enrichment will increase the reactive strength of the pool towards target A. Similarly, if enrichment is based on reactivity with target B, each round of enrichment will increase the reactive strength of the pool towards target B. Although this approach refers to panning, which is the selection method used when screening phage display libraries (see below), the approach is equally applicable to any type of library discussed above, other otherwise known in the art, and to any type of display technique. Targets A and B include any targets to which antibodies bind, including but not limited to various isolates, types and subtypes of influenza viruses.

Since the goal of the present invention is to identify neutralizing antibodies with multiple specificities, a cross-reactive discovery selection scheme has been developed. In the interest of simplicity, this scheme is illustrated in FIG. 2 showing the selection of antibodies with dual specificities. In this case, an antibody library including antibodies showing reactivity with two targets, targets A and B, is first selected for reactivity with one of the targets, e.g., target A, followed by selection for reactivity with the other target, e.g., target B. Each successive selection round reinforces the reactive strength of the resulting pool towards both targets. (see also U.S. Application Publication No. 20080014205, published on Jan. 17, 2008, incorporated herein by reference in its entirety). Accordingly, this method is particularly useful for identifying antibodies with dual specificity. Of course, the method can be extended to identifying antibodies showing reactivity towards further targets, by including additional rounds of enrichment towards the additional target(s). Again, if the library screened is a phage display library, selection is performed by cross-reactive panning, but other libraries and other selection methods can also be used.

A combination of the two methods discussed above includes two separate enrichment rounds for reactivity towards target A and target B, respectively, recombining the two pools obtained, and subsequent cross-reactive selection rounds, as described above (see U.S. Application Publication No. 20080014205, published on Jan. 17, 2008, incorporated herein by reference in its entirety). This approach is illustrated in FIG. 3. Just as in the pure cross-reactive selection, each round of selection of the recombined library increases the reactive strength of the resulting pool towards both targets.

In a further embodiment, illustrated in FIG. 4, first a clone showing strong reactivity with a target A, and having detectable cross-reactivity with target B is identified. Based on this clone, a mutagenic library is prepared, which is then selected, in alternating rounds, for reactivity with target B and target A respectively. This scheme will result in antibodies that maintain strong reactivity with target A, and have increased reactivity with target B (see U.S. Application Publication No. 20080014205, published on Jan. 17, 2008, incorporated herein by reference in its entirety). Just as before, selection is performed by panning, if the libraries screened are phage display libraries, but other libraries, other display techniques, and other selection methods can also be used, following the same strategy.

As discussed above, targets A and B can, for example, be two different subtypes of the influenza A virus, two different strains (isolates) of the same influenza A virus, subtypes or isolates from two different species, where one species is preferably human. Thus, for example, target A may be an isolate of the 2004 Vietnam isolate of the H5N1 virus, and target B may be a 1997 Hong Kong isolate of the H5N1 virus. It is emphasized that these examples are merely illustrative, and antibodies with dual and multiple specificities to any two or multiple targets can be identified, selected and optimized in an analogous manner.

Alternatively, if an antibody library such as the UAL that allows segregation of discrete frameworks and CDR lengths is used to find an antibody to target A, then an antigen B could be screened for and the library could be restricted to a diverse collection of similar parameters. Once an antibody to antigen B is found then chimeric or mutagenic antibodies based upon the respective A and B antibodies could be used to engineer a dual specific collection.

Phage Display

In a particular embodiment, the present invention utilizes phage display antibody libraries to functionally discover neutralizing monoclonal antibodies with multiple (including dual) specificities. Such antibodies can, for example, be monoclonal antibodies capable of neutralizing more than one influenza A virus subtype, including the H5, H7 and/or H9 subtypes, such as the H5 and H1; H5 and H2; H5 and H3; H5, H1, and H2; H5, H1, and H3; H5, H2 and H3; H1, H2 and H3, etc., subtypes, and/or more than one strain (isolate) of the same subtype.

To generate a phage antibody library, a cDNA library obtained from any source, including the libraries discussed above, is cloned into a phagemid vector.

Thus, for example, the collection of antibody heavy and light chain repertoires rescued from lymphocytes or bone marrow by RT-PCR as described above, is reassembled as a scFv library fused to m13 pIII protein. The combinatorial library will contain about more than $10^6$, or more than $10^7$, or more than $10^8$, or more than $10^9$ different members, more than $10^7$ different members or above being preferred. For quality control random clones are sequenced to assess overall repertoire complexity.

Similarly, following the initial PCR rescue of heavy and light chain variable regions from a naïve or immunized human, or hyperimmunized nonhman primate antibody library, the PCR products are combined with linker oligos to generate scFv libraries to clone directly in frame with M13 pIII coat protein. The library will contain about more than $10^6$, or more than $10^7$, or more than $10^8$, or more than $10^9$ different members, more than $10^7$ different members or above being preferred. As a quality control step, random clones are sequenced in order to assess overall repertoire size and complexity.

Antibody phage display libraries may contain antibodies in various formats, such as in a single-chain Fv (scFv) or Fab format. For review see, e.g., Hoogenboom, *Methods Mol. Biol.* 178:1-37 (2002).

Screening

Screening methods for identifying antibodies with the desired neutralizing properties have been described above.

Reactivity can be assessed based on direct binding to the desired hemagglutinin proteins.

Hemagglutinin (HA) Protein Production

Hemagglutinin (HA) proteins can be produced by recombinant DNA technology. In this method, HA genes are cloned into an appropriate vector, preferably a baculovirus expression vector for expression in baculovirus-infected insect cells, such as *Spodoptera frugiperda* (Sf9) cells.

The nucleic acid coding for the HA protein is inserted into a baculovirus expression vector, such as Bac-to-Bac (Invitrogen), with or without a C-terminal epitope tag, such as a poly-his (hexahistidine tag (SEQ ID NO: 173)). A poly-his tag provides for easy purification by nickel chelate chromatography.

In general the cloning involves making reference cDNAs by assembly PCR from individually synthesized oligos. Corresponding isolate variant HA proteins are made by either substituting appropriate mutant oligos into additional assembly PCRs or by mutagenesis techniques, such as by Kunkel mutagenesis. Two clusters of HA protein sequences exist for H5, the 1997 and 2004 subtype isolates. Therefore, a single reference protein is made for each cluster. Similarly, reference proteins are generated for 1918 Spanish flu (H1), 1958 Asian Flu (H2), 1968 Hong Kong Flu (H3), and current H1, H2, H3 isolates.

Recombinant baculovirus is generated by transfecting the above Bacmid into Sf9 cells (ATCC CRL 1711) using lipofectin (commercially available from Gibco-BRL). After 4-5 days of incubation at 28° C., the released viruses are harvested and used for further amplifications. Viral infection and protein expression are performed as described by O'Reilley et al., *Baculovirus Expression Vectors: A Laboratory Manual* (Oxford: Oxford University Press, 1994).

Expressed poly-His-tagged HA polypeptides can then be purified, for example, by $Ni^{2+}$-chelate affinity chromatography as follows. Supernatents are collected from recombinant virus-infected Sf9 cells as described by Rupert et al., *Nature* 362:175-179 (1993). A $Ni^{2+}$-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound protein. After reaching $A_{280}$ baseline again, the column is developed with a 0 to 500 mM imidazole gradient in the secondary wash buffer. One-mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged (SEQ ID NO: 174) HA polypeptide are pooled and dialyzed against loading buffer.

Alternatively, purification of an IgG-tagged (or Fc-tagged) HA polypeptide can be performed using known chromatography techniques, including, for instance, Protein A or protein G column chromatography.

As an alternative to using Sf9 cells HA proteins can also be produced in other recombinant host cells, prokaryote, yeast, or higher eukaryote cells. Suitable prokaryotes include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Various *E. coli* strains are publicly available, such as *E. coli* K12 strain MM294 (ATCC 31,446); *E. coli* X1776 (ATCC 31,537); *E. coli* strain W3110 (ATCC 27,325); and K5 772 (ATCC 53,635).

In addition to prokaryotes, eukaryotic microbes such as filamentous fungi or yeast are suitable cloning or expression hosts for vectors containing nucleic acid encoding an HA polypeptide. *Saccharomyces cerevisiae* is a commonly used lower eukaryotic host microorganism. However, a number of other genera, species, and strains are commonly available and useful herein, such as *Schizosaccharomyces pombe* (Beach and Nurse, *Nature* 290: 140 (1981); EP 139,383 published 2 May 1985); *Kluyveromyces* hosts (U.S. Pat. No. 4,943,529; Fleer et al., *Bio/Technology* 9:968-975 (1991)) such as, e.g., *K. lactis* (MW98-8C, CBS683, CBS4574; Louvencourt et al., *J. Bacteriol.* 737 (1983)), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology* 8:135 (1990)), *K. thermotolerans*, and *K. marxianus; yarrowia* (EP 402,226); *Pichia pastoris* (EP 183,070; Sreekrishna et al., *J. Basic Microbiol.* 28:265-278 (1988)); *Candida; Trichoderma reesia* (EP 244, 234); *Neurospora crassa* (Case et al., *Proc. Natl. Acad. Sci. USA* 76:5259-5263 (1979)); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.* 112:284-289 (1983); Tilburn et al., *Gene* 26:205-221 (1983); Yelton et al., *Proc. Natl. Acad. Sci. USA* 81:1470-1474 (1984)) and *A. niger* Kelly and Hynes, *EMBO J.* 4:475-479 (1985). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs* 269 (1982).

Suitable host cells for the expression of HA proteins include cells of multicellular organisms. Examples of invertebrate cells include the above-mentioned insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (HEK 293 or HEK 293 cells subcloned for growth in suspension culture (Graham et al., *J. Gen Virol.* 36:59 (1977)); Chinese hamster ovary cells/−DHFR (CHO, Urlaub and Chasin, *Proc. Natl. Acad. Sci. USA* 77:4216 (1980)); mouse sertoli cells (TM4, Mather, *Biol. Reprod.* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

Hemagglutinin (HA) Protein Panning

HA protein is immobilized on to the surface of microtiter wells or magnetic beads to pan the described above libraries. In a particular embodiment, each library is allowed to bind the H5 protein at 4 degrees for two hours and then washed extensively with cold PBS, before eluting HA specific binding clones with 0.2 M glycine-HCl buffer (pH2.5). The recovered phage is pH neutralized and amplified by infecting a susceptible host *E. coli*. Subsequently, phagemid production can be induced to repeat the enrichment of positive clones and subsequent clones isolation for triage. Upon sufficient enrichment the entire pool is transferred by infection into a non amber suppressor *E. coli* strain such as HB2151 to express soluble scFv proteins. Alternatively, the pool(s) could be subcloned into a monomeric scFv expression vector, such as pBAD, and recombinant soluble scFv proteins are expressed for in vitro analysis and characterization, as described below.

Characterization

H5 clones are first tested for binding affinity to an H5 protein produced as described above. In a particular example, binding is tested to a 2004 H5 protein (Refseq AAS65618, Isolate; A/Thailand/2(SP-33)/2004(H5N1)), and in parallel test to a 1997 H5 protein (Refseq AAF74331, Isolate; A/Hong Kong/486/97(H5N1)), but other isolates can also be used alone or in any combination. The positive clones obtained with the 2004 and the 1997 H5 proteins will fall into two broad categories: 2004 selective and 2004/1997 nonselective. The typical functional test for neutralization involves hemagglutination inhibition assays using whole virus binding to red blood cells. Due to safety concerns, alternative hemagglutination assays with recombinant protein and red blood cells are preferred. In order to eliminate the need for whole blood, the hemagglutinin binding inhibition assay can be preformed on airway epithelial cells. The binding assay can be performed in any configuration, including, without limitation, any flow cytometric or cell ELISA (cELISA) based assays. Using cELISA is advantageous in that it obviates the use of expensive flow cytometry equipment and can provide for more automated clonal assessment and greater data collection. On the other hand, flow cytometry may provide greater sensitivity, consistency, and speed.

H1 clones can be tested for binding to any H1 proteins, including binding to the current 2004 H1 and, in parallel, for binding to 1918 and 1976 proteins. The positive clones will fall into two broad categories: 2004 selective and 2004 nonselective. Once again it is critical to test for neutralization, using methodologies similar to those described above.

Other HA proteins, such as H2, H3, H5, H6, H7, H8 and H9, can be characterized in an analogous manner.

In one aspect, the antibodies of the present invention have a binding affinity for an H2, H3, H5, H6, H7, H8, or H9 HA containing influenza virus or an H1 HA containing influenza virus, such as, for example, H1/H3, H1/H5, etc. Binding affinities of the antibodies of the present invention can be determined by methods known to those of skill in the art, for example by the Scatchard analysis of Munson et al., Anal. Biochem., 107:220 (1980). In one embodiment, the binding affinity of the antibody is from about $1\times10^{-7}$ to about $1\times10^{-13}$ M, from about $1\times10^{-8}$ to about $1\times10^{-12}$ M, or from about $1\times10^{-9}$ to about $1\times10^{-11}$ M. In other embodiments, the binding affinity of the antibody is about $1\times10^{-7}$ M, about $1\times10^{-8}$ M, about $1\times10^{-9}$ M, about $1\times10^{-1\times10}$ M, about $1\times10^{-11}$ M, about $1\times10^{-12}$ M, or about $1\times10^{-13}$ M. For example, an antibody of the present invention demonstrated a binding affinity of 13 pM for an H5 HA (Vietnam/1203/04) containing influenza virus (see antibodies from survivor 2 in the Example below). Another antibody demonstrated a binding affinity of single digit nM for an H5 HA (Vietnam/1203/04) containing influenza virus (see antibodies from survivor 5 in the Example below).

Optimization

For the efficient management of influenza epidemics and pandemics, including a potential pandemic associated with human infections caused by an avian (H) virus, antibodies that effectively neutralize current isolates of the H proteins, such as the H1, H3, H5, etc. protein, as well as future mutations, are needed. In order to achieve this goal, diverse H (e.g., H1, H3, H5, etc.) neutralizing clones need to be identified that bind all known isolates of the targeted hemagglutinin subtype(s).

If desired, cross-reactivity can be further improved by methods known in the art, such as, for example, by Look Through Mutagenesis (LTM), as described in US. Patent Application Publication No. 20050136428, published Jun. 23, 2005, the entire disclosure of which is hereby incorporated by reference.

Look-through mutagenesis (LTM) is a multidimensional mutagenesis method that simultaneously assesses and optimizes combinatorial mutations of selected amino acids. The process focuses on a precise distribution within one or more complementarity determining region (CDR) domains and explores the synergistic contribution of amino acid side-chain chemistry. LTM generates a positional series of single mutations within a CDR where each wild type residue is systematically substituted by one of a number of selected amino acids. Mutated CDRs are combined to generate combinatorial single-chain variable fragment (scFv) libraries of increasing complexity and size without becoming prohibitive to the quantitative display of all variants. After positive selection, clones with improved properties are sequenced, and those beneficial mutations are mapped. To identify synergistic mutations for improved HA binding properties, combinatorial libraries (combinatorial beneficial mutations, CBMs) expressing all beneficial permutations can be produced by mixed DNA probes, positively selected, and analyzed to identify a panel of optimized scFv candidates. The procedure can be performed in a similar manner with Fv and other antibody libraries.

Mutagenesis can also be performed by walk-through mutagenesis (WTM), as described above.

Another useful mutagenic method to intentionally design cross-reactivity of the antibodies herein with more than one influenza A subtype and/or more than one isolate of the same subtype, is referred herein as "destinational" mutagenesis. Destinational mutagenesis can be used to rationally engineer a collection of antibodies based upon one or more antibody clones, preferably of differing reactivities. In the context of the present invention, destinational mutagenesis is used to encode single or multiple residues defined by analogous positions on like sequences such as those in the individual CDRs of antibodies. In this case, these collections are generated using oligo degeneracy to capture the range of residues found in the comparable positions. It is expected that within this collection a continuum of specificities will exist between or even beyond those of the parental clones. The objective of destinational mutagenesis is to generate diverse multifunctional antibody collections, or libraries, between two or more discrete entities or collections. In the case of influenza this method can be utilized to use two antibodies that recognize two distinct epitopes, isolates, or subtypes and morph both functional qualities into a single antibody. As an example, a first influenza A antibody can be specific to a Vietnam isolate of the H5 subtype and a second antibody is specific to a Thailand or Turkish isolate of the H5 subtype of the influenza A virus. To create a destinational mutagenesis library, the CDR sequences for both antibodies are first attained and aligned. Next all positions of conserved identity are fixed with a single codon to the matched residue. At non-conserved positions a degenerate codon is incorporated to encode both residues. In some instances the degenerate codon will only encode the two parental residues at this position. However, in some instances additional co-products are produced. The level of co-product production can be dialed in to force co-product production or eliminate this production dependent upon size limits or goals.

Thus, for example, if the first position of the two antibodies respectively are threonine and alanine, the degenerate codon with A/G-C- in the first two positions would only encode threonine or alanine, irrespective of the base in the third position. If, for example, the next position residues are lysine and arginine the degenerate codon A-A/G-A/G will only encode lysine or arginine. However, if the degenerate codon A/C-A/G-A/G/C/T were used then asparagine, histidine, glutamine, and serine coproducts will be generated as well.

Figure 5:
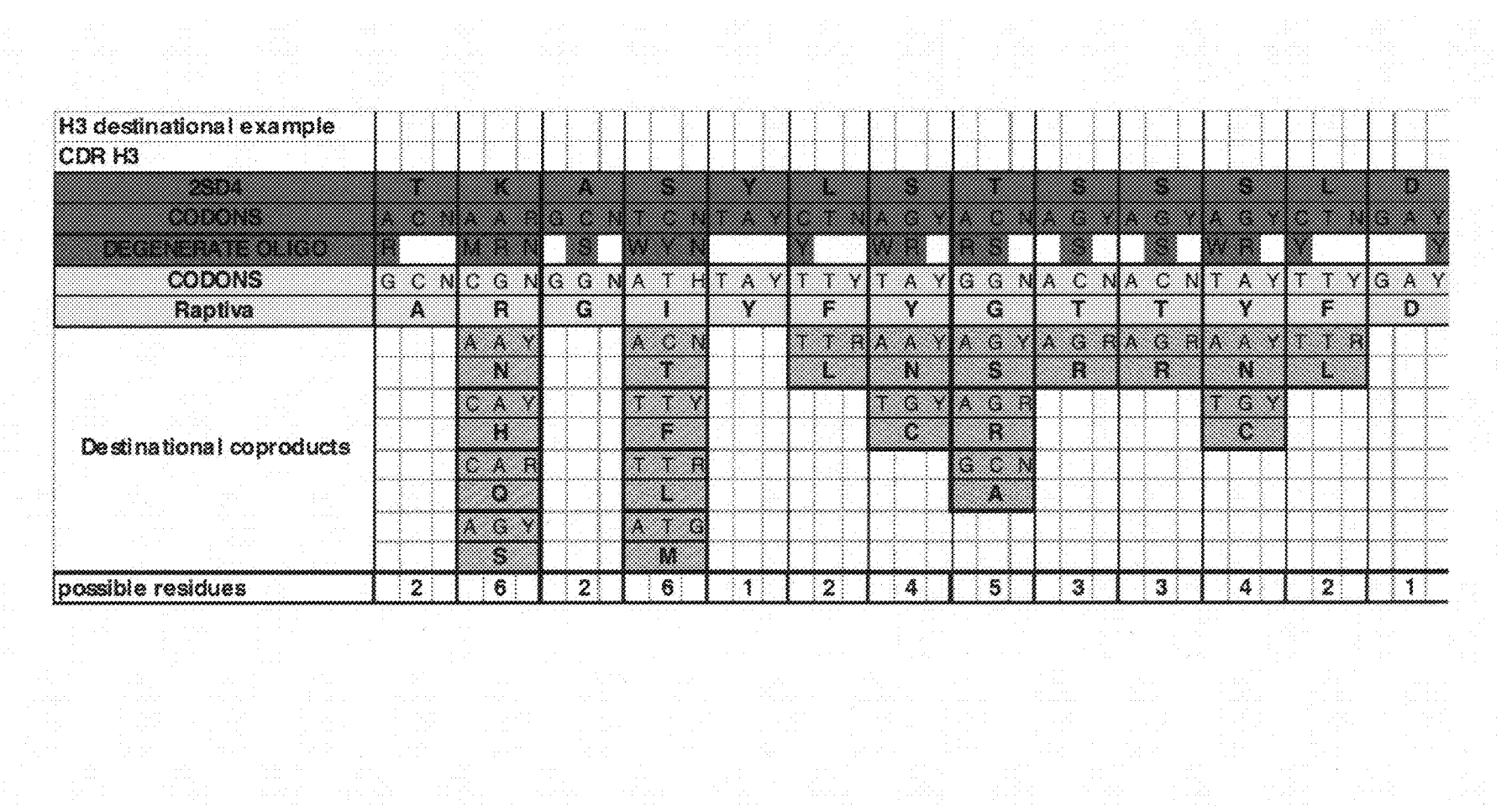

As a convenience it is simpler to use only antibodies with matched CDR lengths. One way to force this is to screen a size restricted library for the second antigen, based on the CDR length and potentially even framework restrictions imparted by the initially discovered antibody. It is noted, however, that using CDRs of equal length is only a convenience and not a requirement. It is easy to see that, while this method will be useful to create large functionally diverse libraries of influenza A virus neutralizing antibodies, its applicability is much broader. This mutagenesis technique can be used to produce functionally diverse libraries or collections of any antibody (see U.S. Application Publication No. 20080014205, published on Jan. 17, 2008 and incorporated herein by reference in its entirety). Thus, FIG. 5 is included herein to illustrate the use of the destinational mutagenesis method using CDRs of a TNF-α antibody and a CD11a antibody as the parental sequences mutagenized.

Other exemplary mutagenesis methods include targeted random mutagenesis, saturation mutagenesis and error prone PCR.

Targeted random mutagenesis (Matteuchi and Heyneker, *Nucleic Acids Research* 11: 3113-3121 (1983)) using ambiguously synthesized oligonucleotides is a technique that generates an intended codon as well as all possible codons at specific ratios, with respect to each other, at designated positions. Ambiguously synthesized oligonucleotides result in the reduced accuracy of nucleotide addition by the specific addition of non "wild type" bases at designated positions, or codons. This is typically performed by fixing the ratios of wild type and non wild type bases in the oligonucleotide synthesizer and designating the mixture of the two reagents at the time of synthesis.

Saturation mutagenesis (Hayashi et al., *Biotechniques* 17:310-315 (1994)) is a technique in which all 20 amino acids are substituted in a particular position in a protein and clones corresponding to each variant are assayed for a particular phenotype. (See, also U.S. Pat. Nos. 6,171,820; 6,358,709 and 6,361,974.)

Error prone PCR (Leung et al., *Technique* 1:11-15 (1989); Cadwell and Joyce, *PCR Method Applic.* 2:28-33 (1992)) is a modified polymerase chain reaction (PCR) technique introducing random point mutations into cloned genes. The resulting PCR products can be cloned to produce random mutant libraries or transcribed directly if a T7 promoter is incorporated within the appropriate PCR primer.

Other mutagenesis techniques are also well known and described, for example, in *In Vitro Mutagenesis Protocols*, J. Braman, Ed., Humana Press, 2001.

In the present case, one of the main goals is to engineer an antibody (or antibodies) to effectively treat current H5 (or H7 or H9) isolates as well as future mutations. To engineer an antibody with tolerances capable of recognizing mutations in new isolates H5 neutralizing clones that bind a variety of H5 isolates, including, for example, both recent 2004 isolates and previous 1997 isolates are to be identified. It is expected that if a clone is selected on a 2004 isolate it will bind/neutralize a 1997 isolate to a lesser degree. In this case the goal is to improve 1997 recognition dramatically within the context of improving (or at least maintaining) 2004 isolate binding. Therefore, selection is first done for improvements on 1997 reference protein followed by selection on the 2004 protein. Doing so provides a greater selective pressure on the new strain, while maintaining pressure on the second parameter.

Optimization can be based on any of the libraries discussed above, or any other types of libraries known in the art, alone or in any combination. In a particular embodiment, optimization can begin by screening three types of LTM libraries; triple mutagenized light chain library, triple mutagenized heavy chain library, and hextuple mutagenized (light+heavy chain) library. H5 is panned essentially as described above, although minor modifications might be desirable. For example, prior to glycine-HCl elution one can select for improved binding by increasing washing stringencies at each round by either or both of the following methods: extensive washing at RT or 37 degrees, or prolonged incubation in presence of excess soluble parent scFv. These selection modifications should improve off-rate kinetics in the resulting clones. After 3-4 rounds of selection we will sequence random clones and test for binding by ELISA. Following sequence analysis of the improved clones, all the allowable improved mutations are combined into a combinatorial beneficial mutagenesis (CBM) library to select for synergistic improvements to binding of both subtype H5 isolates. The CBM library is made by synthesizing degenerate oligo nucleotides to represent all improved and original parental residues at all positions. The resulting library is selected under increasing stringencies, similarly to LTM screening. Following sufficient selection the pool is subcloned into a pBAD expression vector to express and purify monomeric scFv protein from *E. coli* for binding and neutralization assays, described above.

H1 neutralizing antibodies can be optimized in an analogous manner. In this case one can select and optimize using any reference protein sequences from 1918, 1976, and current as either a starting point or destination.

In addition, intertype recognition is tested with the neutralizing antibody clones. An example of intertype recognition is coincidental or engineered H1 binding from an H5 sourced or optimized clone.

The handling of antibody libraries, such as libraries from various donors or characterized by reactivity to different isolates of subtypes of a virus, including but not limited to influenza viruses, can be greatly facilitated by applying unique barcodes distinguishing the various antibody collections. The barcodes preferably are selected such that they are capable of propagating along with the clone(s) labeled.

Thus the barcodes can be non-coding DNA sequences of about 1-24 non-coding nucleotides in length that can be deconvoluted by sequencing or specific PCR primers. This way, a collection of nucleic acids, such as an antibody repertoire, can be linked at the cloning step.

In another example, the barcodes are coding sequences of silent mutations. If the libraries utilize restriction enzymes that recognize interrupted palidromes (e.g. Sfi GGCCNNNNNG-GCC (SEQ ID NO: 175)), distinct nucleotides can be incorporated in place of the "N's" to distinguish various collections of clones, such as antibody libraries. This barcoding approach has the advantage that the repertoire is linked at the amplification step.

In a different example, the barcodes are coding sequences that encode immunologically distinct peptide or protein sequences fused to phage particles. Examples include, for example, epitope (e.g. Myc, HA, FLAG) fusions to pIII, pVIII, pVII, or pIX phages. The epitopes can be used singly or in various combinations, and can be provided in cis (on the library-encoding plasmid) or in trans (specifically modified helper phage) configuration.

Other examples of possible barcodes include, without limitation, chemical and enzymatic phage modifications (for phage libraries) with haptens or fluorescent chromophores. Such tags are preferred for a single round of selection.

While barcoding is illustrated herein for distinguishing antibody libraries, one of ordinary skill will appreciate that the described approaches are broadly applicable for uniquely labeling and distinguishing nucleic acid molecules and collections of nucleic acids in general.

Epitope Mapping of Neutralizing Antibodies

Once neutralizing antibodies with the desired properties have been identified, it might be desirable to identify the dominant epitope or epitopes recognized by the majority of such antibodies. Methods for epitope mapping are well known in the art and are disclosed, for example, in Morris, Glenn E., *Epitope Mapping Protocols*, Totowa, N. J. ed., Humana Press, 1996; and *Epitope Mapping: A Practical Approach*, Westwood and Hay, eds., Oxford University Press, 2001.

Epitope mapping concerns the identification of the epitope to which an antibody binds. There are many methods known to those of skill in the art for determining the location of epitopes on proteins, including crystallography analysis of the antibody-antigen complex, competition assays, gene fragment expression assays, and synthetic peptide-based assays (see for example, in Chapter 11 of Harlow and Lane, Using Antibodies, a Laboratory Manual, Cold Spring Harbor Laboratory Press, Cold Spring Harbor, N.Y., 1999; U.S. Pat. No. 7,332,579, each of which is incorporated herein by reference in its entirety). An antibody binds "essentially the same epitope" as a reference antibody, when the two antibodies recognize epitopes that are identical or sterically overlapping epitopes. A commonly used method for determining whether two antibodies bind to identical or sterically overlapping epitopes is the competition assay, which can be configured in all number of different formats, using either labeled antigen or labeled antibody. Usually, an antigen is immobilized on a 96-well plate, and the ability of unlabeled antibodies to block the binding of labeled antibodies is measured using radioactive or enzyme labels.

Production of Neutralizing Antibodies

Once antibodies with the desired neutralizing properties are identified, such antibodies, including antibody fragments can be produced by methods well known in the art, including, for example, hybridoma techniques or recombinant DNA technology.

In the hybridoma method, a mouse or other appropriate host animal, such as a hamster, is immunized to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these cell lines, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.* 133: 3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

Recombinant monoclonal antibodies can, for example, be produced by isolating the DNA encoding the required antibody chains and co-transfecting a recombinant host cell with the coding sequences for co-expression, using well known recombinant expression vectors. Recombinant host cells can be prokaryotic and eukaryotic cells, such as those described above.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.* 151:2296 (1993); Chothia et al., *J. Mol. Biol.* 196:901 (1987)). It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences.

In addition, human antibodies can be generated following methods known in the art. For example, transgenic animals (e.g., mice) can be made that are capable, upon immunization, of producing a full repertoire of human antibodies in the absence of endogenous immunoglobulin production. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669, 5,589,369 and 5,545,807.

Neutralizing Antibodies

A number of neutralizing antibodies have been identified through the use of the techniques described herein, including those described in the Examples below. In one aspect, the present invention provides neutralizing antibodies that bind to a hemagglutinin protein epitope. In one embodiment, the neutralizing antibody binds to at least one epitope on the HA1 subunit of the hemagglutinin protein. In another embodiment, the neutralizing antibody binds to at least two, at least three, at least four, at least five, or at least six epitopes on the HA1 subunit of the hemagglutinin protein. In a preferred embodiment, the neutralizing antibody of the present invention binds to an epitope that is substantially the same as the epitope for (i) an antibody comprising a heavy chain amino acid sequence shown as SEQ ID NO: 4 and a light chain amino acid sequence shown as SEQ ID NO:71 (antibody 1 in the Example below and as shown in Table 1); (ii) an antibody antibodies do not prevent the binding of an influenza A virus to a target cell to be infected. In another embodiment, the anti-hemagglutinin antibody does not prevent the receptor binding site on the globular head region of the HA of an influenza A virus from attaching to a target cell to allow hemagglutinin activity of HA to occur.

TABLE 1

Neutralizing Abs

| Antibody | Heavy chain SEQ ID NO: | Light chain SEQ ID NO: | Neutralizes |
|---|---|---|---|
| 1 | QVQLVQSGAEVKKPGSSVRVSCKTSGGTFSSYAVTWV RQAPGQGLEWMGGIIGMFGTTNYAQKFQGRLTITADE MTSTAYMELSSLRSEDTAVYYCARGSYYYETTLDYW GRGTL (SEQ ID NO: 4) | ETTLTQSPGTLSLSPGERATLSCRVSQSVSSNYLAWYQQKP GQAPRLLIYGASSRATGIPDRFSGSGSGTDFTLTISRLEPEDF AVYYCQQYGTSPRAFGHGTKVEIKRTV (SEQ ID NO: 71) | H5, H1 |
| 2 | QVQLVQSGAEVKKPGSSVKVSCKTSGGTFSSYAVTWV RQAPGQGLEWMGGIIGMFGTTNYAQKFQGRVTITADE LTSTAYMELSSLRSEDTAVYYCARGSYYYESSLDYWG RGTL (SEQ ID NO: 45) | ETTLTQSPATLSVSPGERATLSCRASQSVSRNLAWYQQKPG QAPRLLIYGASSRATGIPDRFSGSGSGTDFTLTISRLEPEDFA VYYCQQYGSSSITFGQGTRLEIKRTV (SEQ ID NO: 140) | H5, H1 |
| 3 | EVQLVQSGAEVKKPGSSVKVSCKTSGGTFSSYAVTWV RQAPGQGLEWMGAIIGMFGTTNYAQKFQGRVTITADE LTSTAYMELSSLRSDDTAVYYCARGSYYYESSLDYWG KGTL (SEQ ID NO: 9) | QSVLTQPPSVSGAPGQRVTISCGGSRSNIGAGYDVHWYQQ FPGTAPKVVIYGNNNRPSGVPDRFSGSKSGTSASLAITGLQ AEDEANYYCQSYDTNLGGSIFGGGTQVTVL (SEQ ID NO: 81) | H5, H1 |
| 4 | QVQLQESGPGLVKPSETLSLTCTVSGYSFDSGYYWGW LRQPPGKGLEWIGSIYHSRNTYYNPSLKSRVTISVDTSK NQFSLQLSSVTAADTAVYYCARGTWYSSNLRYWFDP WGKGTL (SEQ ID NO: 61) | NFMLTQPHSVSESPGKTVTISCTGSGGNIARNYVQWYQQR PGSAPVTVILEDDKRPSGIPDRFSGSIDRSSNSASLTISGLRTE DEALYYCQSYDDSDLVVFGGGTKLT (SEQ ID NO: 158) | H5 |
| 5 | QVQLQESGPGLVKPSETLSLTCTVSGYSFDSGYYWGW LRQPPGKGLEWIGSIYHSRNTYYNPSLKSRVTISVDTSK NQFSLQLSSVTAADTAVYYCARGTWYSSNLRYWFDP WGKGTL (SEQ ID NO: 61) | NFMLTQPHSVSESPGKTVTISCTGSSGSIASNYVQWYQQRP GSAPTTVIYEDYQRPSGVPDRFSGSIDSSSNSASLTISGLKTE DEADYYCQSYDDSDHLIFGGGTKLTVL (SEQ ID NO: 159) | H5 |
| 6 | QVQLQESGPGLVKPSETLSLTCTVSGYSFDSGYYWGW LRQPPGKGLEWIGSIYHSRNTYYNPSLKSRVTISVDTSK NQFSLQLSSVTAADTAVYYCARGTWYSSNLRYWFDP WGKGTL (SEQ ID NO: 61) | QSVLTQPPSASGTPGQRVTISCSGSSSNIGSNTVNWYKQLP GTAPRLLIYSNDQRPSGVPDRFSGSKSGTSASLAISGLQSED EANYYCAAWDDSLSGWVFGGGTKLTVL (SEQ ID NO: 160) | H5 | comprising a heavy chain amino acid sequence shown as SEQ ID NO:45 and a light chain amino acid sequence shown as SEQ ID NO:140 (antibody 2 in the Example below and as shown in Table 1); (iii) an antibody comprising a heavy chain amino acid sequence shown as SEQ ID NO:9 and a light chain amino acid sequence shown as SEQ ID NO:81 (antibody 3 in the Examples below and as shown in Table 1); (iv) an antibody comprising a heavy chain amino acid sequence shown as SEQ ID NO:61 and a light chain amino acid sequence shown as SEQ ID NO:158 (antibody 4 in the Example below and as shown in Table 1); or (v) an antibody comprising a heavy chain amino acid sequence shown as SEQ ID NO:61 and a light chain amino acid sequence shown as SEQ ID NO:159 (antibody 5 in Table 1); (vi) an antibody comprising a heavy chain amino acid sequence shown as SEQ ID NO:61 and a light chain amino acid sequence shown as SEQ ID NO:160 (antibody 6 in Table 1). This is summarized in Table 1 below.

In some embodiments, the antibodies of the present invention neutralize viruses containing H5 and/or H1. In other embodiments, the antibodies neutralize both H5 and H1. In one embodiment, the antibodies of the present invention do not prevent hemagglutination. In other embodiments, the Based on the experiments described in the Examples below, a number of H5 anti-hemagglutinin antibody heavy chain/light chain pairings were identified. As shown in Table 2, column 1 provides the heavy chain amino acid sequence, column 2 provides the corresponding SEQ ID NO: for the heavy chain sequence, column 3 provides the amino acid sequence for those light chains that pair with the heavy chains in the same row, and column 4 provides the corresponding SEQ ID NOS: for the light chain sequence. For example, the heavy chain sequence shown as SEQ ID NO:1 pairs with the light chain sequence shown as SEQ ID NO:68, SEQ ID NO:2 pairs with SEQ ID NO:69, etc. In some embodiments, a heavy chain can pair with more than one light chain. For example, the heavy chain sequence shown as SEQ ID NO:6 pairs with either the light chain sequence shown as SEQ ID NO:74 or the light chain sequence shown as SEQ ID NO:75; or the heavy chain sequence shown as SEQ ID NO:7 pairs with one of (i) the light chain sequence shown as SEQ ID NO:75, (ii) the light chain sequence shown as SEQ ID NO:76, or (iii) the light chain sequence shown as SEQ ID NO:77.

In one embodiment, the neutralizing antibodies of the present invention contain at least one heavy chain polypeptide containing an amino acid sequence shown in Table 2, and/or at least one light chain polypeptide containing an amino acid sequence shown in Table 2.

TABLE 2

| Heavy Chain Sequence | SEQ ID NO | Light Chain Sequence | SEQ ID NO |
|---|---|---|---|
| EVQLVQSGTEVKKPGSSVKLSCKASGGTFSSY AVTWVRQAPGQGLEWMGGIIGMFGTTNYAQ KFQGRLTITADEMTSTAYMELSSLRSEDTAVY YCARGSYYYETTLDYWGRGTM | 1 | QSALTQPASVSGSPGQSITISCTGTSSDFG GSNHVSWYQQHPGKAPKLIIYDVSDRPS GVSNRFSGSKSGNTASLTVSGLQAEDEA HYYCSSYAGSNNFVFGTGTKVTVL | 68 |
| EVQLVQSGAEVKKPGSSVRVSCKTSGGTFSSY AVTWVRQAPGQGLEWMGGIIGMFGTTNYAQ KFQGRLTITADEMTSTAYMELSSLRSEDTAVY YCARGSYYYETTLDYWGRGTM | 2 | ETTLTQSPGTLSLSPGERATLSCRASQTVS SSYLAWYRQKPGQAPRLLIYGTSSRATGI PDRFSGSGSGTDFTLTISRLEPEDFAVYYC QQYGNSRVTFGPGTKVDIKRTV | 69 |
| QVQLQQSGAEVKKPGSSVRVSCKTSGGTFSSY AVTWVRQAPGQGLEWMGGIIGMFGTTNYAQ KFQGRLTITADEMTSTAYMELSSLRSEDTAVY YCARGSYYYETTLDYWGQGTM | 3 | EIVMTQSPGTLSLSPGERATLSCRASQSLS GSNVAWYQQKFGQAPRLLIHGASKRAA GIPDRFSGSGSGTDFTLTISRLQPDDYAVY YCQQYGTKPFTFGQGSKLEIKRTV | 70 |
| QVQLQSGAEVKKPGSSVRVSCKTSGGTFSSY AVTWVRQAPGQGLEWMGGIIGMFGTTNYAQ KFQGRLTITADEMTSTAYMELSSLRSEDFAVY YCARGSYYYETTLDYWGRGTL | 4 | ETTLTQSPGTLSLSPGERATLSCRVSQSVS SNYLAWYQQKPGQAPRLLIYGASSRATG IPDRFSGSGSGTDFTLTISRLEPEDFAVYY CQQYGTSPRAFGHGTKVEIKRKTV | 71 |
| QVQLQQSGAEVKKPGSSVRVSCKTSGGTFSSY AVTWVRQAPGQGLEWMGGIIGMFGTTNYAQ KFQGRLTITADEMTSTAYMELSSLRSEDTAVY YCARGSYYYETTLDYWGKGTL | 5 | QSALTQPPSASGSPGQSVTISCTGASSDIG GYKSVSWYQQHPGKAPKLIIYDVTERPS GVPDRFSASKSGNTASLTVSGLQAEDEA DYYCSSYGGSNNLVVFGGGTKVTVL | 72 |
|  |  | DIQMTQSPSSVSASVGDRVTITCRASQGIS SWLAWYQQKPGKAPKLLIYAASTLQRG VPSRFSGSGSGTDFTLTINSLQPEDFATYY CQQYNSYPLTFGGGTKVEIKR | 73 |
| EVQLQSGAEVKKPGSSVRVSCKTSGGTFSSY AVTWVRQAPGQGLEWMGGIIGMFGTTNYAQ KFQGRLTITADEMTSTAYMELSSLRSEDTAVY YCARGSYYYETTLDYWGKGTL | 6 | EIVLTQSPGTLSLSPGERATLSCRASQSVS NNYLAWYQQKPGQAPRLLIYGASSRATG IPDRFSGSGSGTDFTLTISRLEPEDFAVYY CQQYGRSPRTFGQGTKVEIKRT | 74 |
|  |  | ETTLTQSPGTLSPGERATLSCRASQSLG GANLGWYQQKFGQPPRLLIYGASSRATG VPDRFSGSGSGTDFALTISRLEPEDFAVY YCQQYGSKPYTFGQGTKLEIKRTV | 75 |
| EVQLVQSGAEVKKPGSSVRVSCKTSGGTFSSY AVTWVRQAPGQGLEWMGGIIGMFGTTNYAQ KFQGRLTITADEMTSTAYMELSSLRSEDTAVY YCARGSYYYETTLDYWGQGTL | 7 | ETTLTQSPGTLSLSPGERATLSCRASQSLG GANLGWYQQKFGQPPRLLIYGASSRATG VPDRRSGSGSGTDFALTISRLEPEDFAVY YCQQYGSKPYTFGQGTKLEIKRTV | 75 |
|  |  | ETTLTQSPATLSVSPGERATLSCRASQSVS TNLAWYQQKPGQAPRLLIHGASTRATGIP ARFSGSGSGTEFTLTISSLQSEDSAVYYCQ QHNNWPPVTFGRGTKVEIKRTV | 76 |
|  |  | ETTLTQSPATLSVSPGERATLSCRASQSVS RNLAWYQQKPGQAPRLLIYGASSRATGIP DRFSGSGSGTDFTLTISRLEPEDFAVYYC QQYGSSSITFGQGTRLEIKRTVV | 77 |
| EVQLVQSGAEVKKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGRGTL | 8 | QSVLTQPPSASGAPGQRVTISCRGSSSNIG AGYDVHWYQQLPGRAPKLLIYGNSNRPS GVPARFSGSKSATSASLAITGLQAEDEAD YYCQSYDSSLSGVVFGGGTKLTVL | 78 |
|  |  | EIVMTQSPATLSVSPGERAILSCRASRSVS TNLAWYQQKPGQAPRLLIYGASTRATGIP DRFSGSGSGTDFTLTISRLEPEDFAVYYC QQYGSSPNFGGGTKVEIKR | 79 |
| EVQLVQSGAEVKKPGSSVKVSCKTSGGTFSSY AVTWVRQAPGQGLEWMGAIIGMFGTTNYAQ KFQGRVTITADELTSTAYMELSSLRSDDTAVY YCARGSYYYESSLDYWGKGTL | 9 | EIVMTQSPGTLSLSPGERATLSCRASQSVP NRYIAWYQQKPGQAPRLLIYGASSRATGI PDRFSGSGSGPDFTLTISRLEPEDFAVYYC QQYGRSPQTFGQGTKLEIKGTV | 80 |
|  |  | QSVLTQPPSVSGAPGQRVTISCGGSRSNIG AGYDVHWYQQFPGTAPKVVIYGNNNRP SGVPDRFSGSKSGTSASLAITGLQAEDEA NYYCQSYDTNLGGSIFGGGTQVTVL | 81 |
|  |  | EIVMTQSPGTLSVSPGDAATLSCRASRNI NNNLAWYQQTPGQAPRLLIYGASTRATG | 82 |

TABLE 2-continued

| Heavy Chain Sequence | SEQ ID NO | Light Chain Sequence | SEQ ID NO |
|---|---|---|---|
| | | LPARFTGSGSGTEFTLTISSLQSEDFAVYY CQQYNNWPRTFGQGTKVEIKR | |
| EVQLVQSGTEVKKPGSSVKVSCKVSGGTFSSY AVTWVRQAPGQGLEWMGAIIGMFGTTNYAQ KFQGRVTITADELTSTAYMELSSLRSDDTAVY YCARGSYYYESSLDYWGGGTT | 10 | ETTLTQSPGTLSLSPGERATLSCRASQIVD SSYLAWYQHRPGQAPRILIYGASSRAPGV PDRFSGSGSGTDFTLTISRLEPEDFAVYYC QQYAVSPRTFGQGTKVEIKRTV | 83 |
| EVQLVQSGAEVKKPGSSVKVSCKTSGGTFSSY AVTWVRQAPGQGLEWMGAIIGMFGTTNYAQ KFQGRVTITADELTSTAYMELSSLRSDDTAVY YCARGSYYYESSLDYWGQGTL | 11 | EIVLTQSPGTLSLSPGDRATLSCRASQSLG TNYLAWYQQKPGQAPRLLIYGASSRATG IPDRFSGSGSGTDFTLIISRLEPEDFAVYYC QQYGRSPQKFGQGTKVEIKRTV | 84 |
| | | QSVLTQPPSASGTPGQRVTISCSGSSSNIG SNYVYWYQQLPGTAPKLLIYRNNQRPSG VPDRFSGSKSGTSASLATSGLRSEDEANY YCAAWDDSLSGWVFGGGTKLTVL | 85 |
| | | EIVMTQSPATLSVSPGERAILSCRASRSVS TNLAWYQQKPGQAPRLLIYGASTRATGIP DRFSGSGSGTDFTLTISRLEPEDFAVYYC QQYGSSPNFGGGTKVEIKR | 86 |
| EVQLVQSGAEVKKPGSSVKVSCKTSGGTFSSY AVTWVRQAPGQGLEWMGAIIGMFGTTNYAQ KFQGRVTITADELTSTAYMELSSLRSDDTAVY YCARGSYYYESSLDYWGQGTM | 12 | DIQMTQSPSSVSASVGDRVTITCRASQGIS SWLAWYQQKPGKAPKLLIYAASSLQSGV PSRFSGSGSGTDFTLTISSLQPEDVATYYC QKYNSAPRTFGQGTKVEIKR | 87 |
| QVQLVQSGAEVKKPGSSVKVSCKTSGGTFSSY AVTWVRQAPGQGLEWMGAIIGMFGTTNYAQ KFQGRVTITADELTSTAYMELSSLRSDDTAVY YCARGSYYYESSLDYWGQGTM | 13 | DIQLTQSPSSLSASVGDRVTITCRASQSIS NYLNWYQQKPGKAPKLLIYAASSLQSGV PSRFSGSGSGTDFTLTISSLQPEDSATYYC QQSHSTPRTFGQGTKLEIKRTV | 88 |
| | | QAVLTQPPSASGTPGQRVTISCSGSSSNIG TNTVNWYQQLPGTAPKLLIYRNIQRPSGV PDRFSGSKSGTSASLAISGLQSEDEADYY CAAWDDSLNGYVFGTGTLKTVL | 89 |
| EVQLVQSGAEVKKPGSSVKVSCKTTGGTFSSY AVTWVRQAPGQGLEWMGGIIGMFGTTNYAQ KFQGRVTITADEMTSTAYMELSSLRSEDTAVY YCARGSYYYESSLDYWGQGTL | 14 | EIVLTQSPGTLSLSPGEKATLSCRASQSVS NTYLAWYQQKPGQAPRLLLYGASSRAPG IPDRFSGSGSGTDFTLTISRLEAEDFAVYF CQQYAGSPRTFGQGTKVEIKRTV | 90 |
| | | EIVLTQSPGSLSLSPGERATLSCRASQSVS HGYLAWYQQKPGQAPRFLIYGASSRPTGI PDRFRGSGSGTDFTLTISSLEPEDSAVYYC QQYSTSPLTFGGGTKVEIKRTV | 91 |
| | | PELTQPPSASGTFGQRVTISCSGSSSNIGSN YVYWYQQLPGTAPKLLIYRNNQRPSGVP DRFSGSKSGTSASLAISGLRSEDEADYYC AAWDDSLSGWVFGGGTKLTVL | 92 |
| EVQLVQSGAEVKKPGSSVLVSCKTTGGTFSSY AVTWVRQAPGQGLEWMGGIIGMFGTTNYAQ KFQGRVTITADEMTSTAYMELSSLRSEDTAVY YCARGSYYYESSLDYWGQGTM | 15 | ETTLTQSPGTLSLSPGERATLSCRASQIVD SSYLAWYQHRPGQAPRILIYGASSRAPGV PDRFSGSGSGTDFTLTISRLEPEDFAVYYC QQYGSPPRTFGQGTKVEIKRTV | 93 |
| EVQLVQSGAEVKKPGSSVKVSCKTSGGTFSSY AVTWVRQAPGQGLEWMGAIIGMFGTTNYAQ KFQGRVTLTADELTSTAYMELSSLRSEDTAVY TCARGSYYYESSLDYWGKGTL | 16 | QSVLTQPPSTSGTPGQRVTISCSGSSSNIG RKTVNWYQQLPGTAPKLLIYNDNQRPSG VPDRFSGSKAGTSASLAISGLQSEDEADY VCAVWDDSLNAWVFGGGTKLTVL | 94 |
| EVQLVQSGAEVKKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGKGTM | 17 | DVVMTQSPLSLPVTPGEPAAISCRSSQSLL HSDGNNYLDWYLQKPGQSPHLLIYLGSN RASGVPDRFSGSGSGTDFELKISRVEAED AGVYYCMQASQTPRTFGQGTKLELKRTV | 95 |
| EVQLVLSGAEVKKPGASVKVSCKASGGAFSS YAVTWVRQAPGQGLEWMGGIIGMFGTTNYA QKFQGRVTITADELTSTAYMELSSLRSEDTAV YYCARGSYYYESSLDYWGQGTM | 18 | HVILTQPPSVSVAPGMTARMTCGGDNVG RRNVHWYQQKPGQAPVLVVYDDGGRPS AIPARFSGSKSGNTATLIISRVEAGDEADY YCQMWHSSGDQWVFGGGTLKTVL | 96 |
| EVQLVQSGAEVKKPGSSVKVSCKTSGGTFSSY AVTWVRQAPGQGLEWMGGIIGMFGTTNYAQ KFQGRVTMTADEMTSTAYMELSSLRSEDTAV YYCARGSYYYESSLDYWGKGTL | 19 | ETTLTQSPGTLSLSPGERATLSCRASQSISP NYLAWYQQRPGQAPRLLIYGASKRATGI PDRFSGSGSGTDFTLTISSLEPEDSAVYYC QHQGFGQGTKVEIKRTV | 97 |

TABLE 2-continued

| Heavy Chain Sequence | SEQ ID NO | Light Chain Sequence | SEQ ID NO |
|---|---|---|---|
| EVQLVQSGAEVKKPGSSVKVSCKTSGGTFSSY AVTWVRQAPGQGLEWMGGIIGMFGTTNYAQ KFQGRVTITADEMTSTAYMELSSLRSEDTAVY YCARGSYYYESSLDYWGRGTL | 20 | QSVLTQPPSASGTPDQRVTISCSGSGSNIG SNYVYWYQQLPGAAPKLLMSRNNQRPS GVPDRFSGSKSGTSASLAISGLQSEDEAD YYCAAWDDSLTGYVFGTGTKLTVL | 98 |
| EVQLVQSGAEVKKPGSSVKVSCKTSGGTFSSY AVTWVRQAPGQGLEWMGGIIGMFGTTNYAQ KFQGRVTITADEMTSTAYMELSSLRSEDTAVY YCARGSYYYESSLDYWGRGTM | 21 | SYVLTQPPSVSVAPGKTARITCGGKNIGS KSVHWYQQKSGQAPVLVIYGDSDRPSGI PERFSGSNSGNTATLTISGVEAEDEADYY CQVWDNTSDHAGVFGGGTKVTVL | 99 |
| EVQLVQSGAEVKKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGQGTL | 22 | QSVLTQPPSASGTPGQRVTISCSGSSSNIG SNYVYWYQQLPGTAPKLLIYRNNQRSSG VPDRFSGSKSGTSASLAISGLRSEDEADY YCAAWDDSLSGLFGGGTKLTVL | 100 |
| | | QSVLTQPPSVSAAPRQSVTISCSGTTSNIG NNPVSWYQQFPGRAPNLLIYYNDVVPSG VSDRFSASKAGTSASLAISRLQSEDEADY YCATWDDSLSAWVFGGGTQLTVL | 101 |
| | | QAVLTQPPSASGTPGQRVTISCSGSSSNIG SNYVYWYQQLPGTAPKLLIYSNNQRPSG VPDRFSGSKSGTSASLVISGLQSEDETDY YCAAWDDSLNGWVFGGGTKLTVL | 102 |
| EVQLVQSGAEVQKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGQGTL | 23 | QSALTQPPSASGSPGQSVTITCAGASSDL GDYKSVSWYQQHPGKAPKLIIYDVIKRP AGVPDRFSASKSGNTASLTVSGLQAEDE ADYYCSSYAGSNNIVIFGGGTKLTVL | 103 |
| EVQLVQSGAEVKKPGSSVKVSCKTSGGTFSSY AVTWVRQAPGQGLEWMGGIIGMFGTTNYAQ KFQGRVTITADELTSTAYMELSSLRSEDTAVY YCARGSYYYESSLDYWGQGTL | 24 | ETTLTQSPGTLSLSPGERATLSCRASQGID RKYLAWYQRKHGQAPRLLIYGASNRAT GIPDRFSGSGSGTDFTLTISRLEPEDFAVY YCQQYADSFVSFGQGTKLEIKRTV | 104 |
| EVQLVQSGAEVKKPGSSVKVSCKASGGTFSSY AISWVRQAPGQGLEWMGAIIGMFGTTNYAQK FQGRVTIADELTSTAYMELSSLRSDDTAVYY CARGSYYYESSLDYWGQGTL | 25 | DIQLTQSPSTLSASVGDRVTITCRASQSIS RWLAWYQQKPGKIPKLLIYEASNLQSGV PSRFSGSGSGTEFTLTISSLQPDDFATYYC QQYKSDFLVTFGPGTKVDIKRTV | 105 |
| EVQLVQSGAEVKKPGSSVKVSCKTSGGTFSSY AVTWVRQAPGQGLEWMGAIIGMFGTTNYAQ KFQGRVTLTADQLTSTAYMELSSLRSEDTAVY YCARGSYYYESSLDYWGRGTL | 26 | QSVLTQPPSVSGAPGQKITISCTGSSSNIGT GYDVHWYQQLPGRAPRLLISADANRPSG VPDRFSASKSGTSASLAITGLQAEDEADY YCQSYDTRLGGSIFGGGTQLTVL | 106 |
| EVQLVQSGAEVKKPGSSVKVSCKTSGGTFSSY AVTWVRQAPGQGLEWMGAIIGMFGTTNYAQ KFQGRVTLTADELTSTAYMELSSLRSDDTAVY YCARGSYYYESSLDYWGKGTL | 27 | EIVMTQSPGTLSVSPGDAATLSCRASRNI NNNLAWYQQTPGQAPRLLIYGASTRATG LPARFTGSGSGTEFTLTISSLQSEDFAVYY CQQYNNWPRTFGQGTKVEIKR | 107 |
| EVQLVQSGAEVKKPGSSVKVSCKTSGGTFSSY AVTWVRQAPGLGLEWMGAIIGMFGTTNYAQ KFQGRVTLTADELTSTAYMELSSLRSDDTAVY YCARGSYYYESSLDYWGKGTT | 28 | QSVLTQPPSVSAAPGQEVTITCSGSGANIG NNYVSWYQQVPGTAPKLVIYDNNRRPSG IPDRFSGSKSGTSATLGITGLQTGDEADY YCGTWDSSLSAVVFGGGTKVTVL | 108 |
| EVQLVQSGAEVKKPGSSVKVSCKTSGGTFSSY AVTWVRQAPGQGLEWMGGIIGMFGTTNYAQ KRQGRVTITADELTSTAYMELSSLRSEDTAVY YCARGSYYYESSLDYWGKGTL | 29 | QAVLTQPPSASGTPGQTVTISCSGVTSNIG NNYVYWYQQLPGTAPRLLIYSNNQRPSG VPDRFSGSKSGTSASLAISGLRSEDEADY YCSAWDDSLRENLFGTGTQLTVL | 109 |
| EVQLVQSGAEVKKPGSSVLVSCKTSGGTFSSY AVTWVRQAPGQGLEWMGAIIGMFGTTNYAQ KFQGRVTLTADELTSTAYMELSSLRSEDTAVY YCARGSYYYESSLDYWGRGTM | 30 | QAVLTQPPSASGTPGQRVTISCSGSSSNFG MNAVNWYQQLPGTAPKLLMYSNSKRPS GVPDRFSGSKSGTSASLAISGLQSEDEAD YYCSAWDDNLNGWVFGGGTKVTVL | 110 |
| EVQLVQSGAEVKKPGSSVKVSCKTSGGTFSSY AVTWVRQAPGQGLEWMGAIIGMFGTTNYAQ KFQGRVTITADELTSTAYMELSSLRSDDTAVY YCARGSYYYESSLDYWGKGTMVTVS | 31 | QAVLTQPPSASGTPGQRVTISCSGSSSNIG SNTVNWYQQLPGTAPKLLIYRNNQRPSG VPDRFSGSKSGTSASLAISGLQSEDEADY YCATWDDSLTSVVFGGGTKVTVL | 111 |
| QMQLVQSGAEVLLPGSSVKVSCKTSGGTFSS YAVTWVRQAPGQGLEWMGAIIGMFGTTNYA QKFQGRVTITADELTSTAYMELSSLRSDDTAV YYCARGSYYYESSLDYWGKGTM | 32 | ETTLTQSPSSLSASIGDRITIACQASQDIRN RLNWYLQRPGKAPQLLIYDASNLETGVP SKFAGRGSGTDFTLTISSLQPEDIGTYFCQ QYGDLSPLTFGGGTKVDIRRTV | 112 |

TABLE 2-continued

| Heavy Chain Sequence | SEQ ID NO | Light Chain Sequence | SEQ ID NO |
|---|---|---|---|
| QMQLVQSGAEVKKPGSSVKVSCKTSGGTFSSYAVTWVRQAPGQGLEWMGAIIGMFGTTNYAQKFQGRVTLTADELTSTAYMELSSLRSEDTAVYYCARGSYYYESSLDYWGQGTLVTVS | 33 | ETTLTQSPSSLSASIGDRITIACQASQDIRNRLNWYLQRPGKAPQLLIYDASNLETGVPSKFAGRGSGTDFTLTISSLQPEDIGTYFCQQYGDLSPLTFGGGTKVDIRRTV | 113 |
| | | DIQMTQSPSSLSASVGDRVTITCRASQSISNYLNWYQQKPGKAPKLLIYAASSLQSGVPSRFSGSGSGTDFTLTISSLQPEDSATYYCQQSHSTPRTFGQGTKLEIKRTV | 114 |
| QVQLVQSGAEVKKPGSSVKVSCKTTGGTFSSYAVTWVRQAPGQGLEWMGGIGMFGTTNYAQKFQGRVTITADEMTSTAYMELSSLRSEDTAVYYCARGSYYYESSLDYWGKGTM | 34 | QSVLTQPPSVSGAPGQRVTISCTGTSSNIGAGFDVHWYQQFPGTAPKLLIYDNVKRPSGVPDRFSGSKSGTSASLAITGLRAEDEADYYCQSYDTSLSRYVFGTGTKVTVL | 115 |
| QVQLVQSGAEVKKPGSSVKVSCKASGGTFSSYAVTWVRQAPGQGLEWMGAIIGMFGTTNYAQKFQGRVTLTADELTSTAYMELSSLRSEDTAVYYCARGSYYYESSLDYWGQGTL | 35 | ETTLTQSPGTLSLSPGERATLSCRASQSVSSIYLAWYQQKPGQAPRLVIHGASSRATGIPDRFSGSGSGTDFTLTISRLEPEDFAVYYCQQYGSSPLTFGGGTKVEIKRTV | 116 |
| QVQLVQSGAEVKKPGSSVKVSCKTSGGTFSSYAVTWVRQAPGQGLEWMGAIIGMFGTTNYAQKFQGRVTLTADELTSTAYMELSSLRSEDTAVYYCARGSYYYESSLDYWGQGTL | 36 | ETTLTQSPGILSLSPGESATLSCGASQTISSRYLAWYQQRPGQAPRLLIFDASRRATGVPDRFSGGGSGTDFTLTISRLEPEDFGVFYCQQYGISPYTFGQGTKLEIKRTV | 117 |
| | | EIVLTQSPGTLSLSPGERATLSCRASQSVSGNNLAWYQQKFGQAPRLLIYAASSRATDIPARFSGSGSGTDFTLTISRLEPEDFAVYYCQQYVDSPRTFGQGTKVEIKRTV | 118 |
| | | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGGGTKVEIKRTV | 119 |
| | | EIVLTQSPGTLSLSPGERATLSCRASQSVSSSYLAWYQQKPGQAPRLLIYGASSRAAGIPDRFSGSGSGTDFTLTISRLEPEDFAVYYCQQYGSSPKTFGQGTKVEIKRTV | 120 |
| | | QSVLTQPPSVSGAPGQGVTISCSGSSSNIGANYVVHWYRQLPGAAPKLLIYDDIHRPSGVPDRFSGSRSGTSASLAITGLQPEDEADYYCQTYDTSLRGSVFGGGTKLTVL | 121 |
| | | QSVLTQPPSASGTPGQRVTISCSGSSSNIGSNYVYWYQQLPGTAPKLLIYRNNQRPSGVPDRFSGSGSGTSASLAISGLRSEDEADYYCAAWDDSLSGWVFGGGTKVTVL | 122 |
| | | QAVLTQPPSVSVAPGKTATITCGVNNLGRKSVHWYQQKPGQAPVLVVYDSNDRPSGIPERFSGSNSGNTATLIISRVEAGDEADYSCQVWDNNVDHPVFGGGTKLTVL | 123 |
| | | HVILTQPPSVSVAPGMTARMTCGGDNVGRRNVHWYQQKPGQAPVLVVYDDGGRPSAIPARFSGSKSGNTATLIISRVEAGDEADYTCQMWHSSGDQWVFGGGTKLTVL | 97 |
| | | SSELTQDPAVSVALGQTVRITCQGDSLRSYYASWYQQKPGQAPVLVIYGKNNRPSGIPDRFSGSSSGNTASLTITGAQAEDEADYYCNSRDSSGNHWVFGGGTKVTVL | 124 |
| | | EIVMTQSPGTLSLSPGERATLSCRASQSVSSSLAYWQQKPGQAPRLLIYGASNRATGIPDRFSGSGSGTDFTLTISRLEPEDFAVYYCQQYGGSPRTFGQGTKLEIKR | 125 |
| | | EIVLTQSPGTLSLSPGERATLSCRASQSVSSSYLAWYQQKPGQAPRLLIYGSSRATGIPDRFSGSGSGTDFTLTISRLEPEDFAVYYCQQYGSSPNFGGGTKVDIKR | 126 |

TABLE 2-continued

| Heavy Chain Sequence | SEQ ID NO | Light Chain Sequence | SEQ ID NO |
|---|---|---|---|
| | | QAVLTQPPSASGTPGQRVTISCSGSSSNIG SNSVYWYQQLPGTAPKLLIYRNNQRPSG VPDRFSGSGKSGTSASLAISGLQSEDEADY YCAAWDDSLNGVVFGGGTKLTVL | 127 |
| | | QSVVTQPPSVSGAPGQRVTISCTGSSSNIG AGYDVHWYQQLPGTAPKLLIYGDTNRPS GVPDRFSGSKSGTSASLAITGLQAEDEAD YYCQSYDGSRSGLVFGGGTKTVL | 128 |
| QVQLVQSGAEVKKPGSSVKVSCKTTGGTFSSY AVTWVRQAPGQGLEWMGGIIGMFGTTNYAQ KFQGRVTITADEMTSTAYMELSSLRSEDTAVY YCARGSYYYESSLDYWGKGTL | 37 | EIVLTQSPGTLSLSPGERATLSCRASQSLS NAYLAWYQQKPGQAPRLLLYGGSTRAT GIPDRFSGSGSGTDFTLTISSLEAEDFAVY YCQQYGSSPRTFGQGTKVEIKRTV | 129 |
| QVQLLQSGAEVKKPGSSVKVSCKTTGGTFSSY AVTWVRQAPGQGLEWMGGIIGMFGTTNYAQ KFQGRVTITADEMTSTAYMELSSLRSEDTAVY YCARGSYYYESSLDYWGKGTL | 38 | EIVLTQSPGTLSLSPGERATLSCRASQSVS SSYLAWYQQKPGQAPRLLIYGTSSRATDI PDRFSGSGSGTDFTLTISRLEPEDFAVYYC QQYGRSPFTFGGGTKVEIKRTV | 130 |
| QVQLQQSGAEVKKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGQGTL | 39 | DIQLTQSPSSLSASVGDRVTITCRASQGIS NYLAWYQQKPGKVPKLLIYAASTLQSGV PSRFSGSGSGTDFTLTISSLQPEDVATYYC QKYNSAPRTFGQGTKVEIKRTV | 131 |
| QVQLVQSGAEVLLPGSSVKVSCKTTGGTFSSY AVTWVRQAPGQGLEWMGGIIGMFGTTNYAQ KFQGRVTITADEMTSTAYMELSSLRSEDTAVY YCARGSYYYESSLDYWGQGTL | 40 | DIQLTQSPSSLSASVGDRVTITCRASQGIS NYLAWYQQKPGKVPKLLIYAASTLQSGV PSRFSGSGSGTDFTLTISSLQPEDVATYYC QKYNSAPLTFGGGTKVEIKRTV | 132 |
| | | EIVMTQSPGTLSLSPGERATLSCRASQSVS SSYLAWYQQKPGQAPRLLIYGASSRATGI PDRFSGSGSGTDFTKTUSRKEOEDFAVTTC QQYGSSPYTFGQGTKVEIK | 133 |
| QVQLVQSGAEVKKPGSSVKVSCKTSGGTFSSY AVTWVRQAPGQGLEWMGAIIGMFGTTNYAQ KFQGRVTLTADELTSTAYMELSSLRSEDTAVY YCARGSYYYESSLDYWGQGTM | 41 | QSVLTQPPSASGTPGQRVTISCSGSSSNIG SNFVYWYQQLPGTAPKLLIYKSNQRPSG VPDRFSGSKSGTSASLAISGLRSEDEADY YCAAWDDSLSGYVFGTGTQLTVL | 134 ) |
| QVQLVQSGAEVKKPGSSVKVSCKTSGGSFSSY AVTWVRQAPGQGLEWMGGIIGMFGTTNYAQ KFQGRVTITADELTSTAYMELSSLRSEDTAVY YCARGSYYYESSLDYWGQGTM | 42 | ETTLTQSPDTLSLSPGERATLSCRASQSVS SGSLAWYQQKPGQAPRLLIYAASSRAAGI PDRFSGSGSGTDFTLTISRLEPEDFAVYYC QQYGSSPGLTFGGGTQVEIKRTV | 135 |
| QVQLVQSGAEVKKPGSSVKVSCKTSGGTFSSY AVTWVRQAPGQGLEWMGGIIGMFGTTNYAQ KFQGRVTITADELRSTAYMELSSLRSEDTAVY YCARGSYYYESSLDYWGQGTL | 43 | ETTLTQSPGTLSLSPGERATLSCRASQSVS SSYLAYWQQKPGQAPRLLIYGASSRATGI PDRFSGSGSGTDFTLTISRLEPEDFAVYYC QQYGSSPYTFGQGTKLEIKRTV | 136 |
| QVQLVQSGAEVKKPGSSVKVSCKTSGGTFSSY AVTWVRQAPGQGLEWMGGIIGMFGTTNYAQ KFQGRVTITADELTSTAYMELSSLRSEDTAVY YCARGSYYYESSLDYWGQGTL | 44 | EIVLTQSPGTLSLSPGERATLSCRASQNIG WYLAWYYHKPGQAPRLIMYDASTRATG IPDRFSGSGSGTDFTLTISRLEPEDFAVYY CQQYDSVPSTFGQGTNLEIKRTV | 137 |
| | | QSVLTQPPSVSGAPGQRVTISCTGSSSNIG AGYDVHWYQQLPGTTPKLLIYDNTNRPS GVPDRFSASKSGASASLAITGLRDEDEAD YYCQSYDSSLSASVFGGGTLKTVL | 138 |
| QVQLVQSGAEVKKPGSSVKVSCKTSGGTFSSY AVTWVRQAPGQGLEWMGGIIGMFGTTNYAQ KFQGRVTITADELTSTAYMELSSLRSEDTAVY YCARGSYYYESSLDYWGRGTL | 45 | QSALTQPRSVSGSPGQSVTISCTGTTSDV GGYNYVSWYQQHPGEAPKLIIYDVSNRP SGVSNRFSGSKSGNTASLTVSGLQAEDEA DYYCSSFAGSSNLIFGGGTKLTVL | 139 |
| | | ETTLTQSPATLSVSPGERATLSCRASQSVS RNLAWYQQKPGQAPRLLIYGASSRATGIP DRFSGSGSGTDFTLTISRLEPEDFAVYYC QQYGSSSITFGQGTRLEIKRTV | 140 |
| QVQLVQSGAEVKKPGSSVKVSCKASGGTFSS YAVTWVRQAPGQGLEWMGAIIGMFGTTNYA QKFQGRVTLTADELTSTAYMELSSLRSEDTAV YYCARGSYYYESSLDYWGQGTM | 46 | SYELTQPPSASGTPGQRVTISCSGSSSNIGS NTVNWYQQLPGTAPKLLIYSNNHRPSGV PDRFSGSKSGTSASLAISGLQSEDEADYY CATWDDSLNGWVFGGGTKVTVL | 141 |

TABLE 2-continued

| Heavy Chain Sequence | SEQ ID NO | Light Chain Sequence | SEQ ID NO |
|---|---|---|---|
| QVQLVQSGAEVKKPGSSVKVSCKASGGTFSSYAVTWVRQAPGQGLEWMGAIIGMFGTTNYAQKFQGRVTITADELTSTAYMELSSLRSDDTAVYYCARGSYYYESSLDYWGQGTL | 47 | QSVLTQPPSASGTPGQRVTISCSGSSSNIGGNTVNWYQQVPGTAPKLLIHSNNQRPSGVPDRFSGSKSGTSASLAISGLLSEDEADYYCEVWDDSLNGRVFGGGTKLTVL | 142 |
| QVQLVQSGAEVKKPGSSVKVSCKTSGGTFSSYAVTWVRQAPGLGLEWMGAIIGMFGTTNYAQKFQGRVTITADELTSTAYMELSSLRSDTAVYYCARGSYYYESSLDYWGQGTL | 48 | DIQLTQSPSSLSASVGDRVTITCRASQGISNYLAWYQQKPGLVPKLLIYAASTLQSGVPSRFSGSGSGTDFTLTISSLQPEDFATYYCQQSYSTPRTFGQGTKLEIKR | 143 |
| | | HPELTQPPSASGTPGQRVTISCSGSSSNIGSNTVNWYQQLPGTGPKLLIYSNNQRPSGVPDRFSGSKSGTSASLAISGLQSEDEADYYCAAWDDSLNGWVFGGGTKVTVL | 144 |
| | | EIVLTQSPGTLSLSPGERATLSCRASQSVSSSYLAWYQQKPGQAPRLLIYGASSRATGIPDRFSGSGSGTDFTLTISRLEPEDFAVYYCQQFGSSQVTFGGGTKVEIKR | 145 |
| GVQLVQSGAEVKKPGSSVKVSCKTSGGTFSSYAVTWVRQAPGQGLEWMGAIIGMFGTTNYAQKFQGRVTLTADELTSTAYMELSSLRSEDTAVYYCARGSYYYESSLDYWGKGTM | 49 | HVILTQPPSVSVAPGMTARMTCGGDNVGRRNHWYQQKPGQAPVLVVYDDGGRPSAIPARFSGSKSGNTATLIISRVEAGDEADYYCQMWHSSGDQWVFGGGTKLTVL | 146 |
| GVQLVQSGAEVKKPGSSVKVSCKTSGGTFSSYAVTWVRQAPGQGLEWMGAIIGMFGTTNYAQKFQGRVTITADELTSTAYMELSSLRSDDTAVYYCARGSYYYESSLDYWGRGTL | 50 | QAVLTQPPSASGTPGQRVTISCSGSSSNIGSNYVYWYQHLPGTAPKLLIDRNDQRPSGVPDRFSGSKSGTSASLAISGLRSEDEADYYCAAWDDNLSGVVFGGGTKVTVL | 147 |
| QVQLVQSGAEVKKPGSSVKVSCKASGGTFSSYAISWVRQAPGQGLEWMGAIIGMFGTTNYAQKFQGRVTLTADELTSTQYMELSSLRSEDTAVYYCARGSYYYESSLDYWGKGTM | 51 | QSVVTQPPSVSGAPGQRVTISCTGSSIGAGYDVHWYQQLPRTAPKLLIFGNTNRPSGVPDRFSGSKSGTSASLTITGLQAEDEANYYCQTYDSSLSGWVFGGGTKLTVL | 148 |
| QVQLVQSGAEVKKPGSSVKVSCKASGGTFSSYAISWVRQAPGQGLEWMGAIIGMFGTTNYAQKFQGRVTITADELTSTAYMELSSLRSDDTAVYYCARGSYYYESSLDYWGKGTM | 52 | PELTQPPSASGTPGQRVTISCSGSSSNIGSNHVYWYQQLPGTAPKLLIYRNNQRPSGVPDRFSGSKSGTSASLAISGLRSEDEADYYCATWDDNLSGRLVFGGGTKLTVL | 149 |
| QVQLVQSGAEVKKPGSSVKVSCKTTGGTFSSYAVTWVRQAPGQGLEWMGGIIGMFGTTNYAQKFQGRVTITADEMTSTAYMELSSLRSEDTAVYYCARGSYYYESSLDYWGQGTM | 53 | QSVLTQPPSVSGAPGQRVTISCIGSNSNIGANFAVHWYQQLPGAAPKLLIYDNTNRPSGVPDRFSGSKSGTSASLDITGLQADDEADYYCQSYDARLNGWVFGGGTKLTVL | 150 |
| QVQLQQSGAEVKKPGSSVKVSCKTSGGTFSSYAVTWVRQAPGQGLEWMGAIIGMFGTTNYAQKFQGRVTITADELTSTAYMELSSLRSDDTAVYYCARGSYYYESSLDYWGKGTM | 54 | QSALTQPPSASGSPGQSVTISCAGASSDIGTYNSVSWYQQHPGKAPKLIIYEVTKRPSGVPDRFSGSKSGNTASLTVSGLQAEDEADYYCNSYAGTKGYVFGSGTKVTVL | 151 |
| QVQLQQSGAEVKKPGSSVKVSCKTSGGTFSSYAVTWVRQAPGQGLEWMGGIIGMFGTTNYAQKFQGRVTITADELTSTAYMELSSLRSEDTAVYYCARGSYYYENSLDYWGKGTL | 55 | SSELTQDPAVSVALGQTVRITCQGDSLRNEYASWYQQKPGQAPVLVMKGNNNRPSVIPDRFSGSRSGNTASLTITGAQAEDEADYYCSSRDSSGNRFFGSGTKVTVL | 152 |
| QVQLVQSGAEVKKPGSSVKVSCKTSGGTFSSYAVTWVRQAPGQGLEWMGAIIGMFGTTNYAQKFQGRVTLTADELTSTAYMELSSLRSEDTAVYYCARGSYYYESSLDYWGKGTM | 56 | HPELTQPPSLSVSPGQTATISCSGERLTNKYTSWYQQRPGQSPALVIYQDDKRPSGIPERFSGSGSGNTATLTISGTQPMDEAVYYCQAWDTNTQMTFGGGTKLTVL | 153 |
| QVQLVQSGAEVKKPGSSVKVSCKTSGGTFSSYAVTWVRQAPGQGLEWMGAIIGMFGTTNYAQKFQGRVTITADELTSTAYMELSSLRSDDTAVYYCARGSYYYESSLDYWGQGTM | 57 | QAVLTQPPSASGTPGQRVTISCSGSSSNIGTNTVNWYQQLPGTAPKLLIYRNIQRPSGVPDRSGSKSGTSASLAISGLQSEDEADYYCAAWDDSLNGYVFGTGTKLTVL | 154 |
| QVQLVQSGAEVKKPGSSVKVSCKTSGGTFSSYAVTWVRQAPGQGLEWMGAIIGMFGTTNYAQKFQGRVTITADELTSTAYMELSSLRSDDTAVYYCARGSYYYESSLDYWGRGTM | 58 | ETTLTQSPGTVSLSPGERATLSCRASQSVGGSNLAWYQQKPGQAPRLVIYATSRKANGIPDRFSGSGSGTDFTLTISRLEPEDFAVYFCQQYGTSPPSVTFGGGTKVEIRR | 155 |
| QVQLVQSGAEVKKPGSSVKVSCKASGGTFSSYAVTWVRQAPGQGLEWMGAIIGMFGTTNYAQKFQGRVTLTADELTSTAYMELSSLRSEDTAVYYCARGSYYYESSLDYWGKGTM | 59 | QAVLTQPPSASGTPGQRVTISCSGSSSNIGSNPVNWYQQLPGTAPKLLIYSNNQRPSGVPDRFSGSKSGTSASLAISGLQSEDEADYYCAAWDDSLTGYVFGTGTQLTVL | 156 |

TABLE 2-continued

| Heavy Chain Sequence | SEQ ID NO | Light Chain Sequence | SEQ ID NO |
|---|---|---|---|
| QVQLVQSGAEVKKPGSSVKVSCKASGGTFSS YAISWVRQAPGQGLEWMGGIIGMFGTTNYAQ KFQGRVTITADELTSTAYMELSSLRSEDTAVY YCARGSYYYESSLDYWGKGTT | 60 | SYVLTQPPSASGTPDQRVTISCSGSSSNIG SNYVYWYQQFPGAAPKLLMSRNNQRPS GVPDRFSGSKSGTSASLAISGLRSEDEAY YSCAAWDDSLNGLVFGGGTKVTVL | 157 |
| QVQLQESGPGLVKPSETLSLTCTVSGYSFDSG YYWGWLRQPPGKGLEWIGSIYHSRNTYYNPS LKSRVTISVDTSKNQFSLQLSSVTAADTAVYY CARGTWYSSNLRYWFDPWGKGTL | 61 | NFMLTQPHSVSESPGKTVISCTGSGGNI ARNYVQWYQQRPGSAPVTVILEDDKRPS GIPDRFSGSIDRSSNSASLTISGLRTEDEAL YYCQSYDDSDLVVFGGGTKLT | 158 |
| | | NFMLTQPHSVSESPGKTVTISCTGSSGSIA SNYVQWYQQRPGSAPTTVIYEDYQRPSG VPDRFSGSIDSSSNSASLTISGLKTEDEAD YYCQSYDDSDHLIFGGGTKLTVL | 159 |
| | | QSVLTQPPSASGTPGQRVTISCSGSSSNIG SNTVNWYKQLPGTAPRLLIYSNDQRPSG VPDRFSGSKSGTSASLAISGLQSEDEANY YCAAWDDSLSGWVFGGGTKLTVL | 160 |
| | | PELTQPHSVSESPGKTVTISCTGSGGRIAT NHVQWYQQRPGSAPTIVIYENNQRPSGV PNRFSGSIDDSSNSASLTISLARTEDEADY YCQSADATNVFFGGGTKVTVL | 161 |
| | | PELTQPPSASGTPGQRVTISCSGSSSNIGSN TVNWYQQLPGTAPKLLIYSNNQRPSGVP DRFSGSKSGTSASLAISGLQSEDEADYYC AAWDDSLNGWVFGGGTKLTVL | 162 |
| | | DIQMTQSPSSLSAFVGDRVTITCQASQDIS NYLNWYQQKPGKAPKLLIYDATNLETGV PSRFSGSGSGTDFTFISSLQPEDIATYYC QQYDNLPLTFGGGTKVDIKR | 163 |
| QVQLQESGPGQVKPSETLSLTCTVSGYSFDSG YYWGWLRQPPGKGLEWIGSIYHSRNTYYNPS LKSRVTISVDTSKNQFSLQLSSVTAADTAVYY CARGTWYSSNLRYWFDPWGKGTT | 62 | QSVLTQPPSASGTPGQRVTLSCSGSSSNIG GNSVNWYQHVPGTAPKLLMHSDDQRPS GVPDRFSGSKSGTSASLAISGLQSEDEAD YYCAAWDDSLNAWVFGGGTKVTVL | 164 |
| EVQLVQSGAAVKKPGSSVKVSCKASGGRFSS YAINWVRQAPGQGLEWMGGIIGMFGTTDYAQ KFQGRVTITADEVTSTGYMELRSLTSEDTAVY YCARGSGYHLQNPFDLWGRGTM | 63 | ETTLTQSPGTLSLSPGERATLSCRASQSVS SRYLAWYQQKPGQAPRLLIYGASNRATG VPDRFSGSGSGTDFTLTINRLEPEDFAVY YCQHYSRSLTFGGGTKVEIKRT | 165 |
| QVQLQQSGAAVKKPGSSVKVSCKASGGRFSS YAINWVRQAPGQGLEWMGGIIGMFGTTDYAQ KFQGRVTITADEVTSTGYMELRSLTSEDTAVY YCARGSGYHLQNPFDLWGKGTL | 64 | QSVLTQPPSVSAAPGQMVTISCSGSNSNI GNNYISWYQQLPGSAPRLLIYNNYKRPSG IPDRFSASKSGTSATLGITGLQTGDEADY YCGTWDSSKSSVVFGGGTKVTVL | 166 |
| EVQLVESGGGLVQPGGSLRLSCAASGFPFSSY VMIWVRQVPGKGLEWVSAIGGSGGSTYYADS VKGRFTISRDNSKNTLYLQMNSLRADDTAVY YCVLSPKSYYDNSGIYFDFWGRGTL | 65 | QSVLTQPPSVSGAPGQRVTISCTGSSSNTG AGNHVHWYQQVAGAAPKLLISNNNNRP SGVPDRFSASKSGTSASLDITGLQAEDEA DYYCQSYDNSLNDWVFGGGTQLTVL | 167 |
| EVQLVETGGGLVQPGGSLRLSCAASGFPFSSY VMIWVRQVPGKGLEWVSAIGGSGGSTYYADS VKGRFTISRDNSKNTLYLQMNSLRADDTAVY YCVLSPKSYYDNSGIYFDFWGKGTL | 66 | QSVVTQPPSESAAPGQKVTISCSGSSSNIG NNYVSWYQQFPGAAPKLLIFENNKRHSG IPDRFSGSKSGTSATLGIAELQTGDEADY YCGVWDSSLSAWVFGGGTQLTVL | 168 |
| EVQLVESGGGLVQPGGSLRLSCAASGFPFSSY VMIWVRQVPGKGLEWVSAIGGSGGSTYYADS VKGRFTISRDNSKNTLYLQMNSLRADDTAVY YCVLSPKSYYDNSGIYFDFWGRGTL | 67 | NFMLTQPHSVSESPGKTVTFSCTRSSGSIA SKYVQWYQQRPGSAPTIVIFENTKRPYGV PDRFSGSIDSSSNSASLTISGLKTEDEADY YCQSYDSSNHWVFGGGTQLTVLS | 169 |

Use of Neutralizing Antibodies

The influenza neutralizing antibodies of the present invention can be used for the prevention and/or treatment of influenza type A infections. For therapeutic applications, the antibodies or other molecules, the delivery of which is facilitated by using the antibodies or antibody-based transport sequences, are usually used in the form of pharmaceutical compositions. Techniques and formulations generally may be found in *Remington's Pharmaceutical Sciences,* 18th Edition, Mack Publishing Co. (Easton, Pa. 1990). See also, Wang and Hanson "Parenteral Formulations of Proteins and Peptides: Stability and Stabilizers," *Journal of Parenteral Science and Technology,* Technical Report No. 10, Supp. 42-2S (1988).

Antibodies are typically formulated in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, supra.

The neutralizing antibodies disclosed herein may also be formulated as immunoliposomes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

For the prevention or treatment of disease, the appropriate dosage of antibody will depend on the type of infection to be treated the severity and course of the disease, and whether the antibody is administered for preventive or therapeutic purposes. The antibody is suitably administered to the patient at one time or over a series of treatments. Depending on the type and severity of the disease, about 1 µg/kg to about 15 mg/kg of antibody is a typical initial candidate dosage for administration to the patient, whether, for example, by one or more separate administrations, or by continuous infusion.

The neutralizing antibodies of the present invention can be additionally used as a tool for epitope mapping of antigenic determinants of an influenza A virus, and are useful in vaccine development. Indeed, as shown in the Example below, the inventors herein have identified several broadly reactive neutralizing antibodies that can be used as guides for vaccine design.

Thus, the neutralizing antibodies of the present invention can be used to select peptides or polypeptides that functionally mimic the neutralization epitopes to which the antibodies bind, which, in turn, can be developed into vaccines against influenza A virus infection. In one embodiment, the present invention provides a vaccine effective against an influenza A virus comprising a peptide or polypeptide that functionally mimics a neutralization epitope bound by an antibody described herein. In one embodiment, the vaccine comprises a peptide or polypeptide functionally mimicking a neutralization epitope bound by an antibody that binds a hemagglutinin (HA) antigen. In another embodiments, the vaccine may be synthetic. In other embodiments, the vaccine may comprise (i) an attenuated influenza A virus, or a part thereof; or (ii) a killed influenza A virus, or part thereof. In one other embodiment, the vaccine comprises a peptide or polypeptide functionally mimicking a neutralization epitope bound by an antibody that binds a hemagglutinin (HA) antigen. The HA antigen may be an H5 subtype or an H1 subtype. In another embodiment, the HA antigen is displayed on the surface of an influenza A virus.

In another embodiment, the peptides or polypeptides of the vaccine contain antigenic determinants that raise influenza A virus neutralizing antibodies.

In a more general aspect, the neutralizing molecules, including but not limited to antibodies, are useful to prevent or treat viral infections. Thus, the neutralizing molecules of the present invention are useful in both immunotherapy, such as poassive immunization using one or more such molecules, and in the development of vaccines directed at the viral antigenic target(s).

Identification of Residues Important for Neutralizing Function

In a significant aspect of the present invention, a cluster of antibody residues important for neutralizing properties have been identified. In particular, it has been found that antibodies comprising an antibody heavy chain variable domain comprising at least one substitution in the surface exposed cluster determined by amino acid positions 52A, 53, 73, and 74, following Kabat amino acid numbering, have excellent neutralizing properties, including but not limited to neutralization of influenza viruses. In particular, it has been found that the following mutations: 52A (Pro→Gly), 53 (Ile→Met), 73 (Lys→Glu), and 74 (Ser→Leu or Met), relative to germ line chemistry, create a remarkably tight cluster on the exposed surface of the 4 heavy chain variable domain, where they form a ridge that protrudes prominently from the protein surface. An additional mutation important for neutralizing properties, 57 (Ala→Thr), is partially buried at the base of the CDR2 loop. The surface-exposed changes in CDR 2 and framework 3 are believed to have a direct role in antigen binding, where the less exposed mutation at position 57 and some additional mutations are likely have indirect effects through stabilizing and/or positioning of the CDR2 loop. Such additional mutations include conservative changes in CDR1 at position 34 (Ile→Val) and 35 (Ser→Thr) and also in CDR2 at position 50 (Gly→Ala). These mutations are believed to be important broadly for viral neutralizing properties, including, without limitation, neutralization of influenza A viruses, such as H5 HA, as well as HIV viruses.

These results are very valuable not only for understanding the immunochemical basis of neutralization but also for designing antibodies and antibody-like molecules with broad and improved viral neutralizing properties, as disclosed and claimed herein.

Vaccine development and the development of neutralizing antibodies with improved properties, using information about the residues important or beneficial for neutralizing properties disclosed herein, can additionally benefit from the combinatorial libraries of conformationally constrained polypeptide sequence described in PCT Application Publication No. WO 2008/089073, published on Jul. 24, 2008.

Non-Antibody Molecules with Neutralizing Properties

Although in the previous description the invention is illustrated with reference to antibody libraries, libraries of other, non-antibody molecules, such as surrobodies, can be prepared, used, and optimized in a similar manner. Thus, the construction of unique combinatorial protein libraries based on the pre-B cell receptor (pre-BCR) ("surrobody libraries") are described in Xu et al., 2008, supra. As discussed before, the pre-BCR is a protein that is produced during normal development of the antibody repertoire. Unlike that of canonical antibodies, the pre-BCR subunit is a trimer that is composed of an antibody heavy chain paired with two surrogate light chain (SLC) components. Combinatorial libraries based on these pre-BCR proteins in which diverse heavy chains are paired with a fixed SLC were expressed in mammalian, *Escherichia coli*, and phagemid systems. These libraries contain members that have nanomolar affinity for a target antigen. A description of the library construction, selective enrichment, and biophysical characterization of library members is detailed in the Materials and Methods section of the Xu et al. paper.

Further details of the invention are illustrated by the following non-limiting Examples.

EXAMPLE 1

Antibody Libraries from Survivors of Prior Bird Flu Outbreaks and Preparation of Neutralizing Antibodies The widespread incidence of H5N1 influenza viruses in bird populations poses risks to human health. Even though the virus has not yet adapted for facile transmission between humans, it can cause severe disease and often death. Here we report the generation of combinatorial antibody libraries from the bone marrow of five survivors of the recent H5N1 avian influenza outbreak in Turkey. To date, these libraries have yielded >300 unique antibodies against H5N1 viral antigens. Amongst these antibodies, we have identified several broadly reactive neutralizing antibodies that could be used for passive immunization against H5N1 virus or as guides for vaccine design. The large number of antibodies obtained from these survivors provides a detailed immunochemical analysis of individual human solutions to virus neutralization in the setting of an actual virulent influenza outbreak. Remarkably, two of these antibodies neutralized both H1 and H5 subtype influenza viruses.

Newly emergent highly pathogenic influenza virus strains pose a profound threat to man. Three influenza pandemics have occurred within the past 100 years, each with devastating consequences (Palese, P. & Shaw, M. L. In Fields Virology, Vol. 11 (Eds. Knipe, D M and Howley, P. M.) Lippencott Williams and Wilkins, Philadelphia, 2006, 1648-1689)). The recent emergence of the H5N1 virus strain, though mainly confined at present to avian hosts, has already demonstrated virulence in humans, causing the death of more than 200 people ((2008) (World Health Organization, Geneva)). Therefore, healthcare officials, researchers, and governments are actively considering their options should a pandemic occur. One widely considered approach concerns the use of passive antibodies either for prevention of disease or treatment after exposure to virus (Luke, T. C. et al. (2006) *Ann Intern Med* 145, 599-609). The potential for passive immunization against influenza has been evident since the Spanish influenza nearly a century ago, where the benefits of transfused of blood, sera, and blood products reduced the risk of mortality by more than 50% (Id.). Recently the benefits of treatment with convalescent plasma have also been reported in instances of H5N1 influenza (Kong L K & Zhou B P (2006) *Hong Kong Med J* 12, 489; Zhou, B. et al. (2007) *N Engl J Med* 357, 1450-1451). Additionally, passive immunization with human and mouse monoclonal antibodies has been reported to protect animals from death, even when given after H5N1 infection (Hanson, B. J. et al. (2006) *Respir Res* 7, 126)).

The most logical source of human antibodies for passive therapy would be patients that have survived infection. Through the use of modern combinatorial antibody library technologies, it is now possible to capture the entire immunological history of an individual's response to an infection (Law, M. et al. (2007) *Nat Med*. January; 14(1):25-7. Epub 2007 Dec. 6; Lerner R A (2006) *Angew Chem Int Ed Engl* 45, 8106-8125). Because antibody libraries contain the complete record of an individual's response to pathogens, one can recover the repertoire specific to a given agent by using a laboratory process of selective enrichment. Such libraries both give archival information as to the nature of antibodies made during the infection and allow recovery of potentially therapeutic human monoclonal antibodies. Importantly, antibody recovery is independent of whether an active antibody response is still occurring at the time the sample is taken. Thus, depending on when the libraries are constructed, one may obtain antibodies that are currently being made and/or are part of the individual's immunological history. For infections that may be lethal, such analyses carried out on surviving patients may be particularly important because they chart some of the immunological mechanisms used during a successful host defense in the actual clinical setting of an outbreak.

Typically, when libraries are prepared from individuals who have been infected with a virus, hundreds to thousands of different antibodies are obtained, as opposed to only a few when other methods are used (Lerner R A (2006) *Angew Chem Int Ed Engl* 45, 8106-8125). This has several consequences. A comparative sequence analysis of these antibodies allows a detailed map of the chemistry of antibody binding. Similarly, a comparison of neutralizing and non-neutralizing antibodies can give important information about the nature of binding interactions that are critical to neutralization.

Here we describe the creation of the first comprehensive avian influenza antibody libraries made from survivors of infection with an avian influenza virus during a confirmed outbreak. We have used these libraries to obtain large numbers of monoclonal antibodies to the H5N1 avian influenza virus, some of which have broad reactivity and are neutralizing across viral sub-types. Ultimately these combinatorial antibody libraries may hold the key to immunotherapy, such as passive immunization, using one or more member antibodies, or they may guide the development of vaccines utilizing the antigenic target(s) of the neutralizing antibodies in the library.

The outbreak and source of material. Between December 2005 and January 2006 an outbreak of avian influenza H5N1 occurred in Turkey (A. F. Oner et al., *N Engl J Med* 355, 2179 (Nov. 23, 2006)). In total, twelve individuals were infected and only eight survived. Because bone marrow RNA contains the archived record of all antibodies made by an individual, we selected it as our source material. We obtained bone marrow and serum from six of the Turkish survivors approximately 4 months following recovery and successfully prepared antibody libraries from five of the six bone marrow samples. In the sixth sample the RNA was degraded.

Serological analysis. The hemagglutinin protein is essential for binding the influenza virus to the cell that is being infected and is generally considered to be the main target of neutralizing antibodies (Palese, P. & Shaw, M. L. In Fields Virology, Vol. 11 (Eds. Knipe, D M and Howley, P. M.) Lippencott Williams and Wilkins, Philadelphia, 2006, 1648-1689) (2008) (World Health Organization, Geneva)). Therefore, we tested by ELISA each of the individual serum samples at high serum dilutions for the detection of antibodies against H5 hemagglutinin proteins (FIG. 8) and intact viruses (data not shown). This analysis showed that the patients had readily detectable serum antibodies, even when diluted 10,000-fold. We selected the Vietnam/1203/04 hemagglutinin as a target because it was readily available and is thought to be related to the influenza virus strain that caused the outbreak of disease in Turkey.

Library construction. Our primary objectives were to understand the nature of the immunological response to infection and to identify specific antibodies that might be used passively for the prevention of spread and/or treatment of H5N1 influenza virus infections. We wished to recover every possible solution to H5N1 infections with minimal or no bias. Because gene expression for the individual immunoglobulin families is not equal, making them prone to bias and over-representation, we decided against using the standard pooled approach to immunoglobulin recovery. Instead, we individually rescued 20 of the 23 distinctly amplifiable gene families during the construction of the libraries. The remaining three gene families ($V_H$ 2, 5, and 6) were recovered as a pool because they are infrequently used. We further normalized gene content by creating equimolar pools of each immunoglobulin family DNA for cloning into a phagemid display vector.

A unique DNA bar code was embedded into a non-disruptive portion of the phagemid vector to allow each clone to be tracked back to the original patient source (FIG. 9). This bar coding allows assignment of clones to individual patients even when phage libraries from multiple survivors are screened simultaneously. As a result of this tagging, every clone isolated from any library can be confidently attributed to the cognate survivor.

As illustrated in FIG. 9, cloning and barcoding of annotated repertoires allows tracking of all clones to their sources. Each survivor is assigned a unique barcoded vector and immunoglobulin repertoires are cloned via restriction sites indicated in the upper panel. Plasmids from any clone can be assigned to designated sub-libraries via their light chain class and their survivor barcode.

Using this vector with its coding system, we successfully cloned repertoires from the bone marrow of five of the six survivors in both single chain (scFv) and Fab phagemid formats. Each collection from an individual survivor has a diversity of greater than $1.0\times10^8$ members. Furthermore, we created additional bar coded libraries comprised of mixed survivor light and heavy chains with a final diversity of $1.1\times10^9$. Collectively the 5 donor-specific collections and the pooled libraries from all donors have a total diversity of $1.0\times10^9$ as a scFv collection and $4.2\times10^9$ as a Fab-displayed collection (Table 3).

Table 3 shows the light chain and full library total transformants in both scFv and Fab formats. Total diversity represented by all libraries is $5.6\times10^9$.

TABLE 3

| | Light Chains | | Completed Libraries | |
|---|---|---|---|---|
| | Kappa | Lambda | Kappa | Lambda |
| | | scFv | | |
| H5-1 | 3.00E+06 | 4.00E+06 | 1.50E+08 | 1.20E+08 |
| H5-2 | 3.00E+06 | 3.00E+06 | 4.00E+07 | 1.60E+07 |
| H5-3 | 8.20E+05 | 1.70E+06 | 5.30E+07 | 1.50E+08 |
| H5-5 | 7.00E+06 | 5.60E+06 | 6.50E+08 | 5.60E+07 |
| H5-6 | 1.50E+06 | 5.00E+06 | ND | 1.00E+07 |
| H5Pool | Not Determined | | 1.80E+08 | 5.70E+08 |
| | | Totals | 1.10E+09 | 9.20E+08 |
| | | scFv Total | 2.00E+09 | |
| | | Fab | | |
| H5-1 | 1.50E+06 | 2.90E+06 | 2.90E+08 | 4.60E+08 |
| H5-2 | 3.10E+06 | 9.40E+05 | 4.40E+08 | 4.30E+08 |
| H5-3 | 2.80E+06 | 2.30E+06 | 3.90E+08 | 3.90E+08 |
| H5-5 | 7.00E+06 | 5.60E+06 | 7.20E+08 | 1.70E+08 |
| H5-6 | 1.50E+06 | 5.00E+06 | ND | ND |
| H5Pool | 1.90E+07 | | 2.60E+08 | |
| | | Totals | 2.10E+09 | 1.45E+09 |
| | | Fab Total | 3.60E+09 | |

Selecting binding antibodies. As indicated above, one interesting feature of these studies was that we initially selected antibodies for binding against a virus strain and antigen that was related to, but different from, the one that caused the infection. This was because viral isolates from the patients were not available. The necessity of using a related strain to select antibodies could have proven fortuitous because it may have led to the isolation of more broadly neutralizing antibodies (see below).

The libraries were panned against inactivated virus containing the Vietnam/1203/04 virus HA and NA proteins and recombinant purified hemagglutinin (Barbas, C. et al. (2001) *Phage Display, A Laboratory Manual* (Cold Spring Harbor Laboratory Press)). Typically, following three to four rounds of phage panning, individual clones from enriched phage pools were analyzed by ELISA against H5N1 virus or purified hemagglutinin and the positive clones were sequenced to determine their heavy and light chain sequences and to read their survivor bar code (D. W. Coomber, *Methods Mol Biol* 178, 133 (2002)). From these studies, we isolated specific H5 hemagglutinin binding clones from all five of the individual libraries from survivors. In total, we have so far recovered more than 300 hundred different antiviral antibodies, of which 146 specifically bind the H5 hemagglutinin protein.

General Features of the Selected Clones. Overall, the individual patients use different germ lines for both heavy and light chains, demonstrating that individual patients have found different solutions to the same potentially lethal immunological challenge. The major features of combinatorial antibody libraries that can be used both to give confidence as to the quality of the obtained repertoire and to provide information as to the chemistry of antibody binding and/or neutralization are seen in these clones. These clones contain all the hallmarks of the previously described repeated clones ("jackpot solution") to antigen binding that is found in the natural progression of affinity maturation, as well as in selected synthetic antibody libraries (Lerner, R. A. *Angew Chem Int Ed Engl* 45, 8106 (Dec. 11, 2006); A. Rajpal et al., *Proc Natl Acad Sci USA* 102, 8466 (Jun. 14, 2005)). The presence of "jackpots" in these large collections validates the screening procedure because, unless the phage were selected on the basis of activity, the chance of obtaining the same clone multiple times is highly improbable. Moreover, when one analyzes the heavy chain differences within groups, it was observed that many of the amino acid substitutions were chemically and structurally conservative (Table 1). As with repeated clones, the appearance of multiple amino acid substitutions that are chemically reasonable is unlikely to be a random event.

Binding Specificity of recovered antibodies. Initial testing of a set of Fabs using Bio-Layer Interferometry binding to the H5 Vietnam hemagglutinin protein indicated that we had identified at least four distinct epitopes (data not shown). We selected six clones from three survivors that recognized two different epitopes for conversion into full IgG$_1$ proteins. The binding of three of these antibodies was mapped to the HA1 subunit of the hemagglutinin protein by western blot analysis (data not shown).

One goal of these studies was to recover those rare antibodies that broadly neutralize divergent viral strains. There was a suggestion that some of our antibodies might be broadly reactive because the serum from the donors had high titer antibodies against a divergent subfamily of H5N1 viruses that extended beyond the virus with which they were infected. To determine the degree of cross reactivity at the level of individual antibodies, we analyzed binding of our clones to different influenza hemagglutinin antigens (FIG. 6).

FIG. 6 shows the cross-reactivity of H5N1 antibodies from two survivors with hemagglutinins from H1N1 viruses. (A) Bars are H5N1 Vietnam 1203/04(dark grey), H5N1 Turkey/65596/06 (white), H5N1 Indonesia/5/05 (diagonal stripes), H1N1 New Calcdonia/20/99 (vertical stripes), H1N1 South Carolina/1/18 (crosshatch stripes), and H3N2 Wisconsin/67/05 (light gray). (B) Relative ranking of antibodies by their ELISA signal over background ("+" is above background and less than 2 fold, "++" is between 2 and 9-fold, "+++" is between 9 and 15-fold, "++++" is greater than 15-fold above background, and "–" is not measurably above background), on the various proteins. Not surprisingly, these antibodies recognize hemagglutinin from the corresponding infecting Turkey/65596/06 strain, and in addition recognize the heterologous hemagglutinin from the Vietnam/1203/04 strain used for selection. Furthermore, they recognize the antigenically divergent Indonesian/5/05 H5 hemagglutinin. We performed kinetic binding analyses on prototype antibodies and found that the antibodies from survivor 5 bound Vietnam/1203/04 hemagglutinin with single digit nanomolar affinities, while the survivor 2 antibody bound more strongly with a measured affinity of 13 pM. The available binding affinities for H5 and H1 and the clonal identities of the Fab fragments for the antibodies are as follows.

| Identity | H5 | H1 |
|---|---|---|
| A | 10-40 nM | 40-80 nM |
| B | 130 pM | |
| C | 10-40 nM | |
| D | 13 pM | |
| E | 4 nM | 90 nM |

-continued

To determine if our antibodies are even more broadly reactive, we studied their binding to a larger collection of hemagglutinins from different influenza A subtypes (FIG. 6). We found that the four prototype antibodies bound hemagglutinin from the closely related subtype H1N1 contemporary reference strain New Calcdonia/20/99. Notably, the three neutralizing antibodies belonging to survivor 5 also bound hemagglutinin from the H1N1 South Carolina/1/18 isolate that emerged during the 1918 Spanish Flu pandemic. Conversely, none of these four antibodies bound hemagglutinin from the contemporary H3N2 Wisconsin/67/05 reference strain, indicating that even though the antibodies display broad spectrum binding amongst and between Influenza subtypes, the reactivity did not extend to all influenza subtypes.

To further explore the immunochemical basis of the H1/H5 cross-reactivity, we re-screened the libraries against the H1N1 New Calcdonia/20/99 hemagglutinin protein. From this selection, we found clones (Table 6) that bore significant similarity to the sequences previously obtained from survivor 5 when the H5 hemagglutinin protein was used in the panning (Table 5).

Neutralization Studies. Initially the antibodies were assayed for their ability to neutralize an H5 HA (Vietnam/1203/04) containing influenza virus. One antibody derived from survivor 2 and 3 from survivor 5 that recognized a common epitope (epitope "A") were all neutralizing whereas the two antibodies derived from survivor 1 that recognized a second epitope (epitope "B") were not.

Based on the striking sequence similarity of clones separately isolated from survivor 5 against either H5N1 or H1N1 hemagglutinin, we predicted that their cross reactivity would extend beyond simple binding and they would also have the highly unusual property of neutralizing both H5N1 and H1N1 virus. To test the cross neutralizing activity of the IgGs, we tested representative antibodies from the H5N1 screen in a neutralization assay to see if they would also neutralize H1N1 or H3N2 virus (Table 4). We studied the H1 bearing virus A/New Cal/20/99 and the H3 bearing virus A/Hong Kong/68. A collection of viruses bearing H5 subtype hemagglutinin was also tested (A/Vn/1203/04; A/Indo/5/05; A/Turkey/65596/06; A/Egypt/06). The antibodies showed no activity against H3 subtype influenza. However, three of the monoclonal antibodies (1-3) that neutralized H5 containing viruses also strongly neutralized all viruses bearing HA from subtypes H1 (Table 4).

TABLE 4

| | Virus* | | | | | | |
|---|---|---|---|---|---|---|---|
| | H5 | | | | | H1 | H3 |
| | A/Vietnam 1203/04 ‡ | A/Vietnam 1203/04 ‡ | A/Indonesia 5/05 | A/Turkey 65596/06 | A/Egypt 14725/06 | A/New Cal 20/99 | A/Hong Kong/68 |
| Ab 1† | 11-21 | 2.3-9.3 | 9.3 | 9.3 | 1.2-2.3 | 9 | >333 |
| Ab 2† | 63 | 54-217 | 27 | 108 | 7-13 | 54-108 | >333 |
| Ab 3† | 58 | 18 | 16 | 31 | 4-8 | 8-16 | >333 |
| Ab 4† | 1.7-6.3 | 0.5-2.2 | >333 | Not done | Not done | >333 | >333 |
| Mab #8§ | 2.7 | Not done | Not done | Not done | Not done | Not done | Not done |

The results of Table 4 were obtained as follows. MDCK cells were inoculated with 100 TCID50 of virus in the presence of 2-fold serial dilutions of monoclonal antibodies. †—Minimum inhibitory concentrations required to neutralize virus in duplicate samples are presented in ug/ml. ‡—The viral neutralization results from two independent experiments are both shown. §—Mab#8 is a mouse monoclonal H5N1 neutralizing antibody raised against A/Vietnam/1203/04.

Immunochemical basis of neutralization. One advantage of antibody libraries is that when one obtains large numbers of antibodies, they can be grouped as to their relatedness. Thus, when a function for a given antibody in the collection is observed one can predict that other members of the group to which it belongs will have similar activity.

Table 5 shows example sequences displaying the immunochemical basis of neutralization discovered from Survivor 5 libraries following H5N1 Vietnam panning The 61 unique heavy chain sequences aligned with their germline variable regions (variable (V) region gene $V_H1e/V_H1\text{-}69$) from the 114 unique heavy and light chain combinations. Requisite mutations are shown in bolded, underlined text (column 5—PI to GM and A to T; column 6—KS to EL or EM or XL) and predominant mutations are shown in italicized, underlined text (column 2—A to T; column 3—IS to VT; column 5—G to A; column 8—K to Q or R). Heavy chains sequences also discovered in H1N1 New Calcdonia panning are highlighted in gray. Antibody regions and Kabat numbering ranges are listed at the top of each sequence column. The heavy chain/light chain pairing is indicated in the first column as follows: *—paired with 2 unique light chains, †—paired with 3 unique light chains, ‡—paired with 4 unique light chains, §—paired with 5 unique light chains, and ¶—paired with 12 unique light chains.

TABLE 5

(SEQ ID NOS 177-214, and 215-238, respectively, in order of appearance)

| Group 1 heavy chains Vh1e | FR1 1-29 QVQLVQSGAEVKKPGSSVKVSCKASGGTF | CDR1 30-35 SSYAIS | FR2 36-46 WVRQAPGQGLE | CDR2 47-56 WMGGIIPIFGTAN | FR3 59-92 YAQKFQGRVTITADKSTSTAYMELSSLRSEDTAVYYC | CDR3 93-101 ARGSYYYESSLD | FR4 102-113 YWGQGTLVTVSS |
|---|---|---|---|---|---|---|---|
| 1 | ----------------------------- | ------ | ----------- | ---GM---T- | ---------------------------------EL- | --------- | ---K-T- |
| 2 | ----------------------------- | ------ | ----------- | ---GM---T- | ---------------------------------EL- | --------- | ---K-M- |
| 3 | ----------------------------- | ------ | ----------- | ---A-GM---T- | -------------L-------------------EL- | --------- | ---K-M- |
| 4* | ----------------------------- | ---VT | ----------- | ---A-GM---T- | ---------------------D-----------EL- | --------- | ------- |
| 5 | ----------------------------- | ---VT | ----------- | ---A-GM---T- | -------------L-------------------EL- | --------- | ------- |
| 6 | ----------------------------- | ------ | ----------- | ---A-GM---T- | ---------------------D-----------EL- | --------- | ------- |
| 7‡ | ---------T------------------- | ---VT | ----------- | ---GM---T- | ---------------------------------ELR | --------- | ---R-- |
| 8* | ---------T------------------- | ---VT | ----------- | ---GM---T- | ---------------------D-----------EL- | --------- | ------- |
| 9† | ---------T------------------- | ---VT | ----------- | ---A-GM---T- | ---------------------D-----------EL- | --------- | ------- |
| 10 | ---------T------------------- | ---VT | ----------- | ---GM---T- | ---------------------D-----------EL- | --------- | ---R-M- |
| 11* | ---------T------------------- | ---VT | ----------- | ---A-GM---T- | ---------------------D-----------EL- | --------- | -----M- |
| 12¶ | ---------T------------------- | ---VT | ----------- | ---A-GM---T- | -------------L-------------------EL- | --------- | -----M- |
| 13* | ---------T------------------- | ---VT | ----------- | ---A-GM---T- | -------------L-------------------EL- | --------- | -----M- |
| 14 | ----------------------------- | ---VT | ----------- | ---GM---T- | -------------L-------------------EL- | --------- | ---K-M- |
| 15 | ----------------------------- | ---VT | ----------- | ---GM---T- | -------------L-------------------EL- | --------- | ------- |
| 16* | ----------------------------- | ---VT | ----------- | ---A-GM---T- | -------------L-------------------EL- | --------- | ------- |
| 17 | ------R---------------------- | ---VT | ----------- | ---GM---T- | -----------------------X---------EL- | -----TT- | ---R-- |
| 18 | ---------T---S--------------- | ---VT | ----------- | ---A-GM---T- | ---------------------------------EL- | --------- | ------- |
| 19 | ---------TT------------------ | ---VT | ----------- | ---A-GM---T- | ---------------------------------EM- | --------- | ---M- |
| 20§ | ---------TT------------------ | ---VT | ----------- | ---GM---T- | ---------------------------------EM- | --------- | ---K-M- |
| 21 | ---------TT------------------ | ---VT | ----------- | ---GM---T- | ---------------------------------EM- | --------- | ---K-- |
| 22 | ---------TT------------------ | ---VT | ----------- | ---GM---T- | ---------------------------------EL- | --------- | -----M- |
| 23 | ---------X------------------- | ---VT | ----------- | ---A-GM---T- | ---------------------D-----------EL- | --------- | ------- |

TABLE 5-continued (SEQ ID NOS 177-214, and 215-238, respectively, in order of appearance)

| | | | | | | | | | | | |
|---|---|---|---|---|---|---|---|---|---|---|---|
| 24 | E------ | ------- | ---- | ---- | ------- | ---A- | -GM- -T- | ---- | --EL | ---- | ---- | ---- |
| 25 | E------ | ---T--- | ---L- | --VT | ------- | ----- | -GM- -T- | -L-- | --EM | ---- | -TT- | --R-M- |
| 26 | E------ | ---T--- | ---V- | --VT | ------- | ---A- | -GM- -T- | ---- | --EL | --D- | ---- | --G-T- |
| 27 | E------ | ---Q--- | ---T- | --VT | ------- | ---A- | -GM- -T- | -L-- | --EL | --D- | ---- | ---- |
| 28 | E------ | ---A--- | ---A- | --VT | ------- | ----- | -GM- -T- | ---- | --EL | ---- | ---- | --M-- |
| 29† | E------ | ------- | ---R- | --VT | ------- | ----- | -GM- -T- | ---- | --EM | ---- | -TT- | ---- |
| 30† | E------ | ------- | ---R- | --VT | ------- | ----- | -GM- -T- | -L-- | --EM | --D- | -TT- | --K-- |
| 31 | E------ | ------- | ---R- | --VT | ------- | ----- | -GM- -T- | -L-- | --EM | --D- | -TT- | --R-M- |
| 32 | E------ | ------- | ---T- | --VT | ------- | ---A- | -GM- -T- | -L-- | --EL | ---- | ---- | --R-- |
| 33* | E------ | ------- | ---T- | --VT | ------- | ---A- | -GM- -T- | -L-- | --EL | --D- | ---- | --K-- |
| 34‡ | E------ | ------- | ---T- | --VT | ------- | ---A- | -GM- -T- | -L-- | --EL | --D- | ---- | --K-- |
| 35 | E------ | ------- | ---T- | --VT | ------- | ---A- | -GM- -T- | -L-- | --EL | --D- | ---- | --M-- |
| 36 | E------ | ------- | ---T- | --VT | ------- | ---A- | -GM- -T- | -L-- | --EL | --D- | ---- | --K-- |
| 37 | E------ | ------- | ---T- | --VT | ------- | ---A- | -GM- -T- | -L-- | --EL | --D- | ---- | --K-T- |
| 38 | E------ | ------- | ---T- | --VT | ------- | ---A- | -GM- -T- | -L-- | --EL | --D- | ---- | --K-M- |
| 39§ | E------ | ------- | ---T- | --VT | ------- | ---A- | -GM- -T- | -L-- | --EL | ---- | ---- | --K-- |
| 40§ | E------ | ------- | ---T- | --VT | ------- | ---A- | -GM- -T- | -L-- | --EL | ---- | ---- | --K-M- |
| 41* | E------ | ------- | ---T- | --VT | ------- | ---A- | -GM- -T- | -L-- | --EL | ---- | ---- | --K-- |
| 42† | E------ | ------- | ---T- | --VT | ------- | ---A- | -GM- -T- | -L-- | --EL | ---- | ---- | --R-- |
| 43 | E------ | ------- | ---T- | --VT | ------- | ---A- | -GM- -T- | -L-- | --XL | ---- | ---- | --R-- |
| 44 | E------ | ------- | ---T- | --VT | ------- | ---A- | -GM- -T- | -L-- | --EL | ---- | ---- | --R-M- |
| 45 | E------ | ------- | ---T- | --VT | ------- | ---A- | -GM- -T- | -M-- | --EM | ---- | ---- | --K-- |
| 46 | E------ | ------- | ---T- | --VT | ------- | ---A- | -GM- -T- | ---- | --EL | ---- | ---- | ---- |

TABLE 5-continued (SEQ ID NOS 177-214, and 215-238, respectively, in order of appearance)

| | | | | | | | | | |
|---|---|---|---|---|---|---|---|---|---|
| 47 | E------ | ----T- | --VT | ------ | --GM---T- | ------ | -EL- | ------ | ---K- |
| 48† | E------ | ----T- | --VT | ------ | --GM---T- | ------ | -EM- | ------ | ---R- |
| 49 | E------ | ----T- | --VT | ------ | --GM---T- | ------ | -EM- | ------ | --R--M- |
| 50† | E------ | ----TT- | --VT | ------ | --GM---T- | ------ | -EM- | ------ | ---R- |
| 51 | E------ | ----T- | --VT | ------ | --GM---T- | ------ | -EM- | ------ | ----M- |
| 52 | G------ | ----T- | --VT | ------ | --A-GM---T- | ---L-- | -EL- | ------ | ---K--M- |
| 53 | G------ | ----T- | --VT | ------ | --A-GM---T- | ------ | -EL- | ---D-- | ---R- |
| 54 | -M----- | ----T- | --VT | ------ | --A-GM---T- | ------ | -EL- | ---D-- | ---K--M- |
| 55† | M----- | ----T- | --VT | ------ | --A-GM---T- | ---L-- | -EL- | ------ | ---K--M- |
| 56 | ---L--- | ----TT- | --VT | ------ | --GM---T- | ------ | -EM- | ------ | ---K- |
| 57† | ---Q--- | ----T- | --VT | ------ | --A-GM---T- | ---L-- | -EL- | ---D-- | ---K--M- |
| 58 | ---Q--- | ----T- | --VT | ------ | --A-GM---T- | ------ | -EL- | ------ | ---K- |
| 59 | ---Q--- | ----T- | --VT | ------ | --GM---T- | ------ | -EL- | ---N-- | ---K- |
| 60* | ---Q--- | --R-T- | --VT | ------ | --GM---T- | ---L-- | -EM- | -TT- | ----M- |
| 61* | ---Q--- | --R--- | --VT | ------ | --GM---T- | ---L-- | -EM- | -TT- | ---K- |

All members of the group that contained the neutralizing antibody collection against epitope "A" from survivor 5, analyzed to date, are shown in Table 1. The group is comprised of 61 unique members that most closely resemble the variable (V) region gene $V_H1e/V_H1-69$ germ line heavy chain. Some heavy chains are paired with more than one light chain. In total these heavy chains have 114 unique pairings to both kappa and lambda light chains. Comparing these heavy chains to the highly related $V_H1e/V_H1-69$ germline, we observe three types of point substitutions. Some changes appear to be required, others are dominant, and some residues have only been changed sporadically. The changes that are required occur in every clone in the group within CDR2 at position 52A (Pro>Gly), 53 (Ile>Met), and 57 (Ala>Thr), as well as in the framework 3 region at position 73 (Lys>Glu) and 74 (Ser>Leu or Met), all of which vary from the germline side chain chemistries, suggesting that these mutations are critical to antigen binding and neutralization. The second set of mutations is dominant and found in most clones. The first, in framework 1 at position 24 (Ala>Thr), represents a significant chemical change. The next three are conservative changes in CDR1 at positions 34(Ile>Val) and 35 (Ser>Thr) and also in CDR2 at position 50 (Gly>Ala). All four of these dominant substitutions, however, are dispensable, suggesting that, while beneficial, they are not essential. The sporadic changes found throughout framework regions 1, 3, and 4, as well as CDR3, are all conservative and likely represent minor optimization events.

Table 6 shows examples of sequences displaying the Immunochemical basis of neutralization discovered from Survivor 5 libraries following H1N1 New Calcdonia panning. The 35 unique heavy chain sequences aligned with their germline variable regions from the 82 unique heavy and light chain combinations. Requisite mutations are highlighted in bolded, underlined text (column 2—A to T; column 3—IS to VT; column 5—PI to GM and A to T; column 6—KS to EL or EM and K to E) and predominant mutations are shown in italicized, underlined text (column 2—Q to E; column 5—G to A; column 6—I to L or M; column 8—Q to K or R or E). Heavy chains sequences also discovered in H5N1 Vietnam panning are highlighted in gray.

TABLE 6

(SEQ ID NOS 177, 181, 184, 239-241, 186, 242, 188-190, 243-247, 197, 248-249, 207, 211-218, 250, 219, 251, 225, 252-253, 232, 254, 234, and 237, respectively, in order of appearance)

| Group 1 heavy chains Vhle | FR1 1-29 QVQLVQSGAEVKKPGSSVKVSCKASGGTF | CDR1 30-35 SSYAIS | FR2 36-46 WVRQAPGQGLE | CDR2 47-56 WMGGIIPIFGTAN | FR3 59-92 YAQKFQGRVTITADKSTSTAYMELSSLRSEDTAVYYC | CDR3 93-101 ARGSYYYESSLD | FR4 102-113 YWGQGTLVTVSS |
|---|---|---|---|---|---|---|---|
| 1* | | | | | | | |
| 2‡ | | VT | | -T- -T | EL | | |
| 3 | -------T------ | -VT | | -GM---T- | --------M---EM---------------- | | ---M---- |
| 4 | -------T------ | -VT | | -GM---T- | ------------EM---------------- | | |
| 5 | -------T------ | -VT | | -GM---T- | ------------EM---------------- | | |
| 6† | -------T------ | VT | | -A--GM---T- | --------L---EL---------------- | | |
| 7 | | | | | ------------EL----------D----- | | |
| 8* | -------T------ | VT | | -A--GM---T- | ------------EL----------D----- | | ------K--M |
| 9¶ | -------T------ | VT | | -A--GM---T- | --------L---EL---------------- | | |
| 10* | -------T------ | VT | | -A--GM---T- | --------L---EL---------------- | | ------M-- |
| 11 | -------T------ | -VT | | ----GM---T- | --------L---EL---------------- | | ------P-- |
| 12 | -------T------ | -VT | | -A--GM---T- | --------L---EL---------------- | | ------R-- |
| 13 | -------T------ | -VT | | ----GM---T- | --------L---EL---------------- | | ------R--M |
| 14 | -------T------ | -VT | | -A--GM---T- | --------L---EL---------------- | | ------K-- |
| 15 | | | | | ------------E----------------- | --T-- | ------K-- |
| 16§ | ------TT------ | VT | | ----GM---T- | ------------EM---------------- | | |
| 17 | --TT---------- | -VT | | ----GM---T- | ------------EM---------------- | | ------R-M |
| 18 | -----A------- | -T- | | ----GM---T- | ------------EM---------------- | | |
| 19† | E---R---T------ | VT | | -A--GM---T- | --------L---EM---------------- | --TT-- | ------K-- |
| 20‡ | E------T------ | VT | | -A--GM---T- | ------------EL----------D----- | | |
| 21 | E------T------ | VT | | -A--GM---T- | ------------EL----------D----- | | ------M-- |
| 22 | E------T------ | VT | | ----GM---T- | ------------EL----------D----- | | ------K-- |
| 23§ | E------T------ | VT | | -A--GM---T- | --------L---EL----------D----- | | |

TABLE 6-continued (SEQ ID NOS 177, 181, 184, 239-241, 186, 242, 188-190, 243-247, 197, 248-249, 207, 211-218, 250, 219, 251, 225, 252-253, 232, 254, 234, and 237, respectively, in order of appearance)

| | | | | | | | | | |
|---|---|---|---|---|---|---|---|---|---|
| 24§ | E | I | VT | | A | GM | T | L | EL | | K |
| 25* | E | I | VT | | A | GM | T | L | EL | | K-M |
| 26* | E- | -T- | -VT | | -A- | GM- | -T- | -L- | -EL- | | ---K-T--- |
| 27† | E- | -T- | -VT | | -A- | GM- | -T- | -L- | -EL- | | R |
| 28 | E- | -T- | -VT | | | GM- | -T- | -L- | -EL- | -N- | |
| 29† | E- | -T- | -VT | | | GM- | -T- | | -EM- | | R |
| 30 | E- | -TT- | -VT | | | GM- | -T- | | -EM- | | ---R-M--- |
| 31 | E- | -TT- | -VT | | | GM- | -T- | | -EM- | | ---K-M--- |
| 32† | M | -T- | -VT | | -A- | GM- | -T- | -L- | -EL- | | |
| 33 | ---E | -T- | -VT | | -A- | GM- | -T- | -L- | -EL- | | ---E-T--- |
| 34* | Q | -T- | -VT | | -A- | GM- | -T- | -L- | -EL- | | M |
| 35* | Q | R | VT | | | GM | T | L | EM | TT | M |

In Table 6, antibody regions and Kabat numbering ranges are listed at the top of each sequence column. (*—paired with 2 unique light chains, †—paired with 3 unique light chains, ‡—paired with 4 unique light chains, §—paired with 5 unique light chains, ¶—paired with 13 unique light chains).

Figure 7:
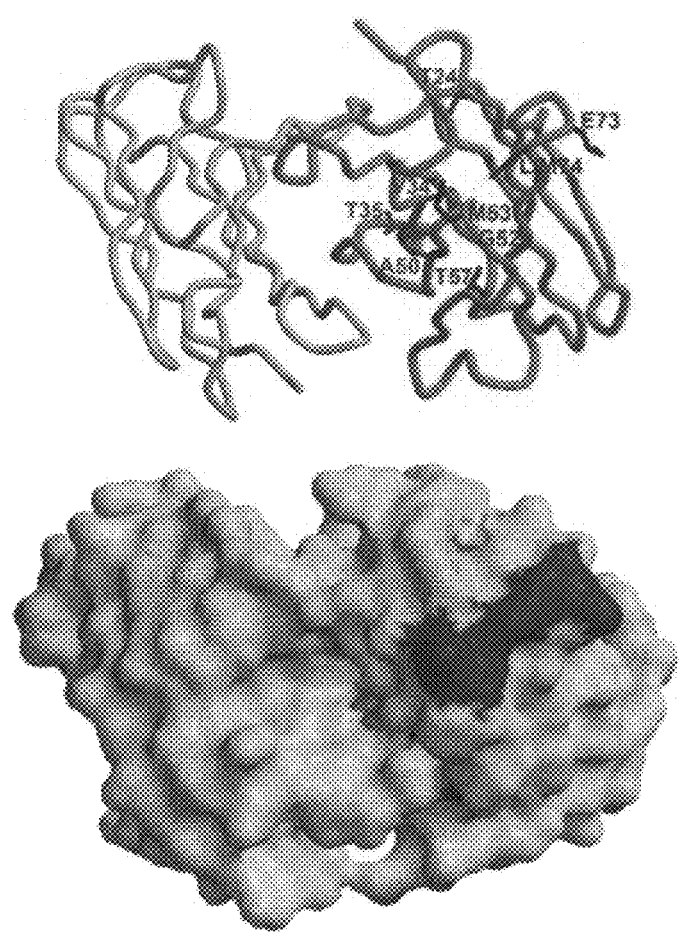
FIG. 7 shows the positions of H5 hemagglutinin binding Group 1 required and dominant mutations on the crystal structure of Fab 47e.
Figure 8:
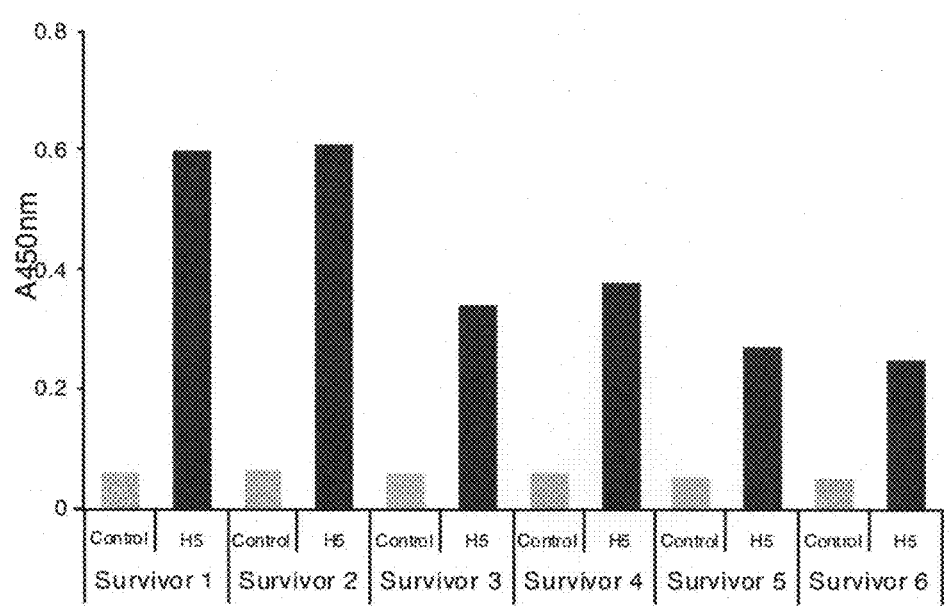
FIG. 8 shows the cross-reactive titers of Turkish avian influenza survivors to the H5N1 Vietnam 1203/04 hemagglutinin protein.
Figure 9:
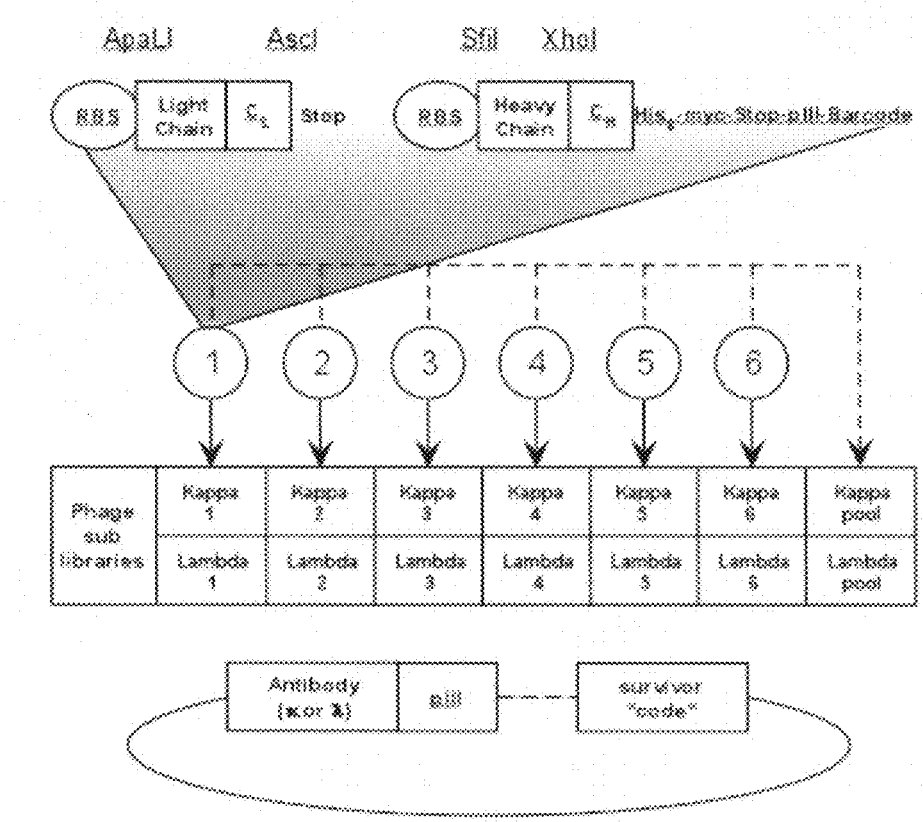
FIG. 9 illustrates the cloning and barcoding of annotated repertoires. 'His6' disclosed as SEQ, ID NO: 173.

FIG. 7 shows the positions of the required mutations in the structure of the antibody superimposed on the crystal structure of a highly related anti-HIV Fab called 47e (1rzi.pdb) (Huang, C. C. et al. (2004) *Proc. Nat. Acad. Sci.* 101, 2706-2711). FIG. 7 shows the positions of H5 hemagglutinin binding Group 1 required and dominant mutations on the crystal structure of Fab 47e. The required mutations are shown as G52 (52A (Pro>Gly)), M53 (Ile>Met), T57 (Ala>Thr), E73 (Lys>Glu) and LM74 (Ser>Leu or Met). The dominant mutations are shown as T24 (Ala>Thr), V34 (Ile>Val), T35 (Ser>Thr), and A50 (Gly>Ala). The required and dominant Group1 heavy chain sequences identified in H5 Vietnam/1203/2004 HA biopanning are superimposed on the crystal structure of the highly related anti-HIV Fab 47e. Mutations are shown in both backbone (top) and space-filling (bottom) models. A tight cluster is formed by four of the required mutations in and adjacent to CDR2. The required mutations 52A (Pro>Gly), 53 (Ile>Met), 73 (Lys>Glu) and 74 (Ser>Leu or Met) form a remarkably tight cluster on the exposed surface of the heavy chain variable domain where they form a ridge that prominently protrudes from the protein surface (FIG. 7). The remaining required mutation 57 (Ala>Thr) is partially buried at the base of the CDR2 loop. The surface exposed changes in CDR 2 and framework 3 are likely to have a direct role in antigen binding while the less exposed required mutation and the non-essential dominant mutations may have indirect effects through stabilizing and/or positioning the CDR2 loop.

The antibodies from survivor 2 are comprised of 2 unique heavy chains that most closely resemble the $V_H$4-4-b germ line heavy chain (Table 7). The first heavy chain has been found paired with 5 unique lambda light chains, four of which are from the infrequently used lambda 6 light chain family and the other is paired with a single kappa light chain. Antibody 4 whose neutralization profile was more restricted came from this group.

TABLE 7

(SEQ ID NOS 255-262, respectively, in order of appearance)

| Group 2 | FR1 (1-29) | CDR1 (30-35) | FR2 (36-46) | CDR2 (47-58) |
|---|---|---|---|---|
| Heavy chain | QVQLQESGPGLVKPSETLSLTCTVSGYSF | DSGYYWG | WLRQPPGKGLE | WIGSIYHSRNTY |
| Lambda light chains | FMLTQPHSVSESPGKTVTISCTGSGGN | IARNYVQWY | QQRPGSAPV | TVILEDDKRP |
|  | FMLTQPHSVSESPGKTVTISCTGSSGS | IASNYVQWY | QQRPGSAPT | TVIYEDYQRP |
|  | SVLTQPPSASGTPGQRVTISCSGSSSN | IGSNTVNWY | KQLPGTAPR | LLIYSNDQRP |
|  | SVLTQPPSASGTPGQRVTLSCSGSSSN | IGGNSVNWY | QHVPGTAPK | LLMHSDDQRP |
|  | PELTQPHSVSESPGKTVTISCTGSGGR | IATNHVQWY | QQRPGSAPT | IVIYENNQRP |
|  | PELTQPPSASGTPGQRVTISCSGSSSN | IGSNTVNWY | QQLPGTAPK | LLIYSNNQRP |
| Kappa light chain | DIQMTQSPSSLSAFVGDRVTITCQASQDI | SNYLNWY | QQKPGKAPK | LLIYDATNLE |

| Group 2 | FR3 (59-92) | CDR3 (93-101) | FR4 (102-113) |
|---|---|---|---|
| Heavy chain | YNPSLKSRVTISVDTSKNQFSLQLSSVTAADTAVYYC | ARGTWYSSNLRYWFD | PWGKGTLVRVSS |
| Lambda light chains | SGIPDRFSGSIDRSSNSASLTISGLRTEDEALYYC | QSYDDSDLV | VFGGGTKLT |
|  | SGVPDRFSGSIDSSSNSASLTISGLKTEDEADYYC | QSYDDSDHL | IFGGGTKLTVL |
|  | SGVPDRFSGSKSGTSASLAISGLQSEDEANYYC | AAWDDSLSGW | VFGGGTKLTVL |
|  | SGVPDRFSGSKSGTSXSLAISGLQSEDEADYYC | AXWDDSLNAW | VFGGXTKVTVL |
|  | SGVPNRFSGSIDDSSNSASLTISALRTEDEADYYC | QSADATNV | FFGGGTKVTVL |
|  | SGVPDRFSGSKSGTSASLAISGLQSEDEADYYC | AAWDDSLNGW | VFGGXTKLTVL |
| Kappa light chain | TGVPSRFSGSGSGTDFTFTISSLQPEDIATYYC | QQYDNLPL | TFGGGTKVDIKR |

The probability that a given mutation is important to the activity of an antibody increases as a function of the number of times it was independently selected. To determine if the required mutations were selected during somatic mutation from independent clones or were from the progeny of a single clone that further mutated during subsequent replications, the codon usage of the dominant mutations were analyzed (Table 8A-8B). The data reveal that although different codons were used they resulted in the same amino acid changes, demonstrating that these mutations arose independently in different clones and were, thus, selected multiple times. This convergent outcome for independently selected events is strong evidence that these dominant mutations play a critical role in the binding to the virus and/or its neutralization.

As illustrated in Table 8A-8B, codon usage of individual clones shows independent origin of selected H5 HA binding clones. DNA alignment and encoded amino acids for 6 representative Group 1 antibodies against the VH1-e germline. The use of different codons for the same amino acids demonstrates that each unique sequence is of a distinct origin. Table 8A corresponds to CDR2 and Table 8B corresponds to Framework 3. Germ line codons are shown as bolded codons. A change from a germ line codon to the same amino acid is shown as a plain text codon. A first change from a germ line amino acid is shown as a bolded, underlined codon. A second change from a germ line amino acid is shown as an italicized, underlined codon. A third change from a germ line amino acid is shown as an underlined, grayed-out codon.

pletely protective against lethal infection, even when given three days post inoculation in mice (Hanson, B. J. et al. (2006) *Respir Res* 7, 126). Given the possibility of a catastrophic epidemic, the way forward seems clear to many in the field. It

TABLE 8A (SEQ ID NOS 263-276, respectively, in order of appearance

| Clone Number | Kabat Sequence | CDR2 | | | | | | | | | | | | | |
|---|---|---|---|---|---|---|---|---|---|---|---|---|---|---|---|
| | | 47 | 48 | 49 | 50 | 51 | 52 | 52A | 52B | 52C | 53 | 54 | 55 | 56 | 57 | 58 |
| | VH1-e germline | TGG<br>W | ATG<br>M | GGA<br>G | AGG<br>R | ATC<br>I | ATC<br>I | CCT<br>P | ATC<br>I | CCT<br>L | GGT<br>G | ATA<br>I | GCA<br>A | AAC<br>N | TAC<br>Y | GCA<br>A |
| | 27 | TGG<br>W | ATG<br>M | GGC<br>G | GCG<br>A | ATC<br>I | ATC<br>I | GGT<br>G | ATG<br>M | TTT<br>F | GGT<br>G | ACA<br>T | ACA<br>T | AAC<br>N | TAC<br>Y | GCA<br>A |
| | 30 | TGG<br>W | ATG<br>M | GGA<br>G | *GGG*<br>*G* | ATC<br>I | ATC<br>I | GGT<br>G | ATG<br>M | TTT<br>F | GGA<br>G | ACA<br>T | *ACC*<br>*T* | AAC<br>N | TAT<br>Y | GCA<br>A |
| | 33 | TGG<br>W | ATG<br>M | GGA<br>G | GCG<br>A | ATC<br>I | ATC<br>I | GGT<br>G | ATG<br>M | TTT<br>F | GGT<br>G | ACA<br>T | ACA<br>T | AAC<br>N | TAC<br>Y | GCA<br>A |
| | 41 | TGG<br>W | ATG<br>M | GGC<br>G | GCG<br>A | ATC<br>I | ATC<br>I | GGT<br>G | ATG<br>M | TTT<br>F | GGT<br>G | ACA<br>T | ACA<br>T | AAC<br>N | TAC<br>Y | GCA<br>A |
| | 50 | TGG<br>W | ATG<br>M | GGA<br>G | *GGG*<br>*G* | ATC<br>I | ATC<br>I | GGT<br>G | ATG<br>M | TTT<br>F | GGT<br>G | ACA<br>T | ACG<br>T | AAC<br>N | TAT<br>Y | GCA<br>A |
| | 17 | TGG<br>W | ATG<br>M | GGA<br>G | *GGG*<br>*G* | ATC<br>I | ATC<br>I | GGT<br>G | ATG<br>M | TTT<br>F | GGT<br>G | ACA<br>T | ACA<br>T | AAC<br>N | TAC<br>Y | GCA<br>A |
| | # Codons used | 1 | 1 | 2 | 2 | 1 | 1 | 1 | 1 | 1 | 2 | 1 | 3 | 1 | 2 | 1 |

TABLE 8B (SEQ ID NOS 277-290, respectively, in order of appreance)
Framework 3

| Clone Number | Kabat Sequence |
|---|---|
| | 67 68 69 70 71 72 73 74 75 76 77 78 |
| VH1-e germline | GTC ACG ATT ACC GCG GAC AAA TCC ACG AGC ACA GCC<br>V T I T A D K S T S T A |
| 27 | GTC ACG CTT ACC GCG GAC GAA *TTA* ACG TCC ACA GCC<br>V T L T A D E L T S T A |
| 30 | CTC ACA ATC ACC GCG GAC *GAG* ATG ACG TCC ACA GCC<br>L T I T A D E M T S T A |
| 33 | GTC ACA ATC ACC GCG GAC GAA *TTA* ACG TCC ACA GCC<br>V T I T A D E L T S T A |
| 41 | GTC ACG CTT ACC GCG GAC GAA *TTA* ACG TCC ACA GCC<br>V T L T A D E L T S T A |
| 50 | GTC ACG ATT ACC GCG GAC *GAG* ATG ACG TCC ACA GCC<br>V T I T A D E M T S T A |
| 17 | GTC ACG ATT ACC GCG GAC GAA *TTA* ACG TCC ACA GCC<br>V T I T A D E L T S T A |
| # Codons used | 2 2 3 1 1 1 2 2 1 1 1 1 |

The present report raises two central issues relative to the prevention and treatment of infections caused by the avian influenza neutralized virus. The first concerns the importance of antibodies relative to other components of the immune system. While it has been known for over 80 years that passive administration of immune sera can prevent infection Luke, T. C. et al., Kilbane E M, Jackson J L, & Hoffman S L (2006) *Ann Intern Med* 145, 599-609), more recent studies with monoclonal antibodies also offer encouragement (Hanson, B. J. et al. (2006) *Respir Res* 7, 126; Huang, C. C. et al. (2004) *Proc. Nat. Acad. Sci.* 101, 2706-2711; Simmons C. P. et al. (2007) *PLoS Med* 4, e178). For example, Hanson et. al. showed that a monoclonal antibody to H5N1 virus was com- has been suggested that governments should maintain stocks of neutralizing antibodies such as those reported here. The facts that our antibodies are fully human and have been isolated from individuals who successfully combated viral infection may offer advantages. However, even if such antibodies are stockpiled, hurdles remain. For instance, if the gene encoding the epitope to which the antibody binds were to mutate, then the antibody might be less effective. Also, there is some evidence that cellular immunity enhances clearance of the virus. Nevertheless, if the only effect of passive immunization was to lessen the severity of infection, thereby giving the necessary time for other immune effectors to operate, it could be of critical importance for lessening mortality in patients with weakened immune, cardiovascular, and respiratory systems and in the elderly. Passive immunization might prevent the cytokine storm against rapidly proliferating virus, as occurred even in healthy young adults during the 1918 influenza outbreak.

The second important feature of this report relates to the special advantages that antibodies from combinatorial libraries bring to the problem (Lerner R A (2006) *Angew Chem Int Ed Engl* 45, 8106-8125). The most general aspect is that, because such libraries are nucleic acid based, they are not are not dependant on whether an important antibody is currently being produced. This obviates any concern about when in the course of the disease the sample was obtained. Indeed, as is the case here, when the source of antibody genes is the bone marrow, the entire immunologic history of an individual's antibody response may be obtained, irrespective of whether an antibody is actively expressed or is stored in the memory compartment. Thus, in the analysis of antibody ontogeny in the individuals studied here, the time factor is eliminated and one can get a clearer view of the precursor product relationships between related antibodies. In this respect, one of the most remarkable features of some of our antibody collections (i.e. group 1) is that the required somatic mutations are confined to framework 3 or CDRH2 rather than CDRH3 where they would be most expected to occur. This may be because the extreme virulence of the virus imposes time pressure on the evolution of the immune response. To survive an H5N1 avian influenza virus infection, one must mount an effective immune response rapidly. Because the framework regions and CDR2 of the protein are structurally rather constrained, the evolutionary search of sequence space for increased binding energy through somatic mutation may be more efficient for these regions than for a similar search through the more flexible and diverse CDR3 region. Indeed, it is well known, mostly from attempts to humanize antibodies, that framework mutations can directly or indirectly affect binding energy and/or specificity (Foote J & Winter G, (1992) J Mol Biol 224, 487-499; Holmes, M. A. et al. (2001) J Immunol 167, 296-301). Alternatively, the immune system may use frameworks and/or CDRs that have been previously optimized, perhaps in response to an earlier exposure to a similar virus. Regardless of the exact mechanism, our results are in broad agreement with those of Zinkernagel and colleagues who studied the immune response against lethal vesicular stomatitis virus infections in mice (Kalinke U et al. (1996) *Immunity* 5, 639-652; Kalinke U et al., (2000) *Proc Natl Acad Sci USA* 97, 10126-10131). In their studies, only one $V_H$ germline gene was used and the primary neutralizing immune response was devoid of somatic mutations. Only later did somatic mutations in the CDRs appear. It should be emphasized that while our analysis to date has revealed many interesting antibodies, we have so far only analyzed a small fraction of the library. As further analyses are carried out, we expect to see many other immunochemical solutions to the problem of virus infection.

From an antibody engineering point of view, the large database unique to antibody libraries creates a roadmap for improving the binding energy and/or specificity of the antibodies, if necessary. For example, one understands immediately that there are heavy chains (Tables 1, 2, and SI4) that are highly promiscuous with respect to their light chain partners. These heavy chains are ideal for light chain shuffling experiments where very large numbers of new light chains are paired with a single promiscuous heavy chain (Lerner R A (2006) *Angew Chem Int Ed Engl* 45, 8106-8125; Kang, A. S. et al. (1991) *Proc Natl Acad Sci USA* 88, 11120-11123). Ultimately, the best features of different antibodies can be amalgamated into a single antibody that can be highly effective and even overcome viral escape by mutation. This is especially likely when consensus sequences important to neutralization occur either in the different antibody chains or in different CDRs or frameworks within a chain or both. Thus, many combinations can be tested and an amalgamated antibody could contain the best elements of these various loops and frameworks. Critically, when some of the features incorporated into the amalgamated antibodies represent alternative binding modes to a neutralization target on the virus, one would expect viral escape to be more difficult.

There is another feature that derives from the large numbers of antibodies obtained from libraries that may be of particular importance to the influenza problem. Many, if not most, of the antibodies that result from an infection have little to do with prevention of further infectivity and are simply a response to the foreign nature of the virus. Thus, if one has only a few antibodies to choose from, one might miss the most important rare antibodies because they are under-represented in the bulk immune response. Indeed, this may be a feature of the most potent antibodies since they need only be present in small concentrations and/or may occur late in an infection only after many other "attempts" were tried during the evolution of an immune response. We have seen this phenomenon in human libraries from cancer patients where antibodies that prevent metastasis are present at the very rare frequency of about one out of $1.0 \times 10^8$ library members (Felding-Habermann B, et al. (2004) *Proc Natl Acad Sci USA* 101, 17210-17215). The features that one might screen for that would be expected to be rare are, for example, antibodies that exhibit broad neutralization or have unusual access to important tissue compartments. Toward this end, it will be interesting to see if there are any neutralizing antibodies in our collection of clones that bind virus but are not directed to the hemagglutinin.

The analysis of the immune response from actual cases can give guidance for both new passive antibody therapy and vaccine design. For example, we already know that patients make antibodies against the hemagglutinin that are broadly reactive between H5 and H1 strains, but skip H3. We could not learn this from simple serology because serum contains a collection of activities as seen here for our patients and, thus, it is impossible to determine the clonal basis of any reactivity from an analysis of sera. The localization of the cross-reactive epitopes already found here as well as others is now relatively straight forward using antibodies from the library as a guide. Access to multiple antibodies from several survivors of the viral infection also enables the mapping of common epitopes, other than hemagglutinin, to which all survivors have developed high affinity antibodies. The knowledge of several previously unknown epitopes could provide the foundation for the design of novel vaccines.

Characterized neutralizing antibodies can also give information regarding the potential efficacy of candidate vaccines. For instance, one can determine if particular traditional or recombinant vaccine preparations generate antibody classes that have proven to be neutralizing from analysis of survivors of actual infections. Furthermore, these antibodies can be used as test reagents to ensure that epitopes that are important to neutralization are properly presented in the vaccine constructs. While this later point might seem trivial, there has heretofore been no simple way to learn whether critical epitopes are destroyed during construction of subunit vaccines or even during formulation of intact virus preparations.

Finally, we come to the often asked interesting question of whether it matters that the libraries were prepared from patients who successfully combated an infection as opposed to animals or people that simply have been immunized with viral antigens. Because a substantial fraction of patients in our cohort died, it is tempting to speculate that the survivors made antibodies that were related to their favorable clinical outcome. This is a difficult argument because so many factors contribute to patient survival, several of which have little to do with the robustness of the immune response. It simply should be said that natural antibodies obtained from survivors can reasonably be expected to be at least as good as, and perhaps better, than those obtained after simple immunization with inert antigens. At the very least, one can be certain that the virus has been presented in a manner that allowed an immune response appropriate to survival of the individual. Thus, we gained insight from this analysis about how the immunological repertoire searches sequence space when, because of the virulence of the infectious agent, time is short.

Materials and Methods

H5N1 Turkish cases—bone marrow recovery. Six H5N1 survivors provided bone marrow and serum for this study. All were diagnosed between December 2005 and January 2006. Descriptions of their diagnoses have been previously reported (Oner et al., (2006) N. Engl. J. Med. 355:2179-2185). Briefly, most samples were nasopharyngeal swabs tested by ELISA, rapid influenza test, and/or real-time polymerase chain reaction in Turkey. Additionally, four of the six survivors were further verified by WHO laboratory testing in London. Following four and five months post recovery bone marrow aspirates and serum from the six survivors were collected, minimally processed in RNALater (Ambion) to preserve RNA integrity, and shipped frozen on dry ice to our laboratories. This study was reviewed and approved by both the Turkish Ministry of Health and the Yuzuncu Yil University, Van, Turkey. Written guardian consent was provided for all donors.

Antibodies, Proteins and viruses. Hemagglutinin proteins were either purchased from Protein Sciences (H5 Protein A/Vietnam/1203/2004, H1 Protein A/New Calcdonia/20/99, H3 Protein A/Wisconsin/67/05) or generated by de novo synthesis (H1 Protein A/South Carolina/1/18) as eukaryotic codon optimized soluble secreted HA genes (DNA 2.0) and then subcloned into pCI (Promega) for mammalian protein expression, sequence verified, and then transfected into 293 Freestyle cells (Invitrogen) according to manufacturers guidelines. Briefly 20 μg of light chain and 10 μg heavy chain encoding plasmid were combined with 1.0 ml 293 fectin and incubated for 60 minutes. Following this preincubation the DNA mixture was combined with 3×107 cells in 30 ml media for then and the resulting cell suspension was grown according to manufacturers suggestion for 7 days. After seven days the secreted immunoglobulins were purified from the culture supernatents using protein A chromatography (Calbiochem). The resulting purified antibodies were buffer exchanged into sterile PBS using centrifugal size filtration (Centricon Plus-20) and their protein concentrations determined by colorimetric BCA assay (Pierce).

Recombinant viruses were genetically engineered and produced as described elsewhere (Fodor et al., (1999) J. Virol. 73:9679-9682). Additionally, Indonesia, Turkey, and Egypt were similarly made except their HA genes were synthetically assembled using eukaryotic codon optimized sequences (DNA 2.0). Inactivated viruses were made as described elsewhere (Fodor et al., supra).

Serology: Hemagglutinin and viral ELISA. Recombinant HA proteins: H5 Protein A/Vietnam/1203/2004 (Protein Sciences)-10 ng/well; Recombinant HA H1 Protein A/New Calcdonia/20/99(Protein Sciences)-10 ng/well; Recombinant HA H3 Protein A/Wisonsin/67/05 (Protein Sciences)-10 ng/well; H1N1 Virus A/New Calcdonia (BioSource)-70 ng/well; H3N2 Virus A/Panama/2007/99 (BioSource)-10 ng/well; FDA Influenza Virus Vaccine for H5N1 rgA/Vietnam/1203/2004 (CBER)-10 ng/well.

ELISA plates were coated as indicated with either recombinant hemagglutinin protein or inactivated virus overnight incubation at room temperature. The next day plates were appropriately blocked (1% bovine serum albumin in PBS/0.05% Tween-20) and then 0.1 ml serum samples, diluted in blocking buffer, were incubated, washed, and detected using a peroxidase conjugated anti-human Fc antibody (Jackson Immuno) and TMB detection (BioFX). Absorbance at 450 nm was read, data recorded, and reported herein.

Donor specific repertoire recovery. Between 2-2.5 ml of donor bone marrow previously stored in 25 ml RNAlater (Ambion) was processed with TRI-BD (Sigma) according to manufacturers directions and then further processed to extract purified total RNA as described elsewhere (Barbas et al., (2001) Phage Display: A Laboratory Manual (Cold Spring Harbor Lab Press, Cold Spring Harbor, N.Y.)). Next mRNA was purified by Oligotex spin column purification (Qiagen). Next random nonamer primed reactions and oligo dT reverse transcription reactions performed using Accuscript (Stratagene) according to manufacturers directions.

For each donor the following was performed. For each of the 11 lambda light chain families a single PCR amplification was performed with family specific $V_L$ primers, a mixture of $J_L$ primers, and primed with 75 ng Oligo dT cDNA. Kappa recovery was similarly performed for each of the six kappa light families, except that 75 ng of random nonamer primed cDNA was used. For heavy chain recovery VH1/7, VH3, and VH4 were individually recovered, and VH 2, 5, and 6 were pool amplified with gene specific primers, a mixtures of $J_H$ primers, and each was primed with 100 ng of random nonamer primed cDNA. Primers and amplification conditions were essential as described elsewhere using Platinum Pfx polymerase (Invitrogen) (ref). PCR products were minimally processed by PCR Cleanup (Qiagen) quantitated by $A_{260}$. Heavy chain reactions were gel purified and then, if necessary, amplified again to produce quantities sufficient for cloning.

Phage Library Construction.

Light chain cloning. Donor specific barcoded vectors and equimolar pools of Kappa and lambda light chains were separately digested with NotI and BamHI and gel purified using (Qiagen). Library ligations were performed with 200 ng of gel purified Kappa or Lambda inserts and 1 μg of gel purified vector. Incubation is for at least one hour at RT or overnight at 14° C. Ligations were desalted using Edge BioSystem Perfroma spin columns. 5 electroporations per library were done in 80 μl TG-1 aliquots, each recovered in 1 ml SOC, pooled and outgrown for one hour at 37° C. A sample of each was taken for plating and used to determine the total number of transformants. The remainder was transferred to 200 ml 2YT+100 μg/ml Ampicillin+2% glucose and grown overnight at 37° C. Target number of transformants/library was at least $1\times10^6$/μg vector DNA. Light chain library plasmids were then pelleted and the plasmids purified using a Qiagen High Speed Maxiprep Kit.

Heavy chain cloning and phage production. Donor specific heavy chains ($V_H1$, $V_H3$, $V_H4$, and $V_H2$, 5, 6 pool) and light chain library collections were separately digested with a 40 Unit/μg DNA with SfiI and XhoI and gel purified (Qiagen). 5 μg of kappa and lambda light chain libraries were separately ligated, overnight, with 1.2 μg of an equimolar mix of the four donor specific heavy chain preparations. The library ligations were spin column desalted (Edge BioSystem) and then transformed in 16-20 electroporations per library. Processing to determine the number of transformants is as described above. Phage production proceeded as described elsewhere. Following phage production the phage was harvested by PEG/NaCl precipitation and resuspended and stored in PBS containing 50% glycerol.

Panning and Clonal ELISAs. Panning and clonal ELISAs were performed as described previously (Fodor, E. et al. J Virol. 1999; 73(11): 9679-82).

Microneutralization. Cross sub-type neutralization by antibodies recovered from survivors of avian influenza. Indonesia and Turkey hemagglutinin genes were synthetically assembled using human codon optimized sequences (DNA 2.0) and then used to generate recombinant engineered viruses. Recombinant influenza viruses were generated using reverse genetics as previously described (Fodor, E. et al. J Virol. 1999; 73(11): 9679-82). Briefly, 1 ug each of 10 plasmids was transfected into 293 T cells in monolayer. Each transfection contained ambisense plasmids (for the expression of both vRNAs and mRNAs) for the A/Puerto Rico/8/34/PA, PB1, PB2, NP, M, and NS segments, in addition to vRNA (pPOL1 type) and protein expression plasmids (pCAGGS type) for A/Vietnam/1203/04 HA and NA (pCAGGS expression plasmid was kindly provided by J. Miyazaki, Osaka University, Osaka, Japan) (Miyazaki, J. et al. Gene 1989; 79(2):269-77). Twenty hours following transfection, 293T cells were resuspended in cell culture supernatant, and used to inoculate 10-day-old embryonated eggs.

Antibodies were screened for neutralizing activity against viruses as follows. Two fold serial dilutions of each Mab were incubated with 100 $TCID_{50}$ of virus in PBS at 37° for 1 h. Madin-Darby Canine Kidney cell monolayers in 24 well plates were washed once with PBS and inoculated with virus-antibody mixtures. Following incubation for 1 h at 37° C. in 5% $CO_2$, the inoculum was removed and monolayers were again washed once with PBS. Opti-MEM supplemented with 0.3% BSA, 0.01% FBS and 1 ug/ml TPCK-treated trypsin was added and cells were incubated for 72 h at 37° C. The presence of virus in cell culture supernatants was assessed by HA assays using 0.5% chicken red blood cells.

Cross-reaction IgG ELISA. Microtiter plates were coated with 0.1 ml of the following antigens diluted in coating buffer and incubated overnight at room temperature: 100 ng/ml H5N1 Vietnam 1203/04, 250 ng/ml H5N1 Turkey/65596/06, 1 μg/ml H5N1 Indonesia/5/05, 700 ng/ml H1N1 New Caledonia/20/99, 1 μg/ml H1N1 North Carolina/1/18, 100 ng/ml and H3N2 Wisconsin/67/05. Blocking was done with 0.3 ml of blocking buffer (4% Non-fat dry milk in PBS/0.05% Tween-20). Following blocking antibodies diluted to 0.5 μg/ml in 2% non-fat dry milk blocking buffer were incubated for two hours at 4 C, washed, and later detected using a 1:3000 dilution of peroxidase conjugated anti-human $F_c$ antibody (Jackson ImmunoResearch) in 2% non-fat dry milk blocking buffer and standard TMB substrate detection (BioFX). Absorbance at 450 nm was read, data recorded, and reported herein. (B) Relative ranking of antibodies by their ELISA signal to noise ratios (−<2, +=2−<9, ++=9−<15, +++=≥15), on various proteins and minimal inhibitory concentration (MIC) in microneutralization assay. Suitable protocols can be found in Barbas C. et al. (2001) *Phage Display, A Laboratory Manual* (Cold Spring Harbor Laboratory Press).

Epitope Analysis of Hemagglutinin-Binding Fabs.

Biotinylation of HA Proteins: 100 ug of purified Hemagglutinin protein is biotinlyated at a 20:1 molar excess using Pierce No-Weigh PEO4 biotin (cat#21329) according to manufacturers instructions, incubated at room temperature for 1-3 hours with intermittent mixing and then incubated overnight at 4 C. The excess biotin is removed by size exclusion spin column and exchanged into PBS.

Quantitation of Fabs: HA binding Fabs are purified by FPLC using $Ni^{2+}$ affinity chromatography, desalted to remove excess imidazole, concentrated, and quantitated by quantitative light chain ELISAs (Bethel Labs, cat# E80-115-κ, and E80-116-λ) are performed according to the manufacturers instructions.

Sample set up: HA protein is bound to sensors and allowed to reach new baseline. Next, sample and epitope binding standards are tested for HA saturation using the conditions determined from kinetic analysis. Desalted, concentrated Fabs were evaluated for HA binding in a typical range of 0.5-16 ul in 200 ul sample diluent. Using the conditions identified in saturation testing, standard epitope binding antibodies are first loaded on to HA coated biosensors. A new baseline is established and then the test samples at half saturation concentrations are loaded on to the epitope saturated sensors. Antibodies are tested against all possible epitope recognition standards in this way. The following is a summary of the sample type and time the sensors are held in each column of solution:

| | | | |
|---|---|---|---|
| Column 1 | Baseline | Sample Diluent | 1-2 minutes |
| Column 2 | HA Binding | Biotinylated HA | 5-15 minutes |
| Column 3 | Baseline | Sample Diluent | 1-2 minutes |
| Column 4 | Saturation | Diluted antibodies | 5-15 minutes |
| Column 5 | Baseline | Sample Diluent | 1-2 minutes |
| Column 6 | Sample binding | Diluted test antibody | 5-15 minutes |
| Column 7 | Baseline | Sample Diluent | 1-2 minutes |

Increased interference shift above saturation levels indicates novel epitope recognition. Three possible results from this type of analysis are:

1) Complete blocking—No interference shift
2) Restoration of saturation—If dissociation of the standard occurs during the baseline after binding, sample binding that restores the signal to saturation levels indicates binding to the same epitope
3) New epitope binding—Increased interference shift above saturation levels Kinetic Analysis of Hemagglutinin-Binding Fabs.

Biotinylation of HA Proteins: 100 ug of purified Hemagglutinin protein is biotinlyated at a 20:1 molar excess using Pierce No-Weigh PEO4 biotin (cat#21329) according to manufacturers instructions, incubated at room temperature for 1-3 hours with intermittent mixing and then incubated overnight at 4 C. The excess biotin is removed by size exclusion spin column and exchanged into PBS.

Quantitation of Fabs: HA binding Fabs are purified by FPLC using $Ni^{2+}$ affinity chromatography, desalted to remove excess imidazole, concentrated, and quantitated by quantitative light chain ELISAs (Bethel Labs, cat# E80-115-κ, and E80-116-λ) are performed according to the manufacturers instructions.

Kinetic Analysis: Kinetic analysis is performed on a range of sample concentrations that are empirically determined. The first range is typically 15 nM-500 nM in serial 2 fold dilutions and the samples are incubated with biosensors coated with HA protein for up to 15 minutes, then incubated in sample diluent for up to 1 hour. All of these steps are done with sample plate rotation at 1500 RPM. Association is measured during the Fab incubation with the HA-coated biosensors and dissociation is measured in the sample diluent incubation following binding. The following is a summary of the sample type and time the sensors are held in each column of solution:

| Column 1 | Baseline | Sample Diluent | 1-2 minutes |
| Column 2 | HA Binding | Biotinylated HA | 5-15 minutes |
| Column 3 | Baseline | Sample Diluent | 1-2 minutes |
| Column 4 | Association | Diluted antibodies | 5-15 minutes |
| Column 5 | Dissociation | Sample Diluent | 15-180 minutes |

Data analysis using the Forte Bio Kinetic Analysis software provides estimates of on and off rates with $r^2$ values. A value is deemed to be reportable if of high confidence with $r^2$ values >0.95. The $k_D$ is then accepted as the affinity of the molecule.

Viral microneutralization. The VN activity of MAbs was measured as follows. MAb dilutions (50 ml) in ISC-CM-0.1% BSA, eight replicates per dilution, were dispensed into 96-well flat-bottom tissue culture plates. PR8 (50 ml) in ISC-CM-0.1% BSA (; 100 TCID50) were added to each well, and the plates were incubated for 1 h at 37° C. MDCK cells were then added to each well (25 ml ISC-CM-0.1% BSA containing 2 3 106 cells/ml), and the plates were incubated for 8 to 14 h to permit MDCK cells to adhere. The medium was then flicked out and replaced with 200 ml of antibody-free ISC-CM-0.1% BSA supplemented with trypsin (2.5% trypsin [Whittaker Bioproducts Inc.]) at a final dilution of 1/3,000 (; 8 mg/ml). After another 2.5 days of incubation, culture supernatants were tested for the presence of virus by HA titer determination. The MAb concentration at which 50% of the cultures were protected from infection was computed by interpolation and taken as the MAb VN activity. Note that low concentrations indicate high VN activity (Mozdzanowska, K. et al. (1997) J. Virol. 71, 4347-4355).

EXAMPLE 2

Generating Universal Influenza Vaccines

The goal of vaccine design against heterogeneous pathogens is to identify and design effective and broadly protective antigens. In the case of influenza, considerable historical efforts have gone into the empirical testing of conserved linear sequences and regions with little success. A plausible reason for these failures is a lack of knowledge that focused responses against antigenic test articles are actual bona fide productive sites for neutralization of an antigen on the pathogen in the setting of an actual infection. For influenza one would be expect to find these bona fide solutions within the repertoires of survivors of an influenza infection. In our case we have demonstrated that several related antibodies amongst a large collection of antibodies, derived from an H5N1 influenza survivor, (see Table 4 above) are capable of broadly neutralizing several subtypes of Influenza. These antibodies neutralize influenza through a novel mechanism that does not involve classical inhibition of hemagglutination, which has now been confirmed and delineated at a structural level by two additional and independent groups. Collectively, we expect that the design and assessment of vaccines utilizing such cross neutralizing antibodies derived from bona fide survivors would aid in the design and validity of cross reactive or "universal" influenza vaccines.

Specifically cross neutralizing monoclonal antibodies can be used in the design and validation of vaccine production processes that maintain or enhance the quality and antigenicity of cross neutralizing epitopes in current and future manufactured vaccines. Assuming that antibody binding to vaccine is reflective of structural integrity and antigenic potential, one would assess binding of cross neutralizing antibodies, such as Ab-1 (see Table 4 above) to such vaccine process derivatives to quantitatively assess their cross neutralizing potential.

To maximize the responses toward these universal epitopes one would create derivatives to increase immunogenicity towards these universal epitopes. In this case the resulting antigen would again be tested to insure that not only the efficiency of binding to target was maintained, but that a directed immunogenicity was accomplished. This would either involve determining the specific universal neutralizing titers contained in the serum from immunized individuals or test animals, likely by competitive ELISA against Ab-1 (or related antibody) from Table 4. As an in vitro surrogate, one would combine the antigen-antibody binding data with that of an in vitro or in silico predictive model for immunogenicity. To further direct responses to the universal epitope one may deimmunize known non-neutralizing hemagglutinin epitopes It reasonable to extend this antibody for the design and validation of engineered recombinant hemagglutinin chimeras, fragments, and conformational mimics. For instance, it is well established that influenza contains many immunodominant epitopes that give rise to non-neutralizing responses. Utilizing the cross protective antibodies it is possible to assess whether antigen variants of vaccines that have been partially or fully deimmunized for these immunodominant non-neutralizing epitopes have maintained or created enhanced recognition of the universally protective epitopes.

Additional ways to guide a specific response to a distinct epitope is to simply remove non-neutralizing and non-conserved regions from the recombinant vaccine design. As an example we would remove the HA1, or HA0 globular sialic binding domain of hemagglutinin to leave the more conserved stem region of hemagglutinin as the principal target for an immune response. As sequence space does not strictly correlate to physical space, this will require the removal of middle coding regions for proteins to create such aglobular constructs. Further as more of the globular domain is removed this will cause residues that are normally embedded within the protein structure to be exposed. These residues that are not normally solvent exposed may need to be mutagenized and deimmunized to residues that are better suited structurally or more compatible to solvent exposure. Similar to efforts described above, we would use the antibodies identified previously to insure the integrity of these cross protective epitopes.

From these aglobular vaccine designs, one could minimize the antigen epitopes and even remove them from the context of hemagglutinin to create a conformational cross specific antigen.

The strategies outlined above detail methods to guide a response to a minimized neutralizing epitope or element. From the knowledge of such minimized elements, which are likely be conformationally dependent and exist within discontinuous sequence space, it would be possible to recreate the conformational neutralizing epitope in a combinatorial fashion within a smaller polypeptide, as described previously (see Horowitz et al., Combinatorial Libraries of Conformationally Constrained Polypeptide Sequences, PCT/US2008/050877) where the proximal placement of discontinuous epitopes alone, or in the context of designed structural support, can regenerate the essential properties of conformational epitopes.

In such a design we would take the conformation epitope and express them on hemagglutinin related and unrelated structural scaffolds, or even as a collection of conformational epitopes within a library that could be selected by conformationally dependent antibodies such as Ab-1.

The reduction of discontinuous epitopes to a conformational epitope would result in an even smaller sized peptide immunogen than that possible with traditional protein engineering. Furthermore these structural epitopes may be further enhanced, reduced in size, or substituted through the use of nonpeptide mimetics. In any event, any of these conformational derivatives or mimics would be validated by the Ab-1, Ab-1 related antibody, or corresponding antibody to the influenza virus of choice.

Methods and materials. Influenza fusion epitope spore vaccine targets.
1. Mammalian expression of target as secreted protein or on mammalian cell.
   a. Express stem (HA2 only)
   b. aglobular HA0
   c. aglobular HA1/HA2
   d. aglobular HA1/topless HA2
2. Detect conformational epitope with A6-related antibody of secreted protein or on mammalian cell
3. Transfer successful stem or aglobular antigen to spore expression
4. Test for spore binding with A6-related antibody
5. Immunize mice

EXAMPLE 3

Increasing the Potency and Spectrum of Cross Subtype Neutralizing Antibodies

As mentioned previously, the group of cross subtype neutralizing antibodies that are partially represented by Ab-1, 2, & 3 contain very distinct and seemingly requisite heavy chain mutations within CDR2 and framework 3 (FR3), yet remarkably little to no diversity within CDR3. Considering the shear number of clones that were identified with these hallmark sequences, all of which were restricted to a 1-e, or 1-e like frameworks, leads one to suspect that this broad spectrum activity is principally driven by the this specific heavy chain framework and the CDR2 and Framework 3 (FR3) mutations. Recently, two groups have confirmed this at a structural level by analyzing co-crystals of hemagglutinin and other broad spectrum antibodies that utilize the 1-e like, 1-69 germline framework (Kashyap et al. supra; Throsby et al., PLoS ONE 3(12): e3942). In each instance the predominant binding was driven by CDR2 and FR3 sequence corresponding to the areas described by Kashyap et al. (supra). To identify minimal binding elements for this broad specificity one would begin by serially reverting back each of the CDR2 and FR3 mutations to germline and assess broad subtype influenza binding. In the case of CDR3, alanine scanning would be used to further define the crossreactive minimal essential elements.

Upon learning the range of sequence involved in broad specificity binding we would use methods of mutagenesis to create improved mutants for testing either individually or amongst a collection in a library. Methods commonly used to introduce mutations could be saturation mutagenesis at sites responsible for binding or error-prone PCR mutagenesis throughout the regions known to be responsible for binding. Similarly, the previously mentioned mutagenesis methods could be applied to other areas of the heavy chain that may influence recognition in a more global manner.

Once these 1-e or 1-e like optimized clones were identified we next utilize recombinant methods to graft these defined minimal elements onto other related and unrelated heavy chain frameworks. This gives us the ability to explore additional optimized solutions under different contexts that may be superior to the original. As a next step these minimal elements would be modeled and/or grafted onto other related and unrelated proteins. The success of these efforts could provide superior pharmacological agents and even avenues leading to minimized or constrained peptides that either present or mimic the crossreactive binding motif mimetic. Success at this stage would then be extended into the area of nonpeptide-mimetics.

Finally, searching the sequence databases for other related antibodies revealed numerous anti-infectious antibodies, suggesting the 1-e or 1-e like framework may function as a first line defense against infectious organisms and viruses. As such it is presumable that 1-e or 1-e like repertoires would be ideal sources for de novo identification of anti-infectious antibodies that could be developed similar to the outlined steps for the Ab-1 and related antibodies for influenza.

Materials and methods. 1-69/1-e anti-idiotype antibodies and vaccines.
1. Pan minimized framework element antibody for specific reagent.
2. Administer anti-idiotype antibody in presence or absence of B cell stimulating agent to expand anti-influenza repertoire.
3. Measure anti-influenza titer (ex vivo from PBMC or bone marrow).

EXAMPLE 4

Inducing 1-e and 1-e-Like Anti-Influenza Antibodies

Inducing the proliferation of memory B cells causes the proliferation and secretion of the specific antibodies the stimulated B cells. Presumably upon learning the minimal binding elements required for cross subtype hemagglutinin binding one could use this element as a selection tool to identify anti-idiotype antibodies. The administration of such a framework and mutation specific anti-idiotype antibodies would result in the expansion of these broad specific memory B cells and the serological increase of these anti-influenza antibodies in the setting of prophylaxis or treatment of disease.

Again, as searching the sequence databases for other related antibodies has revealed numerous anti-infectious antibodies, suggesting the 1-e or 1-e like framework may function as a first line defense against infectious organisms and viruses. It is presumable that expansion of 1-e or 1-e like anti-idiotype repertoires would be ideally suited for protection or treatment of infectious disease.

Agents to induce or produce broadly specific antibodies (1-69/1-e and related frameworks). Agents include rearranged Vh for delivered as gene therapy (in vivo & ex vivo), engineered transcriptional activators of Vh specific genes. Such agents would be useful for influenza (antiviral) treatment/prophylaxis; as an adjuvant for (antiviral) prophylaxis; ex vivo selection (and possible expansion) of Vh specific B cells for treatment and prophylaxis; influenza epitopes for Vh specific induction/production; 1-69/1-e and related anti-idiotype antibodies/surrobodies to expand Vh specific memory response (may include costimulatory agent on a surrobody or separate administration); vaccines directed to 1-69/1-e frameworks to induce proliferation and production of 1-69/1-e and related antibodies; and any combination of the above.

EXAMPLE 5

Co-Administration of Vaccine and Antibody to Increase Potency and Spectrum of Protection Complexes of antibody and antigen are known to potently induce responses against numerous microbial proteins and other proteins in animals. One possible explanation is that a forced uptake of the vaccine antibody complex occurs by Fc receptors on antigen presenting cells. Complexes of cross reactive antibodies, such as Ab-1 with seasonal vaccines would allow for increases in potency from year to year and because Ab-1 and the related antibodies recognize numerous hemagglutinin antigens, obviates the need to recreate new

```
Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Arg
            100                 105                 110

Gly Thr Met
        115

<210> SEQ ID NO 3
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Gln
            100                 105                 110

Gly Thr Met
        115

<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Arg
            100                 105                 110

Gly Thr Leu
        115
```

<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Lys
            100                 105                 110

Gly Thr Leu
        115

<210> SEQ ID NO 6
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Lys
            100                 105                 110

Gly Thr Leu
        115

<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Gln
            100                 105                 110

Gly Thr Leu
        115

<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Leu
        115

<210> SEQ ID NO 9
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

```
Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Ser Tyr Tyr Tyr Glu Ser Ser Leu Asp Tyr Trp Gly Lys
                100                 105                 110

Gly Thr Leu
        115

<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Gln Ser Gly Thr Glu Val Lys Lys Pro Gly Ser
 1               5                  10                  15

Ser Val Lys Val Ser Cys Lys Val Ser Gly Gly Thr Phe Ser Ser Tyr
                 20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Ser Tyr Tyr Tyr Glu Ser Ser Leu Asp Tyr Trp Gly Gly
                100                 105                 110

Gly Thr Thr
        115

<210> SEQ ID NO 11
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
                 20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                  55                  60

Gln Gly Arg Val Thr Ile Thr Ala Asp Glu Leu Thr Ser Thr Ala Tyr
 65                  70                  75                  80
```

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 12
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 13
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

```
<210> SEQ ID NO 14
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 15
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 16
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 16

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu
        115

<210> SEQ ID NO 17
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 18
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Gly Ala Phe Ser Ser Tyr
            20                  25                  30

Ala Val Thr Trp Val Arg Gln Ala Pro Gly Gln Gly Leu Glu Trp Met

```
                35                  40                  45
Gly Gly Ile Ile Gly Met Phe Gly Thr Thr Asn Tyr Ala Gln Lys Phe
        50                  55                  60
Gln Gly Arg Val Thr Ile Thr Ala Asp Glu Leu Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ser Tyr Tyr Tyr Glu Ser Ser Leu Asp Tyr Trp Gly Gln
            100                 105                 110
Gly Thr Met
        115

<210> SEQ ID NO 19
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Val Gln Ser Gly Ala Glu Val Lys Lys Pro Gly Ser
1               5                   10                  15
Ser Val Lys Val Ser Cys Lys Thr Ser Gly Gly Thr Phe Ser Ser Tyr
            20                  25                  30
Ala Val Thr Trp Val Arg Gln Ala Pro Gly Gln Gly Leu Glu Trp Met
        35                  40                  45
Gly Gly Ile Ile Gly Met Phe Gly Thr Thr Asn Tyr Ala Gln Lys Phe
        50                  55                  60
Gln Gly Arg Val Thr Met Thr Ala Asp Glu Met Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Ser Tyr Tyr Tyr Glu Ser Ser Leu Asp Tyr Trp Gly Lys
            100                 105                 110
Gly Thr Leu
        115

<210> SEQ ID NO 20
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Gln Ser Gly Ala Glu Val Lys Lys Pro Gly Ser
1               5                   10                  15
Ser Val Lys Val Ser Cys Lys Thr Ser Gly Gly Thr Phe Ser Ser Tyr
            20                  25                  30
Ala Val Thr Trp Val Arg Gln Ala Pro Gly Gln Gly Leu Glu Trp Met
        35                  40                  45
Gly Gly Ile Ile Gly Met Phe Gly Thr Thr Asn Tyr Ala Gln Lys Phe
        50                  55                  60
Gln Gly Arg Val Thr Ile Thr Ala Asp Glu Met Thr Ser Thr Ala Tyr
65                  70                  75                  80
Met Glu Leu Ser Ser Leu Arg Ser Glu Asp Thr Ala Val Tyr Tyr Cys
```

Ala Arg Gly Ser Tyr Tyr Tyr Glu Ser Ser Leu Asp Tyr Trp Gly Arg
                100                 105                 110

Gly Thr Leu
        115

<210> SEQ ID NO 21
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
                100                 105                 110

Gly Thr Met
        115

<210> SEQ ID NO 22
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu
        115

```
<210> SEQ ID NO 23
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Gln Ser Gly Ala Glu Val Gln Lys Pro Gly Ser
1               5                  10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 24
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Gln Ser Gly Ala Glu Val Lys Lys Pro Gly Ser
1               5                  10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 25
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25
```

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65              70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 26
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Gln Leu Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Leu
        115

<210> SEQ ID NO 27
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

```
Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Ser Tyr Tyr Tyr Glu Ser Ser Leu Asp Tyr Trp Gly Lys
                100                 105                 110

Gly Thr Leu
        115

<210> SEQ ID NO 28
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Ser Tyr Tyr Tyr Glu Ser Ser Leu Asp Tyr Trp Gly Lys
                100                 105                 110

Gly Thr Thr
        115

<210> SEQ ID NO 29
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Gly Ser Tyr Tyr Tyr Glu Ser Ser Leu Asp Tyr Trp Gly Lys
            100                 105                 110

Gly Thr Leu
        115

<210> SEQ ID NO 30
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Met
        115

<210> SEQ ID NO 31
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser
        115

<210> SEQ ID NO 32

<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Met Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Met Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser
        115

<210> SEQ ID NO 34
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65              70                  75                  80

Met Glu Leu Ser Ser Leu Arg Ser Glu Asp Thr Ala Val Tyr Tyr Cys
            85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 35
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65              70                  75                  80

Met Glu Leu Ser Ser Leu Arg Ser Glu Asp Thr Ala Val Tyr Tyr Cys
            85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 36
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

```
Gly Ala Ile Ile Gly Met Phe Gly Thr Thr Asn Tyr Ala Gln Lys Phe
            50                  55                  60

Gln Gly Arg Val Thr Leu Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Ser Ser Leu Asp Tyr Trp Gly Gln
                100                 105                 110

Gly Thr Leu
        115

<210> SEQ ID NO 37
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ser
 1               5                  10                  15

Ser Val Lys Val Ser Cys Lys Thr Thr Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Gly Ile Ile Gly Met Phe Gly Thr Thr Asn Tyr Ala Gln Lys Phe
         50                  55                  60

Gln Gly Arg Val Thr Ile Thr Ala Asp Glu Met Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Ser Ser Leu Asp Tyr Trp Gly Lys
                100                 105                 110

Gly Thr Leu
        115

<210> SEQ ID NO 38
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Leu Gln Ser Gly Ala Glu Val Lys Lys Pro Gly Ser
 1               5                  10                  15

Ser Val Lys Val Ser Cys Lys Thr Thr Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Gly Ile Ile Gly Met Phe Gly Thr Thr Asn Tyr Ala Gln Lys Phe
         50                  55                  60

Gln Gly Arg Val Thr Ile Thr Ala Asp Glu Met Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

```
Ala Arg Gly Ser Tyr Tyr Tyr Glu Ser Ser Leu Asp Tyr Trp Gly Lys
            100                 105                 110

Gly Thr Leu
        115

<210> SEQ ID NO 39
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 40
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 41
<211> LENGTH: 115
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 42
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Thr Ser Gly Gly Ser Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 43
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ser
```

```
                 1               5                  10                 15
Ser Val Lys Val Ser Cys Lys Thr Ser Gly Gly Thr Phe Ser Ser Tyr
                20                 25                 30

Ala Val Thr Trp Val Arg Gln Ala Pro Gly Gln Gly Leu Glu Trp Met
                35                 40                 45

Gly Gly Ile Ile Gly Met Phe Gly Thr Thr Asn Tyr Ala Gln Lys Phe
            50                 55                 60

Gln Gly Arg Val Thr Ile Thr Ala Asp Glu Leu Arg Ser Thr Ala Tyr
 65                 70                 75                 80

Met Glu Leu Ser Ser Leu Arg Ser Glu Asp Thr Ala Val Tyr Tyr Cys
                85                 90                 95

Ala Arg Gly Ser Tyr Tyr Tyr Glu Ser Ser Leu Asp Tyr Trp Gly Gln
               100                105                110

Gly Thr Leu
       115

<210> SEQ ID NO 44
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ser
 1               5                  10                 15

Ser Val Lys Val Ser Cys Lys Thr Ser Gly Gly Thr Phe Ser Ser Tyr
                20                 25                 30

Ala Val Thr Trp Val Arg Gln Ala Pro Gly Gln Gly Leu Glu Trp Met
                35                 40                 45

Gly Gly Ile Ile Gly Met Phe Gly Thr Thr Asn Tyr Ala Gln Lys Phe
            50                 55                 60

Gln Gly Arg Val Thr Ile Thr Ala Asp Glu Leu Thr Ser Thr Ala Tyr
 65                 70                 75                 80

Met Glu Leu Ser Ser Leu Arg Ser Glu Asp Thr Ala Val Tyr Tyr Cys
                85                 90                 95

Ala Arg Gly Ser Tyr Tyr Tyr Glu Ser Ser Leu Asp Tyr Trp Gly Gln
               100                105                110

Gly Thr Leu
       115

<210> SEQ ID NO 45
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ser
 1               5                  10                 15

Ser Val Lys Val Ser Cys Lys Thr Ser Gly Gly Thr Phe Ser Ser Tyr
                20                 25                 30

Ala Val Thr Trp Val Arg Gln Ala Pro Gly Gln Gly Leu Glu Trp Met
                35                 40                 45

Gly Gly Ile Ile Gly Met Phe Gly Thr Thr Asn Tyr Ala Gln Lys Phe
```

```
                50                  55                  60
Gln Gly Arg Val Thr Ile Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Ser Ser Leu Asp Tyr Trp Gly Arg
                100                 105                 110

Gly Thr Leu
        115

<210> SEQ ID NO 46
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Ser Ser Leu Asp Tyr Trp Gly Gln
                100                 105                 110

Gly Thr Met
        115

<210> SEQ ID NO 47
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Gly Ser Tyr Tyr Tyr Glu Ser Ser Leu Asp Tyr Trp Gly Gln
```

```
Gly Thr Leu
        115

<210> SEQ ID NO 48
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu
        115

<210> SEQ ID NO 49
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 50
<211> LENGTH: 115
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 50

Gly Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Glu Ser Ser Leu Asp Tyr Trp Gly Arg
            100                 105                 110

Gly Thr Leu
        115

<210> SEQ ID NO 51
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Lys
            100                 105                 110

Gly Thr Met
        115

<210> SEQ ID NO 52
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
50                      55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 53
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
50                      55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 54
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
50                      55                  60
```

```
Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met
        115

<210> SEQ ID NO 55
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Asn Ser Leu Asp Tyr Trp Gly Lys
            100                 105                 110

Gly Thr Leu
        115

<210> SEQ ID NO 56
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110
```

Gly Thr Met
        115

<210> SEQ ID NO 57
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met
        115

<210> SEQ ID NO 58
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Met
        115

<210> SEQ ID NO 59
<211> LENGTH: 115
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 59

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Lys
            100                 105                 110

Gly Thr Met
        115

<210> SEQ ID NO 60
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Lys
            100                 105                 110

Gly Thr Thr
        115

<210> SEQ ID NO 61
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Tyr Ser Phe Asp Ser Gly
            20                  25                  30

Tyr Tyr Trp Gly Trp Leu Arg Gln Pro Pro Gly Lys Gly Leu Glu Trp
        35                  40                  45

Ile Gly Ser Ile Tyr His Ser Arg Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Gln Leu Ser Ser Val Thr Ala Ala Asp Thr Ala Val Tyr Tyr Cys
                85                  90                  95

Ala Arg Gly Thr Trp Tyr Ser Ser Asn Leu Arg Tyr Trp Phe Asp Pro
            100                 105                 110

Trp Gly Lys Gly Thr Leu
            115

<210> SEQ ID NO 62
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Glu Ser Gly Pro Gly Gln Val Lys Pro Ser Glu
1               5                   10                  15

Thr Leu Ser Leu Thr Cys Thr Val Ser Gly Tyr Ser Phe Asp Ser Gly
            20                  25                  30

Tyr Tyr Trp Gly Trp Leu Arg Gln Pro Pro Gly Lys Gly Leu Glu Trp
        35                  40                  45

Ile Gly Ser Ile Tyr His Ser Arg Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Gln Leu Ser Ser Val Thr Ala Ala Asp Thr Ala Val Tyr Tyr Cys
                85                  90                  95

Ala Arg Gly Thr Trp Tyr Ser Ser Asn Leu Arg Tyr Trp Phe Asp Pro
            100                 105                 110

Trp Gly Lys Gly Thr Thr
            115

<210> SEQ ID NO 63
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Val Gln Leu Val Gln Ser Gly Ala Ala Val Lys Lys Pro Gly Ser
1               5                   10                  15

Ser Val Lys Val Ser Cys Lys Ala Ser Gly Gly Arg Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Gly Met Phe Gly Thr Thr Asp Tyr Ala Gln Lys Phe
    50                  55                  60
```

```
Gln Gly Arg Val Thr Ile Thr Ala Asp Glu Val Thr Ser Thr Gly Tyr
65                  70                  75                  80

Met Glu Leu Arg Ser Leu Thr Ser Glu Asp Thr Ala Val Tyr Tyr Cys
                85                  90                  95

Ala Arg Gly Ser Gly Tyr His Leu Gln Asn Pro Phe Asp Leu Trp Gly
            100                 105                 110

Arg Gly Thr Met
        115

<210> SEQ ID NO 64
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Gln Gln Ser Gly Ala Ala Val Lys Lys Pro Gly Ser
1               5                   10                  15

Ser Val Lys Val Ser Cys Lys Ala Ser Gly Gly Arg Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Gly Met Phe Gly Thr Thr Asp Tyr Ala Gln Lys Phe
    50                  55                  60

Gln Gly Arg Val Thr Ile Thr Ala Asp Glu Val Thr Ser Thr Gly Tyr
65                  70                  75                  80

Met Glu Leu Arg Ser Leu Thr Ser Glu Asp Thr Ala Val Tyr Tyr Cys
                85                  90                  95

Ala Arg Gly Ser Gly Tyr His Leu Gln Asn Pro Phe Asp Leu Trp Gly
            100                 105                 110

Lys Gly Thr Leu
        115

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Ile Trp Val Arg Gln Val Pro Gly Lys Gly Leu Glu Trp Val
        35                  40                  45

Ser Ala Ile Gly Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Val Leu Ser Pro Lys Ser Tyr Tyr Asp Asn Ser Gly Ile Tyr Phe Asp
            100                 105                 110
```

```
Phe Trp Gly Arg Gly Thr Leu
        115

<210> SEQ ID NO 66
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Thr Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Ile Trp Val Arg Gln Val Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Val Leu Ser Pro Lys Ser Tyr Tyr Asp Asn Ser Gly Ile Tyr Phe Asp
            100                 105                 110

Phe Trp Gly Lys Gly Thr Leu
        115

<210> SEQ ID NO 67
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Val Met Ile Trp Val Arg Gln Val Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Val Leu Ser Pro Lys Ser Tyr Tyr Asp Asn Ser Gly Ile Tyr Phe Asp
            100                 105                 110

Phe Trp Gly Arg Gly Thr Leu
        115

<210> SEQ ID NO 68
<211> LENGTH: 110
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 68

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Phe Gly Gly Ser
            20                  25                  30

Asn His Val Ser Trp Tyr Gln Gln His Pro Gly Lys Ala Pro Lys Leu
        35                  40                  45

Ile Ile Tyr Asp Val Ser Asp Arg Pro Ser Gly Val Ser Asn Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala His Tyr Tyr Cys Ser Ser Tyr Ala Gly Ser
                85                  90                  95

Asn Asn Phe Val Phe Gly Thr Gly Thr Lys Val Thr Val Leu
            100                 105                 110

<210> SEQ ID NO 69
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Ser
            20                  25                  30

Tyr Leu Ala Trp Tyr Arg Gln Lys Pro Gly Gln Ala Pro Arg Leu Leu
        35                  40                  45

Ile Tyr Gly Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Arg
                85                  90                  95

Val Thr Phe Gly Pro Gly Thr Lys Val Asp Ile Lys Arg Thr Val
            100                 105                 110

<210> SEQ ID NO 70
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Gly Ser
            20                  25                  30

Asn Val Ala Trp Tyr Gln Gln Lys Phe Gly Gln Ala Pro Arg Leu Leu
        35                  40                  45

Ile His Gly Ala Ser Lys Arg Ala Ala Gly Ile Pro Asp Arg Phe Ser

-continued

```
                 50                  55                  60
Gly Ser Gly Ser Gly Thr Asp Phe Thr Leu Thr Ile Ser Arg Leu Gln
 65                  70                  75                  80

Pro Asp Asp Tyr Ala Val Tyr Tyr Cys Gln Gln Tyr Gly Thr Lys Pro
                 85                  90                  95

Phe Thr Phe Gly Gln Gly Ser Lys Leu Glu Ile Lys Arg Thr Val
                100                 105                 110

<210> SEQ ID NO 71
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Thr Thr Leu Thr Gln Ser Pro Gly Thr Leu Ser Leu Ser Pro Gly
 1               5                  10                  15

Glu Arg Ala Thr Leu Ser Cys Arg Val Ser Gln Ser Val Ser Ser Asn
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Thr Ser Pro
                 85                  90                  95

Arg Ala Phe Gly His Gly Thr Lys Val Glu Ile Lys Arg Thr Val
                100                 105                 110

<210> SEQ ID NO 72
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Ser Ala Leu Thr Gln Pro Pro Ser Ala Ser Gly Ser Pro Gly Gln
 1               5                  10                  15

Ser Val Thr Ile Ser Cys Thr Gly Ala Ser Ser Asp Ile Gly Gly Tyr
                 20                  25                  30

Lys Ser Val Ser Trp Tyr Gln Gln His Pro Gly Lys Ala Pro Lys Leu
             35                  40                  45

Ile Ile Tyr Asp Val Thr Glu Arg Pro Ser Gly Val Pro Asp Arg Phe
 50                  55                  60

Ser Ala Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Gly Gly Ser
                 85                  90                  95

Asn Asn Leu Val Val Phe Gly Gly Gly Thr Lys Val Thr Val Leu
                100                 105                 110

<210> SEQ ID NO 73
<211> LENGTH: 108
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 73

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Arg Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys Arg
            100                 105

<210> SEQ ID NO 74
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Arg Thr Phe Gly Gln Gly Thr Lys Val Glu Ile Lys Arg Thr
            100                 105                 110

<210> SEQ ID NO 75
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Gly Ala
            20                  25                  30

Asn Leu Gly Trp Tyr Gln Gln Lys Phe Gly Gln Pro Arg Leu Leu
        35                  40                  45

Ile Tyr Gly Ala Ser Ser Arg Ala Thr Gly Val Pro Asp Arg Phe Ser
 50                  55                  60

Gly Ser Gly Ser Gly Thr Asp Phe Ala Leu Thr Ile Ser Arg Leu Glu
 65                  70                  75                  80

Pro Glu Asp Phe Ala Val Tyr Tyr Cys Gln Gln Tyr Gly Ser Lys Pro
                 85                  90                  95

Tyr Thr Phe Gly Gln Gly Thr Lys Leu Glu Ile Lys Arg Thr Val
            100                 105                 110

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Thr Asn
                 20                  25                  30

Leu Ala Trp Tyr Gln Gln Lys Pro Gly Gln Ala Pro Arg Leu Leu Ile
             35                  40                  45

His Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Ser Ala Val Tyr Tyr Cys Gln Gln His Asn Asn Trp Pro Pro
                 85                  90                  95

Val Thr Phe Gly Arg Gly Thr Lys Val Glu Ile Lys Arg Thr Val
            100                 105                 110

<210> SEQ ID NO 77
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Arg Asn
                 20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Ser Ile
                 85                  90                  95

Thr Phe Gly Gln Gly Thr Arg Leu Glu Ile Lys Arg Thr Val Val
            100                 105                 110

<210> SEQ ID NO 78

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Ser Val Leu Thr Gln Pro Pro Ser Ala Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Arg Ala Pro Lys Leu
        35                  40                  45

Leu Ile Tyr Gly Asn Ser Asn Arg Pro Ser Gly Val Pro Ala Arg Phe
    50                  55                  60

Ser Gly Ser Lys Ser Ala Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Val Val Phe Gly Gly Gly Thr Lys Leu Thr Val Leu
            100                 105                 110

<210> SEQ ID NO 79
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Met Thr Gln Ser Pro Ala Thr Leu Ser Val Ser Pro Gly
1               5                   10                  15

Glu Arg Ala Ile Leu Ser Cys Arg Ala Ser Arg Ser Val Ser Thr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Asn
                85                  90                  95

Phe Gly Gly Gly Thr Lys Val Glu Ile Lys Arg
            100                 105

<210> SEQ ID NO 80
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Pro Asn Arg
            20                  25                  30
```

```
Tyr Ile Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                      55                  60

Gly Ser Gly Ser Gly Pro Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Gln Thr Phe Gly Gln Gly Thr Lys Leu Glu Ile Lys Gly Thr Val
                100                 105                 110

<210> SEQ ID NO 81
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ser Val Leu Thr Gln Pro Pro Ser Val Ser Gly Ala Pro Gly Gln
 1               5                  10                  15

Arg Val Thr Ile Ser Cys Gly Gly Ser Arg Ser Asn Ile Gly Ala Gly
             20                  25                  30

Tyr Asp Val His Trp Tyr Gln Gln Phe Pro Gly Thr Ala Pro Lys Val
             35                  40                  45

Val Ile Tyr Gly Asn Asn Arg Pro Ser Gly Val Pro Asp Arg Phe
 50                      55                  60

Ser Gly Ser Lys Ser Gly Thr Ser Ala Ser Leu Ala Ile Thr Gly Leu
 65                  70                  75                  80

Gln Ala Glu Asp Glu Ala Asn Tyr Tyr Cys Gln Ser Tyr Asp Thr Asn
                 85                  90                  95

Leu Gly Gly Ser Ile Phe Gly Gly Gly Thr Gln Val Thr Val Leu
                100                 105                 110

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Ile Val Met Thr Gln Ser Pro Gly Thr Leu Ser Val Ser Pro Gly
 1               5                  10                  15

Asp Ala Thr Leu Ser Cys Arg Ala Ser Arg Asn Ile Asn Asn Asn
             20                  25                  30

Leu Ala Trp Tyr Gln Gln Thr Pro Gly Gln Ala Pro Arg Leu Leu Ile
             35                  40                  45

Tyr Gly Ala Ser Thr Arg Ala Thr Gly Leu Pro Ala Arg Phe Thr Gly
 50                      55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Arg
                 85                  90                  95

Thr Phe Gly Gln Gly Thr Lys Val Glu Ile Lys Arg
                100                 105
```

```
<210> SEQ ID NO 83
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ile Val Asp Ser Ser
            20                  25                  30

Tyr Leu Ala Trp Tyr Gln His Arg Pro Gly Gln Ala Pro Arg Ile Leu
        35                  40                  45

Ile Tyr Gly Ala Ser Ser Arg Ala Pro Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Val Ser Pro
                85                  90                  95

Arg Thr Phe Gly Gln Gly Thr Lys Val Glu Ile Lys Arg Thr Val
            100                 105                 110

<210> SEQ ID NO 84
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Ile Val Leu Thr Gln Ser Pro Gly Thr Leu Ser Leu Ser Pro Gly
1               5                   10                  15

Asp Arg Ala Thr Leu Ser Cys Arg Ala Ser Gln Ser Leu Gly Thr Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Ile Ile Ser Arg Leu Glu
65                  70                  75                  80

Pro Glu Asp Phe Ala Val Tyr Tyr Cys Gln Gln Tyr Gly Arg Ser Pro
                85                  90                  95

Gln Lys Phe Gly Gln Gly Thr Lys Val Glu Ile Lys Arg Thr Val
            100                 105                 110

<210> SEQ ID NO 85
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
```

```
                    20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Thr Ser Gly Leu Arg
 65                  70                  75                  80

Ser Glu Asp Glu Ala Asn Tyr Tyr Cys Ala Ala Trp Asp Asp Ser Leu
                85                  90                  95

Ser Gly Trp Val Phe Gly Gly Gly Thr Lys Leu Thr Val Leu
            100                 105                 110

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Glu Ile Val Met Thr Gln Ser Pro Ala Thr Leu Ser Val Ser Pro Gly
 1               5                  10                  15

Glu Arg Ala Ile Leu Ser Cys Arg Ala Ser Arg Ser Val Ser Thr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Asn
                85                  90                  95

Phe Gly Gly Gly Thr Lys Val Glu Ile Lys Arg
            100                 105

<210> SEQ ID NO 87
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Val Glu Ile Lys Arg
```

<210> SEQ ID NO 88
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ser His Ser Thr Pro Arg
                85                  90                  95

Thr Phe Gly Gln Gly Thr Lys Leu Glu Ile Lys Arg Thr Val
            100                 105                 110

<210> SEQ ID NO 89
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30

Thr Val Asn Trp Tyr Gln Gln Leu Pro Gly Thr Ala Pro Lys Leu Leu
        35                  40                  45

Ile Tyr Arg Asn Ile Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Leu Thr Val Leu
            100                 105                 110

<210> SEQ ID NO 90
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Ile Val Leu Thr Gln Ser Pro Gly Thr Leu Ser Leu Ser Pro Gly
1               5                   10                  15

Glu Lys Ala Thr Leu Ser Cys Arg Ala Ser Gln Ser Val Ser Asn Thr
                20                  25                  30

Tyr Leu Ala Trp Tyr Gln Gln Lys Pro Gly Gln Ala Pro Arg Leu Leu
            35                  40                  45

Leu Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ala Glu Asp Phe Ala Val Tyr Phe Cys Gln Gln Tyr Ala Gly Ser Pro
                85                  90                  95

Arg Thr Phe Gly Gln Gly Thr Lys Val Glu Ile Lys Arg Thr Val
            100                 105                 110

<210> SEQ ID NO 91
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ile Val Leu Thr Gln Ser Pro Gly Ser Leu Ser Leu Ser Pro Gly
1               5                   10                  15

Glu Arg Ala Thr Leu Ser Cys Arg Ala Ser Gln Ser Val Ser His Gly
                20                  25                  30

Tyr Leu Ala Trp Tyr Gln Gln Lys Pro Gly Gln Ala Pro Arg Phe Leu
            35                  40                  45

Ile Tyr Gly Ala Ser Ser Arg Pro Thr Gly Ile Pro Asp Arg Phe Arg
    50                  55                  60

Gly Ser Gly Ser Gly Thr Asp Phe Thr Leu Thr Ile Ser Ser Leu Glu
65                  70                  75                  80

Pro Glu Asp Ser Ala Val Tyr Tyr Cys Gln Gln Tyr Ser Thr Ser Pro
                85                  90                  95

Leu Thr Phe Gly Gly Gly Thr Lys Val Glu Ile Lys Arg Thr Val
            100                 105                 110

<210> SEQ ID NO 92
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Pro Glu Leu Thr Gln Pro Pro Ser Ala Ser Gly Thr Pro Gly Gln Arg
1               5                   10                  15

Val Thr Ile Ser Cys Ser Gly Ser Ser Asn Ile Gly Ser Asn Tyr
                20                  25                  30

Val Tyr Trp Tyr Gln Gln Leu Pro Gly Thr Ala Pro Lys Leu Leu Ile
            35                  40                  45

Tyr Arg Asn Asn Gln Arg Pro Ser Gly Val Pro Asp Arg Phe Ser Gly
    50                  55                  60

Ser Lys Ser Gly Thr Ser Ala Ser Leu Ala Ile Ser Gly Leu Arg Ser
65                  70                  75                  80

Glu Asp Glu Ala Asp Tyr Tyr Cys Ala Ala Trp Asp Asp Ser Leu Ser
                85                  90                  95

```
Gly Trp Val Phe Gly Gly Gly Thr Lys Leu Thr Val Leu
            100                 105

<210> SEQ ID NO 93
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ile Val Asp Ser Ser
            20                  25                  30

Tyr Leu Ala Trp Tyr Gln His Arg Pro Gly Gln Ala Pro Arg Ile Leu
        35                  40                  45

Ile Tyr Gly Ala Ser Ser Arg Ala Pro Gly Val Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Arg Thr Phe Gly Gln Gly Thr Lys Val Glu Ile Lys Arg Thr Val
            100                 105                 110

<210> SEQ ID NO 94
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Ser Val Leu Thr Gln Pro Pro Ser Thr Ser Gly Thr Pro Gly Gln
1               5                   10                  15

Arg Val Thr Ile Ser Cys Ser Gly Ser Ser Asn Ile Gly Arg Lys
            20                  25                  30

Thr Val Asn Trp Tyr Gln Gln Leu Pro Gly Thr Ala Pro Lys Leu Leu
        35                  40                  45

Ile Tyr Asn Asp Asn Gln Arg Pro Ser Gly Val Pro Asp Arg Phe Ser
    50                  55                  60

Gly Ser Lys Ala Gly Thr Ser Ala Ser Leu Ala Ile Ser Gly Leu Gln
65                  70                  75                  80

Ser Glu Asp Glu Ala Asp Tyr Tyr Cys Ala Val Trp Asp Asp Ser Leu
                85                  90                  95

Asn Ala Trp Val Phe Gly Gly Gly Thr Lys Leu Thr Val Leu
            100                 105                 110

<210> SEQ ID NO 95
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95
```

Asp Val Val Met Thr Gln Ser Pro Leu Ser Leu Pro Val Thr Pro Gly
1               5                   10                  15

Glu Pro Ala Ala Ile Ser Cys Arg Ser Ser Gln Ser Leu Leu His Ser
            20                  25                  30

Asp Gly Asn Asn Tyr Leu Asp Trp Tyr Leu Gln Lys Pro Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Glu Leu Lys Ile
65                  70                  75                  80

Ser Arg Val Glu Ala Glu Asp Ala Gly Val Tyr Tyr Cys Met Gln Ala
                85                  90                  95

Ser Gln Thr Pro Arg Thr Phe Gly Gln Gly Thr Lys Leu Glu Leu Lys
            100                 105                 110

Arg Thr Val
    115

<210> SEQ ID NO 96
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

His Val Ile Leu Thr Gln Pro Pro Ser Val Ser Val Ala Pro Gly Met
1               5                   10                  15

Thr Ala Arg Met Thr Cys Gly Gly Asp Asn Val Gly Arg Arg Asn Val
            20                  25                  30

His Trp Tyr Gln Gln Lys Pro Gly Gln Ala Pro Val Leu Val Val Tyr
        35                  40                  45

Asp Asp Gly Gly Arg Pro Ser Ala Ile Pro Ala Arg Phe Ser Gly Ser
    50                  55                  60

Lys Ser Gly Asn Thr Ala Thr Leu Ile Ile Ser Arg Val Glu Ala Gly
65                  70                  75                  80

Asp Glu Ala Asp Tyr Tyr Cys Gln Met Trp His Ser Ser Gly Asp Gln
                85                  90                  95

Trp Val Phe Gly Gly Gly Thr Lys Leu Thr Val Leu
            100                 105

<210> SEQ ID NO 97
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Pro Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Lys Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80

Pro Glu Asp Ser Ala Val Tyr Tyr Cys Gln His Gln Gly Phe Gly Gln
                85                  90                  95

Gly Thr Lys Val Glu Ile Lys Arg Thr Val
            100                 105

<210> SEQ ID NO 98
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Gln Ser Val Leu Thr Gln Pro Pro Ser Ala Ser Gly Thr Pro Asp Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Ala Ala Pro Lys Leu Leu
        35                  40                  45

Met Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Thr Gly Tyr Val Phe Gly Thr Gly Thr Lys Leu Thr Val Leu
            100                 105                 110

<210> SEQ ID NO 99
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ser Tyr Val Leu Thr Gln Pro Pro Ser Val Ser Val Ala Pro Gly Lys
1               5                   10                  15

Thr Ala Arg Ile Thr Cys Gly Gly Lys Asn Ile Gly Ser Lys Ser Val
            20                  25                  30

His Trp Tyr Gln Gln Lys Ser Gly Gln Ala Pro Val Leu Val Ile Tyr
        35                  40                  45

Gly Asp Ser Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Glu
65                  70                  75                  80

Asp Glu Ala Asp Tyr Tyr Cys Gln Val Trp Asp Asn Thr Ser Asp His
                85                  90                  95

Ala Gly Val Phe Gly Gly Gly Thr Lys Val Thr Val Leu
            100                 105

<210> SEQ ID NO 100
<211> LENGTH: 110
<212> TYPE: PRT
<213> ORGANISM: Artificial Sequence
<220> FEATURE:

-continued

<223> OTHER INFORMATION: Description of Artificial Sequence: Synthetic
     polypeptide

<400> SEQUENCE: 100

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Ser Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Leu Val Phe Gly Gly Gly Thr Lys Leu Thr Val Leu
            100                 105                 110

<210> SEQ ID NO 101
<211> LENGTH: 110
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 101

Gln Ser Val Leu Thr Gln Pro Pro Ser Val Ser Ala Ala Pro Arg Gln
1               5                   10                  15

Ser Val Thr Ile Ser Cys Ser Gly Thr Thr Ser Asn Ile Gly Asn Asn
            20                  25                  30

Pro Val Ser Trp Tyr Gln Gln Phe Pro Gly Arg Ala Pro Asn Leu Leu
        35                  40                  45

Ile Tyr Tyr Asn Asp Val Val Pro Ser Gly Val Ser Asp Arg Phe Ser
    50                  55                  60

Ala Ser Lys Ala Gly Thr Ser Ala Ser Leu Ala Ile Ser Arg Leu Gln
65                  70                  75                  80

Ser Glu Asp Glu Ala Asp Tyr Tyr Cys Ala Thr Trp Asp Asp Ser Leu
                85                  90                  95

Ser Ala Trp Val Phe Gly Gly Gly Thr Gln Leu Thr Val Leu
            100                 105                 110

<210> SEQ ID NO 102
<211> LENGTH: 110
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 102

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser

```
                 50                  55                  60
Gly Ser Lys Ser Gly Thr Ser Ala Ser Leu Val Ile Ser Gly Leu Gln
 65                  70                  75                  80

Ser Glu Asp Glu Thr Asp Tyr Tyr Cys Ala Ala Trp Asp Asp Ser Leu
                 85                  90                  95

Asn Gly Trp Val Phe Gly Gly Gly Thr Lys Leu Thr Val Leu
                100                 105                 110

<210> SEQ ID NO 103
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Ser Ala Leu Thr Gln Pro Pro Ser Ala Ser Gly Ser Pro Gly Gln
 1               5                  10                  15

Ser Val Thr Ile Thr Cys Ala Gly Ala Ser Ser Asp Leu Gly Asp Tyr
                 20                  25                  30

Lys Ser Val Ser Trp Tyr Gln Gln His Pro Gly Lys Ala Pro Lys Leu
             35                  40                  45

Ile Ile Tyr Asp Val Ile Lys Arg Pro Ala Gly Val Pro Asp Arg Phe
         50                  55                  60

Ser Ala Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Tyr Ala Gly Ser
                 85                  90                  95

Asn Asn Ile Val Ile Phe Gly Gly Gly Thr Lys Leu Thr Val Leu
                100                 105                 110

<210> SEQ ID NO 104
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Thr Thr Leu Thr Gln Ser Pro Gly Thr Leu Ser Leu Ser Pro Gly
 1               5                  10                  15

Glu Arg Ala Thr Leu Ser Cys Arg Ala Ser Gln Gly Ile Asp Arg Lys
                 20                  25                  30

Tyr Leu Ala Trp Tyr Gln Arg Lys His Gly Gln Ala Pro Arg Leu Leu
             35                  40                  45

Ile Tyr Gly Ala Ser Asn Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Asp Ser Phe
                 85                  90                  95

Val Ser Phe Gly Gln Gly Thr Lys Leu Glu Ile Lys Arg Thr Val
                100                 105                 110

<210> SEQ ID NO 105
<211> LENGTH: 111
<212> TYPE: PRT
```

<213> ORGANISM: Artificial Sequence
<220> FEATURE:
<223> OTHER INFORMATION: Description of Artificial Sequence: Synthetic
       polypeptide

<400> SEQUENCE: 105

Asp Ile Gln Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ile Pro Lys Leu Leu Ile
        35                  40                  45

Tyr Glu Ala Ser Asn Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Asp Phe Leu
                85                  90                  95

Val Thr Phe Gly Pro Gly Thr Lys Val Asp Ile Lys Arg Thr Val
            100                 105                 110

<210> SEQ ID NO 106
<211> LENGTH: 111
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 106

Gln Ser Val Leu Thr Gln Pro Pro Ser Val Ser Gly Ala Pro Gly Gln
1               5                   10                  15

Lys Ile Thr Ile Ser Cys Thr Gly Ser Ser Asn Ile Gly Thr Gly
            20                  25                  30

Tyr Asp Val His Trp Tyr Gln Gln Leu Pro Gly Arg Ala Pro Arg Leu
        35                  40                  45

Leu Ile Ser Ala Asp Ala Asn Arg Pro Ser Gly Val Pro Asp Arg Phe
50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Arg
                85                  90                  95

Leu Gly Gly Ser Ile Phe Gly Gly Thr Gln Leu Thr Val Leu
            100                 105                 110

<210> SEQ ID NO 107
<211> LENGTH: 108
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 107

Glu Ile Val Met Thr Gln Ser Pro Gly Thr Leu Ser Val Ser Pro Gly
1               5                   10                  15

Asp Ala Ala Thr Leu Ser Cys Arg Ala Ser Arg Asn Ile Asn Asn Asn
            20                  25                  30

Leu Ala Trp Tyr Gln Gln Thr Pro Gly Gln Ala Pro Arg Leu Leu Ile
        35                  40                  45

```
Tyr Gly Ala Ser Thr Arg Ala Thr Gly Leu Pro Ala Arg Phe Thr Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Arg
                85                  90                  95

Thr Phe Gly Gln Gly Thr Lys Val Glu Ile Lys Arg
                100                 105

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Ser Val Leu Thr Gln Pro Pro Ser Val Ser Ala Ala Pro Gly Gln
1               5                   10                  15

Glu Val Thr Ile Thr Cys Ser Gly Ser Gly Ala Asn Ile Gly Asn Asn
            20                  25                  30

Tyr Val Ser Trp Tyr Gln Gln Val Pro Gly Thr Ala Pro Lys Leu Val
        35                  40                  45

Ile Tyr Asp Asn Asn Arg Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Val Phe Gly Gly Gly Thr Lys Val Thr Val Leu
                100                 105                 110

<210> SEQ ID NO 109
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Ala Val Leu Thr Gln Pro Pro Ser Ala Ser Gly Thr Pro Gly Gln
1               5                   10                  15

Thr Val Thr Ile Ser Cys Ser Gly Val Thr Ser Asn Ile Gly Asn Asn
            20                  25                  30

Tyr Val Tyr Trp Tyr Gln Gln Leu Pro Gly Thr Ala Pro Arg Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ala Trp Asp Asp Ser Leu
                85                  90                  95

Arg Glu Asn Leu Phe Gly Thr Gly Thr Gln Leu Thr Val Leu
                100                 105                 110

<210> SEQ ID NO 110
```

```
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Phe Gly Met Asn
            20                  25                  30

Ala Val Asn Trp Tyr Gln Gln Leu Pro Gly Thr Ala Pro Lys Leu Leu
        35                  40                  45

Met Tyr Ser Asn Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ser Ala Trp Asp Asp Asn Leu
                85                  90                  95

Asn Gly Trp Val Phe Gly Gly Gly Thr Lys Val Thr Val Leu
            100                 105                 110

<210> SEQ ID NO 111
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Thr Trp Asp Asp Ser Leu
                85                  90                  95

Thr Ser Val Val Phe Gly Gly Gly Thr Lys Val Thr Val Leu
            100                 105                 110

<210> SEQ ID NO 112
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Thr Thr Leu Thr Gln Ser Pro Ser Ser Leu Ser Ala Ser Ile Gly
1               5                   10                  15

Asp Arg Ile Thr Ile Ala Cys Gln Ala Ser Gln Asp Ile Arg Asn Arg
            20                  25                  30
```

```
Leu Asn Trp Tyr Leu Gln Arg Pro Gly Lys Ala Pro Gln Leu Leu Ile
             35                  40                  45

Tyr Asp Ala Ser Asn Leu Glu Thr Gly Val Pro Ser Lys Phe Ala Gly
 50                  55                  60

Arg Gly Ser Gly Thr Asp Phe Thr Leu Thr Ile Ser Ser Leu Gln Pro
 65                  70                  75                  80

Glu Asp Ile Gly Thr Tyr Phe Cys Gln Gln Tyr Gly Asp Leu Ser Pro
                 85                  90                  95

Leu Thr Phe Gly Gly Gly Thr Lys Val Asp Ile Arg Arg Thr Val
                100                 105                 110
```

<210> SEQ ID NO 113
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Glu Thr Thr Leu Thr Gln Ser Pro Ser Ser Leu Ser Ala Ser Ile Gly
 1               5                  10                  15

Asp Arg Ile Thr Ile Ala Cys Gln Ala Ser Gln Asp Ile Arg Asn Arg
             20                  25                  30

Leu Asn Trp Tyr Leu Gln Arg Pro Gly Lys Ala Pro Gln Leu Leu Ile
             35                  40                  45

Tyr Asp Ala Ser Asn Leu Glu Thr Gly Val Pro Ser Lys Phe Ala Gly
 50                  55                  60

Arg Gly Ser Gly Thr Asp Phe Thr Leu Thr Ile Ser Ser Leu Gln Pro
 65                  70                  75                  80

Glu Asp Ile Gly Thr Tyr Phe Cys Gln Gln Tyr Gly Asp Leu Ser Pro
                 85                  90                  95

Leu Thr Phe Gly Gly Gly Thr Lys Val Asp Ile Arg Arg Thr Val
                100                 105                 110
```

<210> SEQ ID NO 114
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
             20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ser Ala Thr Tyr Tyr Cys Gln Gln Ser His Ser Thr Pro Arg
                 85                  90                  95

Thr Phe Gly Gln Gly Thr Lys Leu Glu Ile Lys Arg Thr Val
                100                 105                 110
```

<210> SEQ ID NO 115
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Ser Val Leu Thr Gln Pro Pro Ser Val Ser Gly Ala Pro Gly Gln
1               5                   10                  15

Arg Val Thr Ile Ser Cys Thr Gly Thr Ser Ser Asn Ile Gly Ala Gly
            20                  25                  30

Phe Asp Val His Trp Tyr Gln Gln Phe Pro Gly Thr Ala Pro Lys Leu
        35                  40                  45

Leu Ile Tyr Asp Asn Val Lys Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Arg Ala Glu Asp Glu Ala Asp Tyr Tyr Cys Gln Ser Tyr Asp Thr Ser
                85                  90                  95

Leu Ser Arg Tyr Val Phe Gly Thr Gly Thr Lys Val Thr Val Leu
            100                 105                 110

<210> SEQ ID NO 116
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ile
            20                  25                  30

Tyr Leu Ala Trp Tyr Gln Gln Lys Pro Gly Gln Ala Pro Arg Leu Val
        35                  40                  45

Ile His Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys Arg Thr Val
            100                 105                 110

<210> SEQ ID NO 117
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Thr Thr Leu Thr Gln Ser Pro Gly Ile Leu Ser Leu Ser Pro Gly
1               5                   10                  15

Glu Ser Ala Thr Leu Ser Cys Gly Ala Ser Gln Thr Ile Ser Ser Arg

```
                20                  25                  30

Tyr Leu Ala Trp Tyr Gln Gln Arg Pro Gly Gln Ala Pro Arg Leu Leu
            35                  40                  45

Ile Phe Asp Ala Ser Arg Arg Ala Thr Gly Val Pro Asp Arg Phe Ser
 50                  55                  60

Gly Gly Gly Ser Gly Thr Asp Phe Thr Leu Thr Ile Ser Arg Leu Glu
 65                  70                  75                  80

Pro Glu Asp Phe Gly Val Phe Tyr Cys Gln Gln Tyr Gly Ile Ser Pro
                 85                  90                  95

Tyr Thr Phe Gly Gln Gly Thr Lys Leu Glu Ile Lys Arg Thr Val
                100                 105                 110

<210> SEQ ID NO 118
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Gly Asn
                20                  25                  30

Asn Leu Ala Trp Tyr Gln Gln Lys Phe Gly Gln Ala Pro Arg Leu Leu
            35                  40                  45

Ile Tyr Ala Ala Ser Ser Arg Ala Thr Asp Ile Pro Ala Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Val Asp Ser Pro
                 85                  90                  95

Arg Thr Phe Gly Gln Gly Thr Lys Val Glu Ile Lys Arg Thr Val
                100                 105                 110

<210> SEQ ID NO 119
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Leu Thr Phe Gly Gly Gly Thr Lys Val Glu Ile Lys Arg Thr Val
```

<210> SEQ ID NO 120
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Lys Thr Phe Gly Gln Gly Thr Lys Val Glu Ile Lys Arg Thr Val
            100                 105                 110

<210> SEQ ID NO 121
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ser Val Leu Thr Gln Pro Pro Ser Val Ser Gly Ala Pro Gly Gln
1               5                   10                  15

Gly Val Thr Ile Ser Cys Ser Gly Ser Ser Ser Asn Ile Gly Ala Asn
            20                  25                  30

Tyr Val Val His Trp Tyr Arg Gln Leu Pro Gly Ala Ala Pro Lys Leu
        35                  40                  45

Leu Ile Tyr Asp Asp Ile His Arg Pro Ser Gly Val Pro Asp Arg Phe
    50                  55                  60

Ser Gly Ser Arg Ser Gly Thr Ser Ala Ser Leu Ala Ile Thr Gly Leu
65                  70                  75                  80

Gln Pro Glu Asp Glu Ala Asp Tyr Tyr Cys Gln Thr Tyr Asp Thr Ser
                85                  90                  95

Leu Arg Gly Ser Val Phe Gly Gly Gly Thr Lys Leu Thr Val Leu
            100                 105                 110

<210> SEQ ID NO 122
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                85                  90                  95

Ser Gly Trp Val Phe Gly Gly Gly Thr Lys Val Thr Val Leu
            100                 105                 110

<210> SEQ ID NO 123
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ala Val Leu Thr Gln Pro Pro Ser Val Ser Val Ala Pro Gly Lys
 1               5                  10                  15

Thr Ala Thr Ile Thr Cys Gly Val Asn Asn Leu Gly Arg Lys Ser Val
            20                  25                  30

His Trp Tyr Gln Gln Lys Pro Gly Gln Ala Pro Val Leu Val Val Tyr
        35                  40                  45

Asp Ser Asn Asp Arg Pro Ser Gly Ile Pro Glu Arg Phe Ser Gly Ser
 50                  55                  60

Asn Ser Gly Asn Thr Ala Thr Leu Ile Ile Ser Arg Val Glu Ala Gly
 65                  70                  75                  80

Asp Glu Ala Asp Tyr Ser Cys Gln Val Trp Asn Asn Val Asp His
                85                  90                  95

Pro Val Phe Gly Gly Gly Thr Lys Leu Thr Val Leu
            100                 105

<210> SEQ ID NO 124
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                85                  90                  95

Trp Val Phe Gly Gly Gly Thr Lys Val Thr Val Leu
            100                 105

<210> SEQ ID NO 125
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Asn Arg Ala Thr Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Pro Arg
                85                  90                  95

Thr Phe Gly Gln Gly Thr Lys Leu Glu Ile Lys Arg
            100                 105

<210> SEQ ID NO 126
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Asn Phe Gly Gly Gly Thr Lys Val Asp Ile Lys Arg
            100                 105

<210> SEQ ID NO 127
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

```
Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Ser Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Val Val Phe Gly Gly Gly Thr Lys Leu Thr Val Leu
            100                 105                 110
```

<210> SEQ ID NO 128
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

```
Gln Ser Val Val Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asp Thr Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Gly Ser
                85                  90                  95

Arg Ser Gly Leu Val Phe Gly Gly Gly Thr Lys Leu Thr Val Leu
            100                 105                 110
```

<210> SEQ ID NO 129
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Asn Ala
            20                  25                  30

Tyr Leu Ala Trp Tyr Gln Gln Lys Pro Gly Gln Ala Pro Arg Leu Leu
        35                  40                  45

Leu Tyr Gly Gly Ser Thr Arg Ala Thr Gly Ile Pro Asp Arg Phe Ser
    50                  55                  60

Gly Ser Gly Ser Gly Thr Asp Phe Thr Leu Thr Ile Ser Ser Leu Glu
65                  70                  75                  80
```

Ala Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg Thr Val
            100                 105                 110

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Thr Ser Ser Arg Ala Thr Asp Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Phe Thr Phe Gly Gly Gly Thr Lys Val Glu Ile Lys Arg Thr Val
            100                 105                 110

<210> SEQ ID NO 131
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Val Glu Ile Lys Arg Thr Val
            100                 105                 110

<210> SEQ ID NO 132
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 132

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Leu
                85                  90                  95

Thr Phe Gly Gly Gly Thr Lys Val Glu Ile Lys Arg Thr Val
            100                 105                 110

<210> SEQ ID NO 133
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Val Glu Ile Lys
            100                 105

<210> SEQ ID NO 134
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Phe Val Tyr Trp Tyr Gln Gln Leu Pro Gly Thr Ala Pro Lys Leu Leu
        35                  40                  45

Ile Tyr Lys Ser Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
```

```
                65                  70                  75                  80
Ser Glu Asp Glu Ala Asp Tyr Tyr Cys Ala Ala Trp Asp Asp Ser Leu
                    85                  90                  95

Ser Gly Tyr Val Phe Gly Thr Gly Thr Gln Leu Thr Val Leu
                100                 105                 110
```

<210> SEQ ID NO 135
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Glu Thr Thr Leu Thr Gln Ser Pro Asp Thr Leu Ser Leu Ser Pro Gly
1               5                   10                  15

Glu Arg Ala Thr Leu Ser Cys Arg Ala Ser Gln Ser Val Ser Ser Gly
                20                  25                  30

Ser Leu Ala Trp Tyr Gln Gln Lys Pro Gly Gln Ala Pro Arg Leu Leu
            35                  40                  45

Ile Tyr Ala Ala Ser Ser Arg Ala Ala Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Gly Leu Thr Phe Gly Gly Gly Thr Gln Val Glu Ile Lys Arg Thr Val
                100                 105                 110
```

<210> SEQ ID NO 136
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Tyr Thr Phe Gly Gln Gly Thr Lys Leu Glu Ile Lys Arg Thr Val
                100                 105                 110
```

<210> SEQ ID NO 137
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asn Ile Gly Trp Tyr
            20                  25                  30

Leu Ala Trp Tyr Gln His Lys Pro Gly Gln Ala Pro Arg Leu Ile Met
        35                  40                  45

Tyr Asp Ala Ser Thr Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Val Pro Ser
                85                  90                  95

Thr Phe Gly Gln Gly Thr Asn Leu Glu Ile Lys Arg Thr Val
            100                 105                 110

<210> SEQ ID NO 138
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Thr Pro Lys Leu
        35                  40                  45

Leu Ile Tyr Asp Asn Thr Asn Arg Pro Ser Gly Val Pro Asp Arg Phe
    50                  55                  60

Ser Ala Ser Lys Ser Gly Ala Ser Ala Ser Leu Ala Ile Thr Gly Leu
65                  70                  75                  80

Arg Asp Glu Asp Glu Ala Asp Tyr Tyr Cys Gln Ser Tyr Asp Ser Ser
                85                  90                  95

Leu Ser Ala Ser Val Phe Gly Gly Gly Thr Lys Leu Thr Val Leu
            100                 105                 110

<210> SEQ ID NO 139
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Ser Ala Leu Thr Gln Pro Arg Ser Val Ser Gly Ser Pro Gly Gln
1               5                   10                  15

Ser Val Thr Ile Ser Cys Thr Gly Thr Thr Ser Asp Val Gly Gly Tyr
            20                  25                  30

Asn Tyr Val Ser Trp Tyr Gln Gln His Pro Gly Glu Ala Pro Lys Leu
        35                  40                  45

Ile Ile Tyr Asp Val Ser Asn Arg Pro Ser Gly Val Ser Asn Arg Phe
    50                  55                  60

```
Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Ser Ser Phe Ala Gly Ser
                 85                  90                  95

Ser Asn Leu Ile Phe Gly Gly Gly Thr Lys Leu Thr Val Leu
            100                 105                 110

<210> SEQ ID NO 140
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Ser Val Ser Arg Asn
                 20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Ser Ile
                 85                  90                  95

Thr Phe Gly Gln Gly Thr Arg Leu Glu Ile Lys Arg Thr Val
            100                 105                 110

<210> SEQ ID NO 141
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ser Tyr Glu Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
            35                  40                  45

Ile Tyr Ser Asn Asn His Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Thr Trp Asp Asp Ser Leu
                 85                  90                  95

Asn Gly Trp Val Phe Gly Gly Gly Thr Lys Val Thr Val Leu
            100                 105                 110

<210> SEQ ID NO 142
<211> LENGTH: 110
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 142

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val Asn Trp Tyr Gln Gln Val Pro Gly Thr Ala Pro Lys Leu Leu
        35                  40                  45

Ile His Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Leu
65                  70                  75                  80

Ser Glu Asp Glu Ala Asp Tyr Tyr Cys Glu Val Trp Asp Ser Leu
                85                  90                  95

Asn Gly Arg Val Phe Gly Gly Gly Thr Lys Leu Thr Val Leu
            100                 105                 110

<210> SEQ ID NO 143
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Leu Glu Ile Lys Arg
            100                 105

<210> SEQ ID NO 144
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

His Pro Glu Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Gly Pro Lys Leu Leu
        35                  40                  45
```

```
Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Lys Val Thr Val Leu
            100                 105                 110

<210> SEQ ID NO 145
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Gln
                 85                  90                  95

Val Thr Phe Gly Gly Gly Thr Lys Val Glu Ile Lys Arg
            100                 105

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

His Val Ile Leu Thr Gln Pro Pro Ser Val Ser Val Ala Pro Gly Met
 1               5                  10                  15

Thr Ala Arg Met Thr Cys Gly Gly Asp Asn Val Gly Arg Arg Asn His
                20                  25                  30

Trp Tyr Gln Gln Lys Pro Gly Gln Ala Pro Val Leu Val Val Tyr Asp
            35                  40                  45

Asp Gly Gly Arg Pro Ser Ala Ile Pro Ala Arg Phe Ser Gly Ser Lys
        50                  55                  60

Ser Gly Asn Thr Ala Thr Leu Ile Ile Ser Arg Val Glu Ala Gly Asp
 65                  70                  75                  80

Glu Ala Asp Tyr Tyr Cys Gln Met Trp His Ser Ser Gly Asp Gln Trp
                 85                  90                  95

Val Phe Gly Gly Gly Thr Lys Leu Thr Val Leu
            100                 105

<210> SEQ ID NO 147
<211> LENGTH: 110
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Tyr Trp Tyr Gln His Leu Pro Gly Thr Ala Pro Lys Leu Leu
            35                  40                  45

Ile Asp Arg Asn Asp Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Asn Leu
                85                  90                  95

Ser Gly Val Val Phe Gly Gly Gly Thr Lys Val Thr Val Leu
            100                 105                 110

<210> SEQ ID NO 148
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gln Ser Val Val Thr Gln Pro Pro Ser Val Ser Gly Ala Pro Gly Gln
1               5                   10                  15

Arg Val Thr Ile Ser Cys Thr Gly Ser Ser Ile Gly Ala Gly Tyr Asp
            20                  25                  30

Val His Trp Tyr Gln Gln Leu Pro Arg Thr Ala Pro Lys Leu Leu Ile
            35                  40                  45

Phe Gly Asn Thr Asn Arg Pro Ser Gly Val Pro Asp Arg Phe Ser Gly
        50                  55                  60

Ser Lys Ser Gly Thr Ser Ala Ser Leu Thr Ile Thr Gly Leu Gln Ala
65                  70                  75                  80

Glu Asp Glu Ala Asn Tyr Tyr Cys Gln Thr Tyr Asp Ser Ser Leu Ser
                85                  90                  95

Gly Trp Val Phe Gly Gly Gly Thr Lys Leu Thr Val Leu
            100                 105

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Pro Glu Leu Thr Gln Pro Pro Ser Ala Ser Gly Thr Pro Gly Gln Arg
1               5                   10                  15

Val Thr Ile Ser Cys Ser Gly Ser Ser Asn Ile Gly Ser Asn His
            20                  25                  30

Val Tyr Trp Tyr Gln Gln Leu Pro Gly Thr Ala Pro Lys Leu Leu Ile
```

```
                35                  40                  45

Tyr Arg Asn Asn Gln Arg Pro Ser Gly Val Pro Asp Arg Phe Ser Gly
 50                  55                  60

Ser Lys Ser Gly Thr Ser Ala Ser Leu Ala Ile Ser Gly Leu Arg Ser
 65                  70                  75                  80

Glu Asp Glu Ala Asp Tyr Tyr Cys Ala Thr Trp Asp Asn Leu Ser
                 85                  90                  95

Gly Arg Leu Val Phe Gly Gly Gly Thr Lys Leu Thr Val Leu
                100                 105                 110

<210> SEQ ID NO 150
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Gln Ser Val Leu Thr Gln Pro Pro Ser Val Ser Gly Ala Pro Gly Gln
 1               5                  10                  15

Arg Val Thr Ile Ser Cys Ile Gly Ser Asn Ser Asn Ile Gly Ala Asn
                20                  25                  30

Phe Ala Val His Trp Tyr Gln Gln Leu Pro Gly Ala Ala Pro Lys Leu
                35                  40                  45

Leu Ile Tyr Asp Asn Thr Asn Arg Pro Ser Gly Val Pro Asp Arg Phe
 50                  55                  60

Ser Gly Ser Lys Ser Gly Thr Ser Ala Ser Leu Asp Ile Thr Gly Leu
 65                  70                  75                  80

Gln Ala Asp Asp Glu Ala Asp Tyr Tyr Cys Gln Ser Tyr Asp Ala Arg
                 85                  90                  95

Leu Asn Gly Trp Val Phe Gly Gly Gly Thr Lys Leu Thr Val Leu
                100                 105                 110

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Gln Ser Ala Leu Thr Gln Pro Pro Ser Ala Ser Gly Ser Pro Gly Gln
 1               5                  10                  15

Ser Val Thr Ile Ser Cys Ala Gly Ala Ser Ser Asp Ile Gly Thr Tyr
                20                  25                  30

Asn Ser Val Ser Trp Tyr Gln Gln His Pro Gly Lys Ala Pro Lys Leu
                35                  40                  45

Ile Ile Tyr Glu Val Thr Lys Arg Pro Ser Gly Val Pro Asp Arg Phe
 50                  55                  60

Ser Gly Ser Lys Ser Gly Asn Thr Ala Ser Leu Thr Val Ser Gly Leu
 65                  70                  75                  80

Gln Ala Glu Asp Glu Ala Asp Tyr Tyr Cys Asn Ser Tyr Ala Gly Thr
                 85                  90                  95

Lys Gly Tyr Val Phe Gly Ser Gly Thr Lys Val Thr Val Leu
                100                 105                 110
```

```
<210> SEQ ID NO 152
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Glu Tyr Ala
            20                  25                  30

Ser Trp Tyr Gln Gln Lys Pro Gly Gln Ala Pro Val Leu Val Met Lys
        35                  40                  45

Gly Asn Asn Asn Arg Pro Ser Val Ile Pro Asp Arg Phe Ser Gly Ser
    50                  55                  60

Arg Ser Gly Asn Thr Ala Ser Leu Thr Ile Thr Gly Ala Gln Ala Glu
65                  70                  75                  80

Asp Glu Ala Asp Tyr Tyr Cys Ser Ser Arg Asp Ser Ser Gly Asn Arg
                85                  90                  95

Phe Phe Gly Ser Gly Thr Lys Val Thr Val Leu
            100                 105

<210> SEQ ID NO 153
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

His Pro Glu Leu Thr Gln Pro Pro Ser Leu Ser Val Ser Pro Gly Gln
1               5                   10                  15

Thr Ala Thr Ile Ser Cys Ser Gly Glu Arg Leu Thr Asn Lys Tyr Thr
            20                  25                  30

Ser Trp Tyr Gln Gln Arg Pro Gly Gln Ser Pro Ala Leu Val Ile Tyr
        35                  40                  45

Gln Asp Asp Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Pro Met
65                  70                  75                  80

Asp Glu Ala Val Tyr Tyr Cys Gln Ala Trp Asp Thr Asn Thr Gln Met
                85                  90                  95

Thr Phe Gly Gly Gly Thr Lys Leu Thr Val Leu
            100                 105

<210> SEQ ID NO 154
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gln Ala Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Thr Asn
            20                  25                  30
```

Thr Val Asn Trp Tyr Gln Gln Leu Pro Gly Thr Ala Pro Lys Leu Leu
            35                  40                  45

Ile Tyr Arg Asn Ile Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Tyr Val Phe Gly Thr Gly Thr Lys Leu Thr Val Leu
                100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Thr Thr Leu Thr Gln Ser Pro Gly Thr Val Ser Leu Ser Pro Gly
 1               5                  10                  15

Glu Arg Ala Thr Leu Ser Cys Arg Ala Ser Gln Ser Val Gly Gly Ser
             20                  25                  30

Asn Leu Ala Trp Tyr Gln Lys Pro Gly Gln Ala Pro Arg Leu Val
            35                  40                  45

Ile Tyr Ala Thr Ser Arg Lys Ala Asn Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Phe Cys Gln Gln Tyr Gly Thr Ser Pro
                 85                  90                  95

Pro Ser Val Thr Phe Gly Gly Gly Thr Lys Val Glu Ile Arg Arg
                100                 105                 110

<210> SEQ ID NO 156
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Gln Ala Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
             20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Thr Gly Tyr Val Phe Gly Thr Gly Thr Gln Leu Thr Val Leu
                100                 105                 110

<210> SEQ ID NO 157
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Ser Tyr Val Leu Thr Gln Pro Pro Ser Ala Ser Gly Thr Pro Asp Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Phe Pro Gly Ala Ala Pro Lys Leu Leu
        35                  40                  45

Met Ser Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Tyr Tyr Ser Cys Ala Ala Trp Asp Asp Ser Leu
                85                  90                  95

Asn Gly Leu Val Phe Gly Gly Gly Thr Lys Val Thr Val Leu
            100                 105                 110

<210> SEQ ID NO 158
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Asn Phe Met Leu Thr Gln Pro His Ser Val Ser Glu Ser Pro Gly Lys
1               5                   10                  15

Thr Val Thr Ile Ser Cys Thr Gly Ser Gly Gly Asn Ile Ala Arg Asn
            20                  25                  30

Tyr Val Gln Trp Tyr Gln Gln Arg Pro Gly Ser Ala Pro Val Thr Val
        35                  40                  45

Ile Leu Glu Asp Asp Lys Arg Pro Ser Gly Ile Pro Asp Arg Phe Ser
    50                  55                  60

Gly Ser Ile Asp Arg Ser Ser Asn Ser Ala Ser Leu Thr Ile Ser Gly
65                  70                  75                  80

Leu Arg Thr Glu Asp Glu Ala Leu Tyr Tyr Cys Gln Ser Tyr Asp Asp
                85                  90                  95

Ser Asp Leu Val Val Phe Gly Gly Gly Thr Lys Leu Thr
            100                 105

<210> SEQ ID NO 159
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

Asn Phe Met Leu Thr Gln Pro His Ser Val Ser Glu Ser Pro Gly Lys
1               5                   10                  15

Thr Val Thr Ile Ser Cys Thr Gly Ser Ser Gly Ser Ile Ala Ser Asn
            20                  25                  30

Tyr Val Gln Trp Tyr Gln Gln Arg Pro Gly Ser Ala Pro Thr Thr Val
                35                  40                  45

Ile Tyr Glu Asp Tyr Gln Arg Pro Ser Gly Val Pro Asp Arg Phe Ser
 50                  55                  60

Gly Ser Ile Asp Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Asp
                85                  90                  95

Ser Asp His Leu Ile Phe Gly Gly Gly Thr Lys Leu Thr Val Leu
                100                 105                 110

<210> SEQ ID NO 160
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
                20                  25                  30

Thr Val Asn Trp Tyr Lys Gln Leu Pro Gly Thr Ala Pro Arg Leu Leu
                35                  40                  45

Ile Tyr Ser Asn Asp Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asn Tyr Tyr Cys Ala Ala Trp Asp Asp Ser Leu
                85                  90                  95

Ser Gly Trp Val Phe Gly Gly Gly Thr Lys Leu Thr Val Leu
                100                 105                 110

<210> SEQ ID NO 161
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Gln or Glu
<220> FEATURE:
<221> NAME/KEY: MOD_RES
<222> LOCATION: (2)..(2)
<223> OTHER INFORMATION: Val or Met
<220> FEATURE:
<221> NAME/KEY: MOD_RES
<222> LOCATION: (9)..(9)
<223> OTHER INFORMATION: Ala or Thr
<220> FEATURE:
<221> NAME/KEY: MOD_RES
<222> LOCATION: (12)..(12)
<223> OTHER INFORMATION: Lys or Gln
<220> FEATURE:
<221> NAME/KEY: MOD_RES
<222> LOCATION: (16)..(16)
<223> OTHER INFORMATION: Ser or Ala
<220> FEATURE:

```
<221> NAME/KEY: MOD_RES
<222> LOCATION: (19)..(19)
<223> OTHER INFORMATION: Lys or Arg
<220> FEATURE:
<221> NAME/KEY: MOD_RES
<222> LOCATION: (20)..(20)
<223> OTHER INFORMATION: Val or Leu
<220> FEATURE:
<221> NAME/KEY: MOD_RES
<222> LOCATION: (24)..(24)
<223> OTHER INFORMATION: Ala, Thr or Val
<220> FEATURE:
<221> NAME/KEY: MOD_RES
<222> LOCATION: (28)..(28)
<223> OTHER INFORMATION: Thr, Ser or Ala
<220> FEATURE:
<221> NAME/KEY: MOD_RES
<222> LOCATION: (34)..(34)
<223> OTHER INFORMATION: Ile or Val
<220> FEATURE:
<221> NAME/KEY: MOD_RES
<222> LOCATION: (35)..(35)
<223> OTHER INFORMATION: Ser or Thr
<220> FEATURE:
<221> NAME/KEY: MOD_RES
<222> LOCATION: (50)..(50)
<223> OTHER INFORMATION: Gly or Ala
<220> FEATURE:
<221> NAME/KEY: MOD_RES
<222> LOCATION: (54)..(54)
<223> OTHER INFORMATION: Pro or Gly
<220> FEATURE:
<221> NAME/KEY: MOD_RES
<222> LOCATION: (55)..(55)
<223> OTHER INFORMATION: Ile or Met
<220> FEATURE:
<221> NAME/KEY: MOD_RES
<222> LOCATION: (60)..(60)
<223> OTHER INFORMATION: Ala or Thr
<220> FEATURE:
<221> NAME/KEY: MOD_RES
<222> LOCATION: (70)..(70)
<223> OTHER INFORMATION: Val or Leu
<220> FEATURE:
<221> NAME/KEY: MOD_RES
<222> LOCATION: (72)..(72)
<223> OTHER INFORMATION: Ile, Leu or Met
<220> FEATURE:
<221> NAME/KEY: MOD_RES
<222> LOCATION: (76)..(76)
<223> OTHER INFORMATION: Lys or Glu
<220> FEATURE:
<221> NAME/KEY: MOD_RES
<222> LOCATION: (77)..(77)
<223> OTHER INFORMATION: Ser, Leu or Met
<220> FEATURE:
<221> NAME/KEY: MOD_RES
<222> LOCATION: (91)..(91)
<223> OTHER INFORMATION: Glu or Asp
<220> FEATURE:
<221> NAME/KEY: MOD_RES
<222> LOCATION: (107)..(107)
<223> OTHER INFORMATION: Ser, Thr or Asn
<220> FEATURE:
<221> NAME/KEY: MOD_RES
<222> LOCATION: (108)..(108)
<223> OTHER INFORMATION: Ser or Thr
<220> FEATURE:
<221> NAME/KEY: MOD_RES
<222> LOCATION: (114)..(114)
<223> OTHER INFORMATION: Gln, Lys, Gly or Arg
<220> FEATURE:
<221> NAME/KEY: MOD_RES
<222> LOCATION: (117)..(117)
<223> OTHER INFORMATION: Leu, Thr or Met

<400> SEQUENCE: 161

Xaa Xaa Gln Leu Val Gln Ser Gly Xaa Glu Val Xaa Lys Pro Gly Xaa
```

```
                1               5                   10                  15
            Ser Val Xaa Xaa Ser Cys Lys Xaa Ser Gly Gly Xaa Phe Ser Ser Tyr
                            20                  25                  30

Ala Xaa Xaa Trp Val Arg Gln Ala Pro Gly Gln Gly Leu Glu Trp Met
                        35                  40                  45

Gly Xaa Gly Ile Ile Xaa Xaa Phe Gly Thr Thr Xaa Asn Tyr Ala Gln
                50                  55                  60

Lys Phe Gln Gly Arg Xaa Thr Xaa Thr Ala Asp Xaa Xaa Thr Ser Thr
            65                  70                  75                  80

Ala Tyr Met Glu Leu Ser Ser Leu Arg Ser Xaa Asp Thr Ala Val Tyr
                            85                  90                  95

Tyr Cys Ala Arg Gly Ser Tyr Tyr Glu Xaa Xaa Leu Asp Tyr Trp
                        100                 105                 110

Gly Xaa Gly Thr Xaa
                        115
```

<210> SEQ ID NO 162
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
            Pro Glu Leu Thr Gln Pro Pro Ser Ala Ser Gly Thr Pro Gly Gln Arg
            1               5                   10                  15

Val Thr Ile Ser Cys Ser Gly Ser Ser Ser Asn Ile Gly Ser Asn Thr
                            20                  25                  30

Val Asn Trp Tyr Gln Gln Leu Pro Gly Thr Ala Pro Lys Leu Leu Ile
                        35                  40                  45

Tyr Ser Asn Asn Gln Arg Pro Ser Gly Val Pro Asp Arg Phe Ser Gly
                50                  55                  60

Ser Lys Ser Gly Thr Ser Ala Ser Leu Ala Ile Ser Gly Leu Gln Ser
            65                  70                  75                  80

Glu Asp Glu Ala Asp Tyr Tyr Cys Ala Ala Trp Asp Asp Ser Leu Asn
                            85                  90                  95

Gly Trp Val Phe Gly Gly Gly Thr Lys Leu Thr Val Leu
                        100                 105
```

<210> SEQ ID NO 163
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
            Asp Ile Gln Met Thr Gln Ser Pro Ser Ser Leu Ser Ala Phe Val Gly
            1               5                   10                  15

Asp Arg Val Thr Ile Thr Cys Gln Ala Ser Gln Asp Ile Ser Asn Tyr
                            20                  25                  30

Leu Asn Trp Tyr Gln Gln Lys Pro Gly Lys Ala Pro Lys Leu Leu Ile
                        35                  40                  45

Tyr Asp Ala Thr Asn Leu Glu Thr Gly Val Pro Ser Arg Phe Ser Gly
                50                  55                  60

Ser Gly Ser Gly Thr Asp Phe Thr Phe Thr Ile Ser Ser Leu Gln Pro
```

```
                65                  70                  75                  80
Glu Asp Ile Ala Thr Tyr Tyr Cys Gln Gln Tyr Asp Asn Leu Pro Leu
                    85                  90                  95
Thr Phe Gly Gly Gly Thr Lys Val Asp Ile Lys Arg
                100                 105
```

<210> SEQ ID NO 164
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

```
Gln Ser Val Leu Thr Gln Pro Pro Ser Ala Ser Gly Thr Pro Gly Gln
1               5                   10                  15

Arg Val Thr Leu Ser Cys Ser Gly Ser Ser Asn Ile Gly Gly Asn
            20                  25                  30

Ser Val Asn Trp Tyr Gln His Val Pro Gly Thr Ala Pro Lys Leu Leu
        35                  40                  45

Met His Ser Asp Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Trp Val Phe Gly Gly Gly Thr Lys Val Thr Val Leu
            100                 105                 110
```

<210> SEQ ID NO 165
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Val Pro Asp Arg Phe Ser
    50                  55                  60

Gly Ser Gly Ser Gly Thr Asp Phe Thr Leu Thr Ile Asn Arg Leu Glu
65                  70                  75                  80

Pro Glu Asp Phe Ala Val Tyr Tyr Cys Gln His Tyr Ser Arg Ser Leu
                85                  90                  95

Thr Phe Gly Gly Gly Thr Lys Val Glu Ile Lys Arg Thr
            100                 105
```

<210> SEQ ID NO 166
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 166

```
Gln Ser Val Leu Thr Gln Pro Pro Ser Val Ser Ala Ala Pro Gly Gln
1               5                   10                  15

Met Val Thr Ile Ser Cys Ser Gly Ser Asn Ser Asn Ile Gly Asn Asn
            20                  25                  30

Tyr Ile Ser Trp Tyr Gln Gln Leu Pro Gly Ser Ala Pro Arg Leu Leu
        35                  40                  45

Ile Tyr Asn Asn Tyr Lys Arg Pro Ser Gly Ile Pro Asp Arg Phe Ser
    50                  55                  60

Ala Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ser Val Val Phe Gly Gly Gly Thr Lys Val Thr Val Leu
            100                 105                 110
```

<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 167

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Thr Gly Ala Gly
            20                  25                  30

Asn His Val His Trp Tyr Gln Gln Val Ala Gly Ala Ala Pro Lys Leu
        35                  40                  45

Leu Ile Ser Asn Asn Asn Arg Pro Ser Gly Val Pro Asp Arg Phe
    50                  55                  60

Ser Ala Ser Lys Ser Gly Thr Ser Ala Ser Leu Asp Ile Thr Gly Leu
65                  70                  75                  80

Gln Ala Glu Asp Glu Ala Asp Tyr Tyr Cys Gln Ser Tyr Asp Asn Ser
                85                  90                  95

Leu Asn Asp Trp Val Phe Gly Gly Gly Thr Gln Leu Thr Val Leu
            100                 105                 110
```

<210> SEQ ID NO 168
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 168

```
Gln Ser Val Val Thr Gln Pro Pro Ser Glu Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Phe Pro Gly Ala Ala Pro Lys Leu Leu
        35                  40                  45

Ile Phe Glu Asn Asn Lys Arg His Ser Gly Ile Pro Asp Arg Phe Ser
    50                  55                  60
```

```
Gly Ser Lys Ser Gly Thr Ser Ala Thr Leu Gly Ile Ala Glu Leu Gln
 65                  70                  75                  80

Thr Gly Asp Glu Ala Asp Tyr Tyr Cys Gly Val Trp Asp Ser Ser Leu
                 85                  90                  95

Ser Ala Trp Val Phe Gly Gly Gly Thr Gln Leu Thr Val Leu
            100                 105                 110

<210> SEQ ID NO 169
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asn Phe Met Leu Thr Gln Pro His Ser Val Ser Glu Ser Pro Gly Lys
  1               5                  10                  15

Thr Val Thr Phe Ser Cys Thr Arg Ser Ser Gly Ser Ile Ala Ser Lys
                 20                  25                  30

Tyr Val Gln Trp Tyr Gln Gln Arg Pro Gly Ser Ala Pro Thr Ile Val
             35                  40                  45

Ile Phe Glu Asn Thr Lys Arg Pro Tyr Gly Val Pro Asp Arg Phe Ser
 50                  55                  60

Gly Ser Ile Asp Ser Ser Ser Asn Ser Ala Ser Leu Thr Ile Ser Gly
 65                  70                  75                  80

Leu Lys Thr Glu Asp Glu Ala Asp Tyr Tyr Cys Gln Ser Tyr Asp Ser
                 85                  90                  95

Ser Asn His Trp Val Phe Gly Gly Gly Thr Gln Leu Thr Val Leu Ser
            100                 105                 110

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Val Thr Val Ser Ser
  1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Arg Val Ser Ser
  1               5

<210> SEQ ID NO 172
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 172
tttttttttt tttttttt                                                    18

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

His His His His His His
1               5

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

His His His His His His His His His His
1               5                   10

<210> SEQ ID NO 175
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, g, t, unknown or other

<400> SEQUENCE: 175
ggccnnnnng gcc                                                         13

<210> SEQ ID NO 176
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Pro Glu Leu Thr Gln Pro His Ser Val Ser Glu Ser Pro Gly Lys Thr
1               5                   10                  15

Val Thr Ile Ser Cys Thr Gly Ser Gly Gly Arg Ile Ala Thr Asn His
            20                  25                  30

Val Gln Trp Tyr Gln Gln Arg Pro Gly Ser Ala Pro Thr Ile Val Ile
        35                  40                  45

Tyr Glu Asn Asn Gln Arg Pro Ser Gly Val Pro Asn Arg Phe Ser Gly
    50                  55                  60

Ser Ile Asp Asp Ser Ser Asn Ser Ala Ser Leu Thr Ile Ser Ala Leu
65                  70                  75                  80

Arg Thr Glu Asp Glu Ala Asp Tyr Tyr Cys Gln Ser Ala Asp Ala Thr
                85                  90                  95

Asn Val Phe Phe Gly Gly Gly Thr Lys Val Thr Val Leu
```

100                 105

<210> SEQ ID NO 177
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
            115                 120

<210> SEQ ID NO 178
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
                100                 105                 110

Gly Thr Thr Val Thr Val Ser Ser
            115                 120

<210> SEQ ID NO 179
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
        115                 120

<210> SEQ ID NO 180
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
        115                 120

<210> SEQ ID NO 181
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
            115                 120

<210> SEQ ID NO 182
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
            115                 120

<210> SEQ ID NO 183
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

```
Met Glu Leu Ser Ser Leu Arg Ser Glu Asp Thr Ala Val Tyr Tyr Cys
             85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
        115                 120

<210> SEQ ID NO 184
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Arg Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 185
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Gly Ser Tyr Tyr Tyr Glu Ser Ser Leu Asp Tyr Trp Gly Arg
            100                 105                 110

Gly Thr Leu Val Thr Val Ser Ser
        115                 120
```

-continued

<210> SEQ ID NO 186
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 186

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Glu Ser Ser Leu Asp Tyr Trp Gly Gln
            100                 105                 110

Gly Thr Leu Val Thr Val Ser Ser
            115                 120

<210> SEQ ID NO 187
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 187

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Glu Ser Ser Leu Asp Tyr Trp Gly Arg
            100                 105                 110

Gly Thr Met Val Thr Val Ser Ser
            115                 120

<210> SEQ ID NO 188
<211> LENGTH: 120
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 188

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met Val Thr Val Ser Ser
        115                 120

<210> SEQ ID NO 189
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 190
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

```
Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                      55                  60

Gln Gly Arg Val Thr Leu Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Glu Ser Ser Leu Asp Tyr Trp Gly Gln Gln
                100                 105                 110

Gly Thr Met Val Thr Val Ser Ser
            115                 120
```

<210> SEQ ID NO 191
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 191

```
Gln Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                      55                  60

Gln Gly Arg Val Thr Leu Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Glu Ser Ser Leu Asp Tyr Trp Gly Lys
                100                 105                 110

Gly Thr Met Val Thr Val Ser Ser
            115                 120
```

<210> SEQ ID NO 192
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (89)..(89)
<223> OTHER INFORMATION: Any amino acid

<400> SEQUENCE: 192

```
Gln Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
 50                      55                  60
```

Gln Gly Arg Val Thr Leu Thr Ala Asp Glu Leu Thr Ser Thr Ala Tyr
65                  70                  75                  80

Met Glu Leu Ser Ser Leu Arg Ser Xaa Asp Thr Ala Val Tyr Tyr Cys
                85                  90                  95

Ala Arg Gly Ser Tyr Tyr Glu Ser Ser Leu Asp Tyr Trp Gly Gln
            100                 105                 110

Gly Thr Leu Val Thr Val Ser Ser
        115                 120

<210> SEQ ID NO 193
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Gln
            100                 105                 110

Gly Thr Leu Val Thr Val Ser Ser
        115                 120

<210> SEQ ID NO 194
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Gln Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Thr Thr Leu Asp Tyr Trp Gly Arg
            100                 105                 110

```
Gly Thr Leu Val Thr Val Ser Ser
        115                 120

<210> SEQ ID NO 195
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Gln Val Gln Leu Val Gln Ser Gly Ala Glu Val Lys Lys Pro Gly Ser
1               5                   10                  15

Ser Val Lys Val Ser Cys Lys Thr Ser Gly Gly Ser Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met Val Thr Val Ser Ser
        115                 120

<210> SEQ ID NO 196
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
        115                 120

<210> SEQ ID NO 197
<211> LENGTH: 120
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 197

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 198
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
        115                 120

<210> SEQ ID NO 199
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Gln Val Gln Leu Val Gln Ser Gly Ala Glu Val Lys Lys Pro Gly Ser
1               5                   10                  15
```

```
Ser Val Lys Val Ser Cys Lys Thr Thr Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met Val Thr Val Ser Ser
            115                 120

<210> SEQ ID NO 200
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(24)
<223> OTHER INFORMATION: Any amino acid

<400> SEQUENCE: 200

Gln Val Gln Leu Val Gln Ser Gly Ala Glu Val Lys Lys Pro Gly Ser
1               5                   10                  15

Ser Val Lys Val Ser Cys Lys Xaa Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
            115                 120

<210> SEQ ID NO 201
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
        115                 120

<210> SEQ ID NO 202
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Glu Val Gln Leu Val Gln Ser Gly Thr Glu Val Lys Lys Pro Gly Ser
1               5                   10                  15

Ser Val Lys Leu Ser Cys Lys Ala Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Arg
                100                 105                 110

Gly Thr Met Val Thr Val Ser Ser
        115                 120

<210> SEQ ID NO 203
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Glu Val Gln Leu Val Gln Ser Gly Thr Glu Val Lys Lys Pro Gly Ser
1               5                   10                  15

Ser Val Lys Val Ser Cys Lys Val Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95
```

```
Ala Arg Gly Ser Tyr Tyr Tyr Glu Ser Ser Leu Asp Tyr Trp Gly Gly
            100                 105                 110

Gly Thr Thr Val Thr Val Ser Ser
        115                 120

<210> SEQ ID NO 204
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Glu Val Gln Leu Val Gln Ser Gly Ala Glu Val Gln Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 205
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Gln Ser Gly Ala Glu Val Lys Lys Pro Gly Ala
1               5                   10                  15

Ser Val Lys Val Ser Cys Lys Ala Ser Gly Gly Ala Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met Val Thr Val Ser Ser
        115                 120

<210> SEQ ID NO 206
```

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Glu Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Gln
            100                 105                 110

Gly Thr Leu Val Thr Val Ser Ser
        115                 120

<210> SEQ ID NO 207
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Leu Thr Ile Thr Ala Asp Glu Met Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Lys
            100                 105                 110

Gly Thr Leu Val Thr Val Ser Ser
        115                 120

<210> SEQ ID NO 208
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Val Gln Ser Gly Ala Glu Val Lys Lys Pro Gly Ser
1               5                   10                  15

Ser Val Arg Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
50                  55                  60

Gln Gly Arg Leu Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Thr Leu Asp Tyr Trp Gly Arg
            100                 105                 110

Gly Thr Met Val Thr Val Ser Ser
        115                 120

<210> SEQ ID NO 209
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Leu Val Thr Val Ser Ser
        115                 120

<210> SEQ ID NO 210
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

```
Gly Ala Ile Ile Gly Met Phe Gly Thr Thr Asn Tyr Ala Gln Lys Phe
            50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                    85                  90                  95

Ala Arg Gly Ser Tyr Tyr Tyr Glu Ser Ser Leu Asp Tyr Trp Gly Lys
                100                 105                 110

Gly Thr Leu Val Thr Val Ser Ser
            115                 120

<210> SEQ ID NO 211
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Gln Leu Val Gln Ser Gly Ala Glu Val Lys Lys Pro Gly Ser
 1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
            50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                    85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
            115                 120

<210> SEQ ID NO 212
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Val Gln Ser Gly Ala Glu Val Lys Lys Pro Gly Ser
 1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
            50                  55                  60

Gln Gly Arg Val Thr Ile Thr Ala Asp Glu Leu Thr Ser Thr Ala Tyr
 65                  70                  75                  80

Met Glu Leu Ser Ser Leu Arg Ser Asp Asp Thr Ala Val Tyr Tyr Cys
                    85                  90                  95
```

Ala Arg Gly Ser Tyr Tyr Tyr Glu Ser Ser Leu Asp Tyr Trp Gly Gln
            100                 105                 110

Gly Thr Met Val Thr Val Ser Ser
        115                 120

<210> SEQ ID NO 213
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
        115                 120

<210> SEQ ID NO 214
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Thr Val Thr Val Ser Ser
        115                 120

<210> SEQ ID NO 215
<211> LENGTH: 120

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
        115                 120

<210> SEQ ID NO 216
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 217
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Val Gln Ser Gly Ala Glu Val Lys Lys Pro Gly Ser

```
                1               5                   10                  15
Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
            50                  55                  60

Gln Gly Arg Val Thr Leu Thr Ala Asp Glu Leu Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
            115                 120
```

<210> SEQ ID NO 218
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
            50                  55                  60

Gln Gly Arg Val Thr Leu Thr Ala Asp Glu Leu Thr Ser Thr Ala Tyr
65                      70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Met Val Thr Val Ser Ser
            115                 120
```

<210> SEQ ID NO 219
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

```
Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
```

```
                     50                  55                  60

Gln Gly Arg Val Thr Leu Thr Ala Asp Glu Leu Thr Ser Thr Ala Tyr
 65                  70                  75                  80

Met Glu Leu Ser Ser Leu Arg Ser Glu Asp Thr Ala Val Tyr Tyr Cys
                     85                  90                  95

Ala Arg Gly Ser Tyr Tyr Tyr Glu Ser Ser Leu Asp Tyr Trp Gly Arg
                100                 105                 110

Gly Thr Leu Val Thr Val Ser Ser
            115                 120

<210> SEQ ID NO 220
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (74)..(74)
<223> OTHER INFORMATION: Any amino acid

<400> SEQUENCE: 220

Glu Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
     50                  55                  60

Gln Gly Arg Val Thr Leu Thr Ala Asp Xaa Leu Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Ser Ser Leu Asp Tyr Trp Gly Arg
                100                 105                 110

Gly Thr Leu Val Thr Val Ser Ser
            115                 120

<210> SEQ ID NO 221
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 221

Glu Val Gln Leu Val Gln Ser Gly Ala Glu Val Lys Lys Pro Gly Ser
 1               5                  10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
     50                  55                  60

Gln Gly Arg Val Thr Leu Thr Ala Asp Glu Leu Thr Ser Thr Ala Tyr
 65                  70                  75                  80
```

```
Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Arg
            100                 105                 110

Gly Thr Met Val Thr Val Ser Ser
        115                 120
```

<210> SEQ ID NO 222
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

```
Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Met Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Lys
            100                 105                 110

Gly Thr Leu Val Thr Val Ser Ser
        115                 120
```

<210> SEQ ID NO 223
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Gln
            100                 105                 110

Gly Thr Leu Val Thr Val Ser Ser
        115                 120
```

<210> SEQ ID NO 224
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 224

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
        115                 120

<210> SEQ ID NO 225
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 225

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Leu Val Thr Val Ser Ser
        115                 120

<210> SEQ ID NO 226
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Met Val Thr Val Ser Ser
        115                 120

<210> SEQ ID NO 227
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 228
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Glu Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met

```
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Gln
            100                 105                 110

Gly Thr Met Val Thr Val Ser Ser
            115                 120

<210> SEQ ID NO 229
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Gly Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Glu Ser Ser Leu Asp Tyr Trp Gly Lys
            100                 105                 110

Gly Thr Met Val Thr Val Ser Ser
            115                 120

<210> SEQ ID NO 230
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Gly Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
```

85                  90                  95

Ala Arg Gly Ser Tyr Tyr Tyr Glu Ser Ser Leu Asp Tyr Trp Gly Arg
                100                 105                 110

Gly Thr Leu Val Thr Val Ser Ser
        115                 120

<210> SEQ ID NO 231
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gln Met Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
                100                 105                 110

Gly Thr Met Val Thr Val Ser Ser
        115                 120

<210> SEQ ID NO 232
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Met Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
                100                 105                 110

Gly Thr Leu Val Thr Val Ser Ser
        115                 120

<210> SEQ ID NO 233
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Leu Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
        115                 120

<210> SEQ ID NO 234
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 235
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
                100                 105                 110

Gly Thr Met Val Thr Val Ser Ser
            115                 120

<210> SEQ ID NO 236
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Gln Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Asn Ser Leu Asp Tyr Trp Gly Lys
                100                 105                 110

Gly Thr Leu Val Thr Val Ser Ser
            115                 120

<210> SEQ ID NO 237
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Gln Gln Ser Gly Ala Glu Val Lys Pro Gly Ser
1               5                   10                  15

Ser Val Arg Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

```
Gly Gly Ile Ile Gly Met Phe Gly Thr Thr Asn Tyr Ala Gln Lys Phe
            50                  55                  60

Gln Gly Arg Leu Thr Ile Thr Ala Asp Glu Met Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Thr Thr Leu Asp Tyr Trp Gly Gln
                100                 105                 110

Gly Thr Met Val Thr Val Ser Ser
            115                 120

<210> SEQ ID NO 238
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Gln Gln Ser Gly Ala Glu Val Lys Lys Pro Gly Ser
  1               5                  10                  15

Ser Val Arg Val Ser Cys Lys Thr Ser Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Gly Ile Ile Gly Met Phe Gly Thr Thr Asn Tyr Ala Gln Lys Phe
         50                  55                  60

Gln Gly Arg Leu Thr Ile Thr Ala Asp Glu Met Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ser Tyr Tyr Tyr Glu Thr Thr Leu Asp Tyr Trp Gly Lys
                100                 105                 110

Gly Thr Leu Val Thr Val Ser Ser
            115                 120

<210> SEQ ID NO 239
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Gln Ser Gly Ala Glu Val Lys Lys Pro Gly Ser
  1               5                  10                  15

Ser Val Lys Val Ser Cys Lys Thr Ser Gly Gly Thr Phe Ser Ser Tyr
                 20                  25                  30

Ala Val Thr Trp Val Arg Gln Ala Pro Gly Gln Gly Leu Glu Trp Met
             35                  40                  45

Gly Gly Ile Ile Gly Met Phe Gly Thr Thr Asn Tyr Ala Gln Lys Phe
         50                  55                  60

Gln Gly Arg Val Thr Met Thr Ala Asp Glu Met Thr Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 240
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Met Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Met Val Thr Val Ser Ser
        115                 120

<210> SEQ ID NO 241
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 242

<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Leu Val Thr Val Ser Ser
        115                 120

<210> SEQ ID NO 243
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 243

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Pro Val Thr Val Ser Ser
        115                 120

<210> SEQ ID NO 244
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

-continued

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Leu Val Thr Val Ser Ser
            115                 120

<210> SEQ ID NO 245
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Met Val Thr Val Ser Ser
            115                 120

<210> SEQ ID NO 246
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
            35                  40                  45

```
Gly Ala Ile Ile Gly Met Phe Gly Thr Thr Asn Tyr Ala Gln Lys Phe
        50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
                100                 105                 110

Gly Thr Leu Val Thr Val Ser Ser
        115                 120

<210> SEQ ID NO 247
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Thr Ser Leu Asp Tyr Trp Gly Lys
                100                 105                 110

Gly Thr Leu Val Thr Val Ser Ser
        115                 120

<210> SEQ ID NO 248
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
                20                  25                  30

Ala Val Thr Trp Val Arg Gln Ala Pro Gly Gln Gly Leu Glu Trp Met
            35                  40                  45

Gly Gly Ile Ile Gly Met Phe Gly Thr Thr Asn Tyr Ala Gln Lys Phe
        50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Gly Ser Tyr Tyr Tyr Glu Ser Ser Leu Asp Tyr Trp Gly Arg
            100                 105                 110

Gly Thr Met Val Thr Val Ser Ser
        115                 120

<210> SEQ ID NO 249
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Glu Val Gln Leu Val Gln Ser Gly Ala Glu Val Lys Lys Pro Gly Ala
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Gln
            100                 105                 110

Gly Thr Leu Val Thr Val Ser Ser
        115                 120

<210> SEQ ID NO 250
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Ala Ile Ile Gly Met Phe Gly Thr Thr Asn Tyr Ala Gln Lys Phe
    50                  55                  60

Gln Gly Arg Val Thr Leu Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Lys
            100                 105                 110

Gly Thr Thr Val Thr Val Ser Ser
        115                 120

<210> SEQ ID NO 251
<211> LENGTH: 120

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Glu Val Gln Leu Val Gln Ser Gly Ala Glu Val Lys Lys Pro Gly Ser
1               5                   10                  15

Ser Val Lys Val Ser Cys Lys Thr Ser Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Leu Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Asn Ser Leu Asp Tyr Trp Gly Arg
            100                 105                 110

Gly Thr Leu Val Thr Val Ser Ser
            115                 120

<210> SEQ ID NO 252
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Glu Val Gln Leu Val Gln Ser Gly Ala Glu Val Lys Lys Pro Gly Ser
1               5                   10                  15

Ser Val Lys Val Ser Cys Lys Thr Thr Gly Gly Thr Phe Ser Ser Tyr
            20                  25                  30

Ala Val Thr Trp Val Arg Gln Ala Pro Gly Gln Gly Leu Glu Trp Met
        35                  40                  45

Gly Gly Ile Ile Gly Met Phe Gly Thr Thr Asn Tyr Ala Gln Lys Phe
    50                  55                  60

Gln Gly Arg Val Thr Ile Thr Ala Asp Glu Met Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ser Tyr Tyr Tyr Glu Ser Ser Leu Asp Tyr Trp Gly Arg
            100                 105                 110

Gly Thr Met Val Thr Val Ser Ser
            115                 120

<210> SEQ ID NO 253
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Glu Val Gln Leu Val Gln Ser Gly Ala Glu Val Lys Lys Pro Gly Ser

-continued

```
                1               5                  10                 15
Ser Val Lys Val Ser Cys Lys Thr Thr Gly Gly Thr Phe Ser Ser Tyr
                        20                 25                 30

Ala Val Thr Trp Val Arg Gln Ala Pro Gly Gln Gly Leu Glu Trp Met
                        35                 40                 45

Gly Gly Ile Ile Gly Met Phe Gly Thr Thr Asn Tyr Ala Gln Lys Phe
            50                 55                 60

Gln Gly Arg Val Thr Ile Thr Ala Asp Glu Met Thr Ser Thr Ala Tyr
65                      70                 75                 80

Met Glu Leu Ser Ser Leu Arg Ser Glu Asp Thr Ala Val Tyr Tyr Cys
                        85                 90                 95

Ala Arg Gly Ser Tyr Tyr Tyr Glu Ser Ser Leu Asp Tyr Trp Gly Lys
                   100                105                110

Gly Thr Met Val Thr Val Ser Ser
            115                120

<210> SEQ ID NO 254
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Glu Gln Ser Gly Ala Glu Val Lys Lys Pro Gly Ser
1               5                  10                 15

Ser Val Lys Val Ser Cys Lys Thr Ser Gly Gly Thr Phe Ser Ser Tyr
                        20                 25                 30

Ala Val Thr Trp Val Arg Gln Ala Pro Gly Gln Gly Leu Glu Trp Met
                        35                 40                 45

Gly Ala Ile Ile Gly Met Phe Gly Thr Thr Asn Tyr Ala Gln Lys Phe
            50                 55                 60

Gln Gly Arg Val Thr Leu Thr Ala Asp Glu Leu Thr Ser Thr Ala Tyr
65                      70                 75                 80

Met Glu Leu Ser Ser Leu Arg Ser Glu Asp Thr Ala Val Tyr Tyr Cys
                        85                 90                 95

Ala Arg Gly Ser Tyr Tyr Tyr Glu Ser Ser Leu Asp Tyr Trp Gly Glu
                   100                105                110

Gly Thr Thr Val Thr Val Ser Ser
            115                120

<210> SEQ ID NO 255
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Gln Glu Ser Gly Pro Gly Leu Val Lys Pro Ser Glu
1               5                  10                 15

Thr Leu Ser Leu Thr Cys Thr Val Ser Gly Tyr Ser Phe Asp Ser Gly
                        20                 25                 30

Tyr Tyr Trp Gly Trp Leu Arg Gln Pro Pro Gly Lys Gly Leu Glu Trp
                        35                 40                 45

Ile Gly Ser Ile Tyr His Ser Arg Asn Thr Tyr Tyr Asn Pro Ser Leu
```

-continued

```
                    50                  55                  60
Lys Ser Arg Val Thr Ile Ser Val Asp Thr Ser Lys Asn Gln Phe Ser
 65                  70                  75                  80

Leu Gln Leu Ser Ser Val Thr Ala Ala Asp Thr Ala Val Tyr Tyr Cys
                 85                  90                  95

Ala Arg Gly Thr Trp Tyr Ser Ser Asn Leu Arg Tyr Trp Phe Asp Pro
            100                 105                 110

Trp Gly Lys Gly Thr Leu Val Arg Val Ser Ser
            115                 120
```

<210> SEQ ID NO 256
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Phe Met Leu Thr Gln Pro His Ser Val Ser Glu Ser Pro Gly Lys Thr
  1               5                  10                  15

Val Thr Ile Ser Cys Thr Gly Ser Gly Gly Asn Ile Ala Arg Asn Tyr
                 20                  25                  30

Val Gln Trp Tyr Gln Gln Arg Pro Gly Ser Ala Pro Val Thr Val Ile
             35                  40                  45

Leu Glu Asp Asp Lys Arg Pro Ser Gly Ile Pro Asp Arg Phe Ser Gly
 50                  55                  60

Ser Ile Asp Arg Ser Ser Asn Ser Ala Ser Leu Thr Ile Ser Gly Leu
 65                  70                  75                  80

Arg Thr Glu Asp Glu Ala Leu Tyr Tyr Cys Gln Ser Tyr Asp Asp Ser
                 85                  90                  95

Asp Leu Val Val Phe Gly Gly Gly Thr Lys Leu Thr
            100                 105
```

<210> SEQ ID NO 257
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

```
Phe Met Leu Thr Gln Pro His Ser Val Ser Glu Ser Pro Gly Lys Thr
  1               5                  10                  15

Val Thr Ile Ser Cys Thr Gly Ser Ser Gly Ser Ile Ala Ser Asn Tyr
                 20                  25                  30

Val Gln Trp Tyr Gln Gln Arg Pro Gly Ser Ala Pro Thr Thr Val Ile
             35                  40                  45

Tyr Glu Asp Tyr Gln Arg Pro Ser Gly Val Pro Asp Arg Phe Ser Gly
 50                  55                  60

Ser Ile Asp Ser Ser Ser Asn Ser Ala Ser Leu Thr Ile Ser Gly Leu
 65                  70                  75                  80

Lys Thr Glu Asp Glu Ala Asp Tyr Tyr Cys Gln Ser Tyr Asp Asp Ser
                 85                  90                  95

Asp His Leu Ile Phe Gly Gly Gly Thr Lys Leu Thr Val Leu
            100                 105                 110
```

<210> SEQ ID NO 258
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Ser Val Leu Thr Gln Pro Pro Ser Ala Ser Gly Thr Pro Gly Gln Arg
1               5                   10                  15

Val Thr Ile Ser Cys Ser Gly Ser Ser Ser Asn Ile Gly Ser Asn Thr
            20                  25                  30

Val Asn Trp Tyr Lys Gln Leu Pro Gly Thr Ala Pro Arg Leu Leu Ile
        35                  40                  45

Tyr Ser Asn Asp Gln Arg Pro Ser Gly Val Pro Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asn Tyr Tyr Cys Ala Ala Trp Asp Asp Ser Leu Ser
                85                  90                  95

Gly Trp Val Phe Gly Gly Gly Thr Lys Leu Thr Val Leu
            100                 105

<210> SEQ ID NO 259
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (71)..(71)
<223> OTHER INFORMATION: Any amino acid
<220> FEATURE:
<221> NAME/KEY: MOD_RES
<222> LOCATION: (90)..(90)
<223> OTHER INFORMATION: Any amino acid
<220> FEATURE:
<221> NAME/KEY: MOD_RES
<222> LOCATION: (103)..(103)
<223> OTHER INFORMATION: Any amino acid

<400> SEQUENCE: 259

Ser Val Leu Thr Gln Pro Pro Ser Ala Ser Gly Thr Pro Gly Gln Arg
1               5                   10                  15

Val Thr Leu Ser Cys Ser Gly Ser Ser Ser Asn Ile Gly Gly Asn Ser
            20                  25                  30

Val Asn Trp Tyr Gln His Val Pro Gly Thr Ala Pro Lys Leu Leu Met
        35                  40                  45

His Ser Asp Asp Gln Arg Pro Ser Gly Val Pro Asp Arg Phe Ser Gly
    50                  55                  60

Ser Lys Ser Gly Thr Ser Xaa Ser Leu Ala Ile Ser Gly Leu Gln Ser
65                  70                  75                  80

Glu Asp Glu Ala Asp Tyr Tyr Cys Ala Xaa Trp Asp Asp Ser Leu Asn
                85                  90                  95

Ala Trp Val Phe Gly Gly Xaa Thr Lys Val Thr Val Leu
            100                 105

<210> SEQ ID NO 260
<211> LENGTH: 109
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 260

Pro Glu Leu Thr Gln Pro His Ser Val Ser Glu Ser Pro Gly Lys Thr
1               5                   10                  15

Val Thr Ile Ser Cys Thr Gly Ser Gly Gly Arg Ile Ala Thr Asn His
            20                  25                  30

Val Gln Trp Tyr Gln Gln Arg Pro Gly Ser Ala Pro Thr Ile Val Ile
        35                  40                  45

Tyr Glu Asn Asn Gln Arg Pro Ser Gly Val Pro Asn Arg Phe Ser Gly
    50                  55                  60

Ser Ile Asp Asp Ser Ser Asn Ser Ala Ser Leu Thr Ile Ser Ala Leu
65                  70                  75                  80

Arg Thr Glu Asp Glu Ala Asp Tyr Tyr Cys Gln Ser Ala Asp Ala Thr
                85                  90                  95

Asn Val Phe Phe Gly Gly Gly Thr Lys Val Thr Val Leu
            100                 105

<210> SEQ ID NO 261
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (103)..(103)
<223> OTHER INFORMATION: Any amino acid

<400> SEQUENCE: 261

Pro Glu Leu Thr Gln Pro Pro Ser Ala Ser Gly Thr Pro Gly Gln Arg
1               5                   10                  15

Val Thr Ile Ser Cys Ser Gly Ser Ser Ser Asn Ile Gly Ser Asn Thr
            20                  25                  30

Val Asn Trp Tyr Gln Gln Leu Pro Gly Thr Ala Pro Lys Leu Leu Ile
        35                  40                  45

Tyr Ser Asn Asn Gln Arg Pro Ser Gly Val Pro Asp Arg Phe Ser Gly
    50                  55                  60

Ser Lys Ser Gly Thr Ser Ala Ser Leu Ala Ile Ser Gly Leu Gln Ser
65                  70                  75                  80

Glu Asp Glu Ala Asp Tyr Tyr Cys Ala Ala Trp Asp Asp Ser Leu Asn
                85                  90                  95

Gly Trp Val Phe Gly Gly Xaa Thr Lys Leu Thr Val Leu
            100                 105

<210> SEQ ID NO 262
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Asp Ile Gln Met Thr Gln Ser Pro Ser Ser Leu Ser Ala Phe Val Gly
1               5                   10                  15

Asp Arg Val Thr Ile Thr Cys Gln Ala Ser Gln Asp Ile Ser Asn Tyr
```

```
                    20                  25                  30
Leu Asn Trp Tyr Gln Gln Lys Pro Gly Lys Ala Pro Lys Leu Leu Ile
                35                  40                  45

Tyr Asp Ala Thr Asn Leu Glu Thr Gly Val Pro Ser Arg Phe Ser Gly
            50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Asp Ile Lys Arg
            100                 105
```

<210> SEQ ID NO 263
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 263

```
tgg atg gga agg atc atc cct atc ctt ggt ata gca aac tac gca        45
Trp Met Gly Arg Ile Ile Pro Ile Leu Gly Ile Ala Asn Tyr Ala
1               5                   10                  15
```

<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Trp Met Gly Arg Ile Ile Pro Ile Leu Gly Ile Ala Asn Tyr Ala
1               5                   10                  15
```

<210> SEQ ID NO 265
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 265

```
tgg atg ggc gcg atc atc ggt atg ttt ggt aca aca aac tac gca        45
Trp Met Gly Ala Ile Ile Gly Met Phe Gly Thr Thr Asn Tyr Ala
1               5                   10                  15
```

<210> SEQ ID NO 266
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

```
Trp Met Gly Ala Ile Ile Gly Met Phe Gly Thr Thr Asn Tyr Ala
```

<210> SEQ ID NO 267
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(45)

<400> SEQUENCE: 267

```
tgg atg gga ggg atc atc ggt atg ttt gga aca acc aac tat gca      45
Trp Met Gly Gly Ile Ile Gly Met Phe Gly Thr Thr Asn Tyr Ala
1               5                   10                  15
```

<210> SEQ ID NO 268
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

```
Trp Met Gly Gly Ile Ile Gly Met Phe Gly Thr Thr Asn Tyr Ala
1               5                   10                  15
```

<210> SEQ ID NO 269
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(45)

<400> SEQUENCE: 269

```
tgg atg gga gcg atc atc ggt atg ttt ggt aca aca aac tac gca      45
Trp Met Gly Ala Ile Ile Gly Met Phe Gly Thr Thr Asn Tyr Ala
1               5                   10                  15
```

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

```
Trp Met Gly Ala Ile Ile Gly Met Phe Gly Thr Thr Asn Tyr Ala
1               5                   10                  15
```

<210> SEQ ID NO 271
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: CDS
<222> LOCATION: (1)..(45)

<400> SEQUENCE: 271

```
tgg atg ggc gcg atc atc ggt atg ttt ggt aca aca aac tac gca      45
Trp Met Gly Ala Ile Ile Gly Met Phe Gly Thr Thr Asn Tyr Ala
1               5                   10                  15

<210> SEQ ID NO 272
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Trp Met Gly Ala Ile Ile Gly Met Phe Gly Thr Thr Asn Tyr Ala
1               5                   10                  15

<210> SEQ ID NO 273
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 273 tgg atg gga ggg atc atc ggt atg ttt ggt aca acg aac tat gca      45
Trp Met Gly Gly Ile Ile Gly Met Phe Gly Thr Thr Asn Tyr Ala
1               5                   10                  15

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Trp Met Gly Gly Ile Ile Gly Met Phe Gly Thr Thr Asn Tyr Ala
1               5                   10                  15

<210> SEQ ID NO 275
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(45)

<400> SEQUENCE: 275 tgg atg gga ggg atc atc ggt atg ttt ggt aca aca aac tac gca      45
Trp Met Gly Gly Ile Ile Gly Met Phe Gly Thr Thr Asn Tyr Ala
1               5                   10                  15

<210> SEQ ID NO 276
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276
```

```
Trp Met Gly Gly Ile Ile Gly Met Phe Gly Thr Thr Asn Tyr Ala
1               5                   10                  15
```

<210> SEQ ID NO 277
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 277

```
gtc acg att acc gcg gac aaa tcc acg agc aca gcc              36
Val Thr Ile Thr Ala Asp Lys Ser Thr Ser Thr Ala
1               5                   10
```

<210> SEQ ID NO 278
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

```
Val Thr Ile Thr Ala Asp Lys Ser Thr Ser Thr Ala
1               5                   10
```

<210> SEQ ID NO 279
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 279

```
gtc acg ctt acc gcg gac gaa tta acg tcc aca gcc              36
Val Thr Leu Thr Ala Asp Glu Leu Thr Ser Thr Ala
1               5                   10
```

<210> SEQ ID NO 280
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

```
Val Thr Leu Thr Ala Asp Glu Leu Thr Ser Thr Ala
1               5                   10
```

<210> SEQ ID NO 281
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 281

```
ctc aca atc acc gcg gac gag atg acg tcc aca gcc          36
Leu Thr Ile Thr Ala Asp Glu Met Thr Ser Thr Ala
1               5                   10
```

<210> SEQ ID NO 282
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

```
Leu Thr Ile Thr Ala Asp Glu Met Thr Ser Thr Ala
1               5                   10
```

<210> SEQ ID NO 283
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 283

```
gtc aca atc acc gcg gac gaa tta acg tcc aca gcc          36
Val Thr Ile Thr Ala Asp Glu Leu Thr Ser Thr Ala
1               5                   10
```

<210> SEQ ID NO 284
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

```
Val Thr Ile Thr Ala Asp Glu Leu Thr Ser Thr Ala
1               5                   10
```

<210> SEQ ID NO 285
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 285

```
gtc acg ctt acc gcg gac gaa tta acg tcc aca gcc          36
Val Thr Leu Thr Ala Asp Glu Leu Thr Ser Thr Ala
1               5                   10
```

<210> SEQ ID NO 286
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Val Thr Leu Thr Ala Asp Glu Leu Thr Ser Thr Ala
1               5                  10

<210> SEQ ID NO 287
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 287 gtc acg att acc gcg gac gag atg acg tcc aca gcc                    36
Val Thr Ile Thr Ala Asp Glu Met Thr Ser Thr Ala
1               5                  10

<210> SEQ ID NO 288
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Val Thr Ile Thr Ala Asp Glu Met Thr Ser Thr Ala
1               5                  10

<210> SEQ ID NO 289
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(36)

<400> SEQUENCE: 289 gtc acg att acc gcg gac gaa tta acg tcc aca gcc                    36
Val Thr Ile Thr Ala Asp Glu Leu Thr Ser Thr Ala
1               5                  10

<210> SEQ ID NO 290
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Val Thr Ile Thr Ala Asp Glu Leu Thr Ser Thr Ala
1               5                  10

<210> SEQ ID NO 291
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other

<400> SEQUENCE: 291 acn aar gcn tcn tay ctn agy acn agy agy agy ctn gay         39
Thr Lys Ala Ser Tyr Leu Ser Thr Ser Ser Ser Leu Asp
1               5                   10

<210> SEQ ID NO 292
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Thr Lys Ala Ser Tyr Leu Ser Thr Ser Ser Ser Leu Asp
1               5                   10

<210> SEQ ID NO 293
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:

```
<221> NAME/KEY: modified_base
<222> LOCATION: (30)..(30)
<223> OTHER INFORMATION: a, c, g, t, unknown or other

<400> SEQUENCE: 293 gcn cgn ggn ath tay tty tay ggn acn acn tay tty gay      39
Ala Arg Gly Ile Tyr Phe Tyr Gly Thr Thr Tyr Phe Asp
1               5                   10

<210> SEQ ID NO 294
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Ala Arg Gly Ile Tyr Phe Tyr Gly Thr Thr Tyr Phe Asp
1               5                   10

<210> SEQ ID NO 295
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: CDS
<222> LOCATION: (1)..(39)
<220> FEATURE:
<221> NAME/KEY: modified_base
<222> LOCATION: (3)..(3)
<223> OTHER INFORMATION: a, c, g, t, unknown or other
<220> FEATURE:
<221> NAME/KEY: modified_base
<222> LOCATION: (6)..(6)
<223> OTHER INFORMATION: a, c, g, t, unknown or other
<220> FEATURE:
<221> NAME/KEY: modified_base
<222> LOCATION: (9)..(9)
<223> OTHER INFORMATION: a, c, g, t, unknown or other
<220> FEATURE:
<221> NAME/KEY: modified_base
<222> LOCATION: (12)..(12)
<223> OTHER INFORMATION: a, c, g, t, unknown or other
<220> FEATURE:
<221> NAME/KEY: modified_base
<222> LOCATION: (18)..(18)
<223> OTHER INFORMATION: a, c, g, t, unknown or other
<220> FEATURE:
<221> NAME/KEY: modified_base
<222> LOCATION: (24)..(24)
<223> OTHER INFORMATION: a, c, g, t, unknown or other
<220> FEATURE:
<221> NAME/KEY: modified_base
<222> LOCATION: (27)..(27)
<223> OTHER INFORMATION: a, c, g, t, unknown or other
<220> FEATURE:
<221> NAME/KEY: modified_base
<222> LOCATION: (30)..(30)
<223> OTHER INFORMATION: a, c, g, t, unknown or other
<220> FEATURE:
<221> NAME/KEY: modified_base
<222> LOCATION: (36)..(36)
<223> OTHER INFORMATION: a, c, g, t, unknown or other

<400> SEQUENCE: 295 rcn mrn gsn wyn tay ytn wry rsn asn asn wry ytn gay      39
Xaa Xaa Xaa Xaa Tyr Xaa Xaa Xaa Xaa Xaa Xaa Xaa Asp
1               5                   10
```

```
<210> SEQ ID NO 296
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Ala
<220> FEATURE:
<221> NAME/KEY: MOD_RES
<222> LOCATION: (2)..(2)
<223> OTHER INFORMATION: Lys, Arg, Asn, His, Gln or Ser
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (4)..(4)
<223> OTHER INFORMATION: Ser, Ile, Thr, Phe, Leu or Met
<220> FEATURE:
<221> NAME/KEY: MOD_RES
<222> LOCATION: (6)..(6)
<223> OTHER INFORMATION: Leu or Phe
<220> FEATURE:
<221> NAME/KEY: MOD_RES
<222> LOCATION: (7)..(7)
<223> OTHER INFORMATION: Ser, Tyr, Asn or Cys
<220> FEATURE:
<221> NAME/KEY: MOD_RES
<222> LOCATION: (8)..(8)
<223> OTHER INFORMATION: Thr, Gly, Ser, Arg or Ala
<220> FEATURE:
<221> NAME/KEY: MOD_RES
<222> LOCATION: (9)..(10)
<223> OTHER INFORMATION: Ser, Thr or Arg
<220> FEATURE:
<221> NAME/KEY: MOD_RES
<222> LOCATION: (11)..(11)
<223> OTHER INFORMATION: Ser, Tyr, Asn or Cys
<220> FEATURE:
<221> NAME/KEY: MOD_RES
<222> LOCATION: (12)..(12)
<223> OTHER INFORMATION: Leu or Phe

<400> SEQUENCE: 296

Xaa Xaa Xaa Xaa Tyr Xaa Xaa Xaa Xaa Xaa Xaa Xaa Asp
1               5                   10
```

What is claimed is:

1. A composition comprising an antibody, or an antigen binding fragment thereof, comprising a heavy chain polypeptide comprising an amino acid sequence selected from the group consisting of SEQ ID NO:4, SEQ ID NO:9, SEQ ID NO:45 and SEQ ID NO:61, wherein the antibody:
   (i) neutralizes more than one subtype and/or more than one isolate of an influenza A virus,
   (ii) binds to a hemagglutinin (HA) stem polypeptide or fragment thereof that lacks an HA globular head polypeptide, and
   (iii) does not inhibit hemagglutination.

2. The composition of claim 1, effective against at least one additional influenza A virus subtype selected from the group consisting of H1, H2, H3, H5, H6, H7, H8, and H9.

3. The composition of claim 1, effective against at least two isolates of an influenza A virus subtype selected from the group consisting of H1, H2, H3, H5, H6, H7, H8, and H9.

4. The composition of claim 1, effective against at least one isolate of H1 influenza A virus subtype.

5. The composition of claim 1, effective against at least one isolate of H5 influenza A virus subtype.

6. The composition of claim 1, effective against isolates of H1 and H5 influenza A virus subtypes.

7. The composition of claim 1, wherein the antibody or antigen binding fragment thereof further comprises a light chain polypeptide comprising an amino acid sequence selected from the group consisting of SEQ ID NO:71, SEQ ID NO:81, SEQ ID NO:140, SEQ ID NO:158, SEQ ID NO:159, and SEQ ID NO:160.

8. The composition of claim 1, wherein at least one of said virus subtypes has the ability to infect humans.

9. The composition of claim 1, wherein at least one of said isolates has been obtained from a human subject.

10. The composition of claim 1, wherein at least one of said isolates has been obtained from a non-human animal.

11. The composition of claim 1, wherein the composition further contains an attenuated influenza A virus or a killed influenza A virus.

* * * * *